(12) United States Patent
Oppermann et al.

(10) Patent No.: US 6,677,432 B1
(45) Date of Patent: Jan. 13, 2004

(54) MUTATIONS OF THE C-TERMINAL PORTION OF TGF-β SUPERFAMILY PROTEINS

(75) Inventors: Hermann Oppermann, Medway, MA (US); Mei-Sheng Tai, Shrewsbury, MA (US); John McCartney, Holliston, MA (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 09/374,958

(22) Filed: Aug. 16, 1999

Related U.S. Application Data

(60) Provisional application No. 60/103,418, filed on Oct. 7, 1998.

(51) Int. Cl.[7] .............. C07K 14/00; C07K 14/495; C12N 15/00; L12N 15/62; A61K 38/00
(52) U.S. Cl. ............... 530/350; 530/399; 435/440; 435/445; 435/69.1; 536/23.4; 514/2
(58) Field of Search ............... 530/350, 351, 530/399; 435/440, 455, 69.1; 536/23.4; 514/2

(56) References Cited

U.S. PATENT DOCUMENTS

| | | |
|---|---|---|
| 5,011,691 A | 4/1991 | Oppermann et al. |
| 5,266,683 A | 11/1993 | Oppermann et al. |
| 5,399,677 A | 3/1995 | Wolfman et al. |
| 5,658,882 A | 8/1997 | Celeste et al. |
| 5,674,292 A | 10/1997 | Tucker et al. |
| 5,756,308 A | 5/1998 | Wolfman et al. |
| 5,770,444 A | 6/1998 | Lee et al. |
| 5,801,014 A | 9/1998 | Lee et al. |
| 5,804,416 A | 9/1998 | Wolfman et al. |
| 5,840,325 A | 11/1998 | Kuberasampath et al. |

FOREIGN PATENT DOCUMENTS

| | | |
|---|---|---|
| DE | 4131545 A1 | 3/1993 |
| EP | 0433225 A2 | 6/1991 |
| FR | 2720069 A1 | 11/1995 |
| WO | WO91/05565 | 5/1991 |
| WO | WO91/05802 | 5/1991 |
| WO | WO92/15323 | 9/1992 |

OTHER PUBLICATIONS

Ngo et al., 1994, The Protein Folding Problem and Tertiary Structure Prediction, pp. 492–495.*
Wells, Aditivity of Mutational Effects in Proteins, 1990, Biochemistry, vol. 26, No:37, pp. 8509–8517.*
Brunner, et al., Site–directed mutagenesis of cysteine residues in the pro region of the transforming growth factor β1 precursor, *J. Biol. Chem.*, 264, pp. 13660–13664 (1989).

Hilvert, et al., Chemical synthesis of proteins, *Chem. Biol.*, 1, pp. 201–203 (1994).

Lipscomb, et al., Context–dependent protein stabilization by methionine–to–leucine substitution shown in T4 lysozyme, *Protein Sci.*, 7, pp. 765–773 (1998).

Liu, et al., Peptide segment ligation strategy without use of protecting groups, *Proc. Natl. Acad. Sci. USA*, 91, pp. 6584–6588 (1994).

Miranda, et al., Accelerated chemical synthesis of peptides and small proteins, *Proc. Natl. Acad. Sci. USA*, 96, pp. 1181–1186 (1996).

Muir, et al., Expressed protein ligation: A general method for protein engineering, *Proc. Natl. Acad. Sci. USA*, 95, pp. 6705–6710 (1998).

Nikolova, et al., Semirational design of active tumor suppressor p53 DNA binding domain with enhanced stability, *Proc. Natl. Acad. Sci. USA*, 95, pp. 14675–14680 (1998).

Smith, et al., Automatic generation of primary sequence patterns from sets of related proteins, *Proc. Natl. Acad. Sci. USA*, 87, pp. 118–122 (1990).

Wallace, et al., Peptide ligation and semisynthesis, *Curr. Opin. Biotechnol.*, 6, pp. 403–410 (1995).

Wang, et al., Recombinant human bone morphogenetic protein induces bone formation, *Proc. Natl. Acad. Sci. USA*, 87, pp. 2220–2224 (1990).

* cited by examiner

*Primary Examiner*—Lorraine Spector
*Assistant Examiner*—Jegatheesan Seharaseyon
(74) *Attorney, Agent, or Firm*—Fish & Neave; James F. Haley, Jr.; Karen Mangasarian

(57) ABSTRACT

The invention provides modified proteins and DNAs of the TGF-β superfamily including modified morphogenic proteins. The proteins of the present invention display altered biological or biochemical attributes. Specifically, the modified proteins are designed through substitutions of amino acids in the finger 2 sub-domain or exchanges of all or part of the finger 2 sub-domain of one TGF-β superfamily member with the finger 2 sub-domain of another TGF-β superfamily member.

13 Claims, 12 Drawing Sheets

FIG. 1

| | | |
|---|---|---|
| OP-1 | CC A - - PTQLNAI SVLYFDDS- SNVI LKKYRNMVVRA | CGC H |
| BMP-5 | CC A - - PTKLNAI SVLYFDDS- SNVI LKKYRNMVVRS | CGC H |
| BMP-6 | CC A - - PTKLNAI SVLYFDDN- SNVI LKKYRNMVVRA | CGC H |
| OP-2 | CC A - - PTKLSATSVLYYDSS- NNVI LRKHRNMVVKA | CGC H |
| OP-3 | CC V - - PTELSAI SLLYYDRN- NNVI LRRERNMVVQA | CGC H |
| 60A | CC A - - PTRLGALPVLYHLND- ENVNLKKYRNMI VKS | CGC H |
| Vg-1 | CC V - - PTKMSPI SMLFYDNN- DNVVLRHYENMAVDE | CGC R |
| UNIVIN | CC A - - PTKLSGI SMLYFDNN- ENVVLRQYEDMVVEA | CGC R |
| BMP-2 | CC V - - PTELSAI SMLYLDEN- EKVVLKNYQDMVVEG | CGC R |
| BMP-4 | CC V - - PTELSAI SMLYLDEY- DKVVLKNYQEMVVEG | CGC R |
| GDF-5 | CC V - - PTRLSPI SI LFI DSA- NNVVYKQYEDMVVES | CGC R |
| GDF-6 | CC V - - PTKLTPI SI LYI DAG- NNVVYKQYEDMVVES | CGC R |
| GDF-7 | CC V - - PARLSPI SI LYI DAA- NNVVYKQYEDMVVEA | CGC R |
| CDMP-2 | CC V - - PTKLTPI SI LYI DAG- NNVVYNEYEEMVVES | CGC R |
| dpp | CC V - - PTQLDSVAMLYLNDQ- STVVLKNYQEMTVVG | CGC R |
| BMP-9 | CC V - - PTKLSPI SVLYKDDMGVPTLKYHYEGMSVAE | CGC R |
| DORSALIN | CC V - - PTKLDAI SI LYKDDAGVPTLI YNYEGMKVAE | CGC R |
| BMP-10 | CC V - - PTKLEPI SI LYLDKG- VVTYKFKYEGMAVSE | CGC R |
| GDF-3 | VC V - - PTKLSPI SMLYQDSD- KNVI LRHYEDMVVDE | CGC G |
| GDF-1 | CC V - - PERLSPI SVLFFDNE- DNVVLRHYEDMVVDE | CGC R |
| SCREW | CC V - - PTVLGAI TI LRYLNE- DI I DLTKYQKAVAKE | CGC H |
| BMP-3 | CC V - - PEKMSSLSI LFFDEN- KNVVLKVYPNMTVES | CAC R |
| NODAL | CC A - - PVKTKPLSMLYVDN- - GRVLLEHHKDMI VEE | CGC L |
| TGF-â2 | CC V - - SQDLEPLTI LYYI G- - KTPKI EQLSNMI VKS | CKC S |
| TGF-â3 | CC V - - PQDLEPLTI LYYVG- - RTPKVEQLSNMVVKS | CKC S |
| TGF-â4 | CC V - - PQTLDPLPI I YYVG- - RNVRVEQLSNMVVRA | CKC S |
| TGF-â1 | CC V - - PQALEPLPI VYYVG- - RKPKVEQLSNMI VRS | CKC S |
| TGF-â5 | CC V - - PDVLEPLPI I YYVG- - RTAKVEQLSNMVVRS | CNC S |
| GDF-9 | SC V - - PGKYSPLSVLTI EPD- GSI AYKEYEDMI ATR | CTC R |
| Inhibinà | CC A ALPGTMRPLHVRTTSDGGYSFKYETVPNLLTQH | CAC I |
| InhibinßA | CC V - - PTKLRPMSMLYYDDG- QNI I KKDI QNMI VEE | CGC S |
| InhibinßB | CC I - - PTKLSTMSMLYFDDE- YNI VKRDVPNMI VEE | CGC A |
| InhibinßC | CC V - - PTARRPLSLLYYDRD- SNI VKTDI PDMVVEA | CGC S |
| MIS | CC V - - PTATAGKLLI SLSE- - ERI SAHHVPNMVATE | CGC R |
| GDNF | CC R - - PI AFDDD- - LSFLD- - DNLVYHI LRKHSAKR | CGC I |
| BMP-11 | CC T - - PTKNSPI NMLYFNDK- QQI I YGKI PGMVVDR | CGC S |
| GDF-9 | SC V - - PGKYSPLSVLTI EPD- GSI AYKEYEDMI ATR | CTC R |

7-CYSTEINE DOMAIN OF OP-1

FINGER-1
TGTAAGAAGCACGAGCTGTATGTCAGCTTCCGAGACCTGGGCTGGCAGGACTGGATCATCGCGCCTGAAGGCTACGCCGCCTACTACTGTGAGGGG
 C  K  K  H  E  L  Y  V  S  F  R  D  L  G  W  Q  D  W  I  I  A  P  E  G  Y  A  A  Y  Y  C  E  G

HEEL
GAGTGTGCCTTCCCTCTGAACTCCTACATGAACGCCACCAACCACGCCATCGTGCAGACGCTGGTCCACTTCATCAACCCGGAAACGGTGCCCAAGCCCTGC
 E  C  A  F  P  L  N  S  Y  M  N  A  T  N  H  A  I  V  Q  T  L  V  H  F  I  N  P  E  T  V  P  K  P  C

FINGER-2
TGTGCCCCAACGCAGCTCAATGCCATCTCCGTCCTCTACTTCGATGACAGTTCCAACGTCATCCTGAAGAAATACAGAAACATGGTGGTCCGGGCCTGTGGCTGCCAC
 C  A  P  T  Q  L  N  A  I  S  V  L  Y  F  D  D  S  S  N  V  I  L  K  K  Y  R  N  M  V  V  R  A  C  G  C  H

FIG. 3A pH2475

```
         10         20         30         40         50         60         70         80         90        100        110        120
CCATGGCAGCCAACAAGCGTCTAAAAATCAAAATCAATAACCGCAATAATCAGCTCTCATCAGGACTCCTCCAGTCTCCAGTGTTGGAGATTATAACACAAGTGAGCAAAAACAAGCCTGTA
  M  A  A  N  K  R  L  K  N  Q  N  R  N  K  S  S  S  H  Q  D  S  S  R  M  S  S  V  G  D  Y  N  T  S  E  Q  K  Q  A  C
NcoI 130        140        150        160        170        180        190        200        210        220        230        240
AGAAGCAGAACTCTATGTGAGCTTCCGGGATCTGGGATGGCAGGACTGGATTATAGCACCAGAAGGATACGCTGCATTTTATTGTGATGGAGAATGTTCTTTTCCACTTAACGCCCATA
  K  K  H  E  L  Y  V  S  F  R  D  L  G  W  Q  D  W  I  I  A  P  E  G  Y  A  A  F  Y  C  D  G  E  C  S  F  P  L  N  A  H
                                                                                                                       NdeI 250        260        270        280        290        300        310        320        330        340        350        360
TGAATGCCACCAACCACGCTATAGTTCAGACTCTGGTTCATCTGATGTTCCTGACCACGTACCAAAGCCTTGTTGTGCTCCAACCAAATTAAATGCCATCTCTGTTCTGTACTTTGATG
  M  N  A  T  N  H  A  I  V  Q  T  L  V  H  L  M  F  P  D  H  V  P  K  P  C  C  A  P  T  K  L  N  A  I  S  V  L  Y  F  D
             AlwNI 370        380        390        400        410        420        430        440
ACAGCTCCAACGTCATCCTGAAGAAATACGAAGACATGGTGGTCGAAGCTTGTGGCTGCAGATAGCTCCTCCGAGAATTC
  D  S  S  N  V  I  L  K  K  Y  E  D  M  V  V  E  A  C  G  C  R  *
                             DrdI            HindIII        PstI              EcoRI

ALTERATIONS:                                ^              ^    ^        ^

ORIGINAL BMP-5 SEQUENCE:       AGAAATATGGTAGTACGCTCATGTGGCTGCCACTAA
                                 R  N  M  V  V  R  S  C  G  C  H  *
                               ^  ^                       ^    ^
```

FIG. 3B

OP-1 CHIMERICS WITH CDMP-2 OR WITH BMP-2

| PARENTAL MOLECULES: | | REFOLDING ACTIVITY (CELL BASED) | |
|---|---|---|---|
| OP-1 (FINGER1 HEEL FINGER2) h | | (−) | +++ (*) |
| BMP-2 r | | +++ | +++ |
| CDMP-2 r | | ++++ | +/− |

REPLACING FINGER-1 OR HEEL:

| H2383 r | +/− | N/A |
|---|---|---|
| H2362 r | + | N/A |
| H2360 r | + | N/A |
| H2331 r | + | N/A |

REPLACING FINGER-2 OR HEEL:

| H2389 r | +++ | +++ |
|---|---|---|
| H2471 r | +++ | +++ |
| H2388 r | +++ | +/− |
| H2410 r | +++ | +++ |
| H2429 r | +/− | N/A |

CHANGING PATCHES OF RESIDUES:

| H2381 r | +++ | N/A |
|---|---|---|
| H2390 r | + | N/A |
| H2396 r | + | N/A |
| H2421 r | +/− | N/A |

PAIRED CHANGES IN FINGER-2:

| H2418 r | +++ | ++ |
|---|---|---|
| H2420 r | ++++ | +/− |

*FIG. 4A*

OP-1 MUTANTS WITH C-TERMINAL ARGININE INSTEAD OF HISTIDINE:

| | | | |
|---|---|---|---|
| H2247 | r | + | +++ |
| H2233    25,26,30 ed e r | | + | +++ |

BALANCING OF CHARGED RESIDUES IN FINGER-2 OF OP-1 MUTANTS:

| | | | |
|---|---|---|---|
| H2406   1,4,6,7 vktp r | | +/− | N/A |
| H2443   1,4,6,7   25,26 vktp ed r | | +++ | ++ |
| H2447   1,4,6   25,26,30 ves ede r | | +++ | ++ |
| H2433   4 k r | | +/− | N/A |
| H2456   4,6   25,26,30 es ede r | | +++ | +++ |

*FIG. 4B*

CORRELATION OF REFOLDING EFFICIENCY AND CHARGED AMINO ACIDS
IN THE TGF-β (SEVEN CYSTEINE) DOMAIN

| PROTEIN | FINGER-1 | CXGXC | HEEL | FINGER-2 | CXCX C-TERM | TOTAL OF CHARGED RESIDUES (+), (-) = TOTAL | NEGATIVE CHARGES, FINGER-2 | NET CHARGES, FINGER-2 | REFOLDING EFFICIENCY |
|---|---|---|---|---|---|---|---|---|---|
| OP-1 | 3+, 4- | 2- | 1+, 1- | 4+, 2- | 0 | 8+, 9- = 17 | 2- | 2+ | +/- |
| H2247 | 3+, 4- | 2- | 1+, 1- | 4+, 2- | 1+ | 9+, 9- = 18 | 2- | 2+ | + |
| H2447 | 3+, 4- | 2- | 1+, 1- | 2+, 6- | 1+ | 7+, 12- = 19 | 6- | 4- | +++ |
| BMP-3 | 4+, 4- | 0 | 3+, 1- | 3+, 4- | 1+ | 11+, 9- = 20 | 4- | 1- | +++ |
| BMP-2 | 2+, 3- | 1- | 2+, 1- | 2+, 6- | 1+ | 7+, 11- = 18 | 6- | 4- | +++ |
| GDF-5 | 3+, 5- | 1- | 1+, 4- | 2+, 4- | 1+ | 6+, 14- = 20 | 4- | 2- | +++ |
| CDMP-2 | 3+, 5- | 1- | 1+, 3- | 2+, 4- | 1+ | 6+, 13- = 19 | 4- | 2- | +++ |
| GDNF | 2+, 4- | 0 | 6+, 4- | 5+, 5- | 0 | 13+, 13- = 26 | 5- | 0 | +++ |
| TGF-β1 | 5+, 3- | 0 | 1+, 1- | 5+, 2- | 1+ | 11+, 6- = 17 | 2- | 3+ | +/- |
| TGF-β2 | 5+, 3- | 0 | 1+, 2- | 4+, 3- | 1+ | 10+, 8- = 18 | 3- | 1+ | +/- |

FIG. 5

```
TGF-β SUBGROUP +----------------+----------+----------------+-----------+--------+
       TGF-β1: |C|C V R Q L Y I D|F R K D L|G W K - W I H E P K|G Y H A N F|C L G P C|
       TGF-β2: |C|C L R P L Y I D|F K R D L|G W K - W I H E P K|G Y N A N F|C A G A C|
       TGF-β3: |C|C V R P L Y I D|F R Q D L|G W K - W V H E P K|G Y Y A N F|C S G P C|
       TGF-β4: |C|C V R P L Y I D|F R K D L|Q W K - W I H E P K|G Y M A N F|C M G P C|
       TGF-β5: |C|C V K P L Y I N|F R K D L|G W K - W I H E P K|G Y E A N Y|C L G N C|
      PATTERN: |C|C V R P L Y I D|F R n D L|G W K - W I H E P K|G Y X A N F|C X G j C|
Vg/dpp SUBGROUP+----------------+----------+----------------+-----------+--------+
          dpp: |C|R R H S L Y V D|F S - D V|G W D D W I V A P L|G Y D A Y Y|C H G K C|
         Vg-1: |C|K K R H L Y V E|F K - D V|G W Q N W V I A P Q|G Y M A N Y|C Y G E C|
        Vgr-1: |C|K K H E L Y V S|F Q - D L|G W Q D W I I A P K|G Y A A N Y|C D G E C|
          60A: |C|Q M Q T L Y I D|F K - D L|G W H D W I I A P E|G Y G A F Y|C S G E C|
       BMP-2A: |C|K R H P L Y V D|F S - D V|G W N D W I V A P P|G Y H A F Y|C H G E C|
     DORSALIN: |C|R R T S L H V N|F K - E I|G W D S W I I A P K|D Y E A F E|C K G G C|
  BMP-2B/BMP-4:|C|R R H S L Y V D|F S - D V|G W N D W I V A P P|G Y Q A F Y|C H G D C|
        BMP-3: |C|A R R Y L Y V D|F A - D I|G W S E W I I S P K|S F D A Y Y|C S G A C|
        BMP-5: |C|K K H E L K V S|F R - D L|G W Q D W I I A P E|G Y A A F Y|C D G E C|
        BMP-6: |C|R K H E L Y V S|F Q - D L|G W Q D W I I A P K|G Y A A N Y|C D G E C|
     OP-1/BMP-7:|C|K K H E L Y V S|F R - D L|G W Q D W I I A P E|G Y A A Y Y|C E G E C|
         OP-2: |C|R R H E L Y V S|F Q - D L|G W L D W V I A P Q|G Y S A Y Y|C E G E C|
         OP-3: |C|R R H E L Y V S|F R - D L|G W L D S V I A P Q|G Y S A Y Y|C A G E C|
      PATTERN: |C|n n r r L Y V r|F r - D c|G W r D W I I A P p|G Y X A d Y|C r G k C|
GDF SUBGROUP-+--+-------------+----------+----------------+-----------+--------+
        GDF-1: |C|R T R R L H V S|F R - E V|G W H R W V I A P R|G F L A N F|C Q G T C|
        GDF-3: |C|H R H Q L F I N|F Q - D L|G W H K W V I A P K|G F M A N Y|C H G E C|
        GDF-9: |C|E L H D F R L S|F S - Q L|K W D N W I V A P H|R Y N P R Y|C K G D C|
      PATTERN: |C|r X r r f X c r|F r - r c|X W r r W a a A P r|X d X j r d|C r G r C|
INHIBIN SUBGROUP----------------+----------+----------------+-----------+--------+
      INHIBINα: |C|H R V A L N I S|F Q - E L|G W E R W I V Y P P|S F I F H Y|C H G G C|
     INHIBINβA: |C|C K K Q F F V S|F K - D I|G W N D W I I A P S|G Y H A N Y|C E G E C|
     INHIBINβB: |C|C R Q Q F F I D|F R - L I|G W N D W I I A P T|G Y Y G N Y|C E G S C|
      PATTERN: |C|X n X X f X a r|F P - X c|G W m r W I a X P j|j d X X r Y|C r G X C|
              +--+-------------+----------+----------------+-----------+--------+
               |1|         10   |     20   |          30   |           |
               | |   BETA     | HELIX  |   LOOP        |   BETA    | RING   |
               |K|_____FINGER 1_____|KNOT_A|
```

*FIG. 6A*

```
TGF-ß SUBGROUP----------------------------+-------------------------+--------+-+
        TGF-ß1: |V - - P Q A L E P L P I V Y|Y V G - - R K P|K V E Q L S N M I V R S|C K C|S|
        TGF-ß2: |V - - S Q D L E P L T I L Y|Y I G - - K T P|K I E Q L S N M I V K S|C K C|S|
        TGF-ß3: |V - - P Q D L E P L T I L Y|Y V G - - R T P|K V E Q L S N M V V K S|C K C|S|
        TGF-ß4: |V - - P Q T L D P L P I I Y|Y V G - - R N V|R V E Q L S N M V V R A|C K C|S|
        TGF-ß5: |V - - P D V L E P L P I I Y|Y V G - - R T A|K V E Q L S N M V V R S|C N C|S|
       PATTERN: |V - - P Q X L E P L j I c Y|Y V G - - R r j|K V E Q L S N M a V n S|C K C|S|
Vg/dpp SUBGROUP---------------------------+-------------------------+--------+-+
           dpp: |V - - P T Q L D S V A M L Y|L N D Q - S T V|V L K N Y Q E M T V V G|C G C|R|
          Vg-1: |V - - P T K M S P I S M L F|Y D N N - D N V|V L R H Y E N M A V D E|C G C|R|
         Vgr-1: |A - - P T K L N A I S V L Y|F D D N - S N V|I L K K Y R N M V V R A|C G C|H|
           60A: |A - - P T R L G A L P V L Y|H L N D - E N V|N L K K Y R N M I V K S|C G C|H|
        BMP-2A: |V - - P T E L S A I S M L Y|L D E N - E K V|V L K N Y Q D M V V E G|C G C|R|
      DORSALIN: |V - - P T K L D A I S I L Y|K D D A G V P T|L I Y N Y E G M K V A E|C G C|R|
    BMP-2B/BMP-4: |V - - P T E L S A I S M L Y|L D E Y - D K V|V L K N Y Q E M V V E G|C G C|R|
         BMP-3: |V - - P E K M S S L S I L F|F D E N - K N V|V L K V Y P N M T V E S|C A C|R|
         BMP-5: |A - - P T K L N A I S V L Y|F D D S - S N V|I L K K Y R N M V V R S|C G C|H|
         BMP-6: |A - - P T K L N A I S V L Y|F D D N - S N V|I L K K Y R N M V V R A|C G C|H|
      OP-1/BMP-7: |A - - P T Q L N A I S V L Y|F D D S - S N V|I L K K Y R N M V V R A|C G C|H|
          OP-2: |A - - P T K L S A T S V L Y|Y D S S - N N V|I L R K H R N M V V K A|C G C|H|
          OP-3: |V - - P T E L S A I S L L Y|Y D R N - N N V|I L R R E R N M V V Q A|C G C|H|
       PATTERN: |X - - P T p L r A a S c L Y|f D m r z r r V|a L n r Y p l M X V p j|C G C|r|
GDF SUBGROUP-+---------------------------+-------------------------+--------+-+
         GDF-1: |V - - P E R L S P I S V L F|F D N S - D N V|V L R H Y E D M V V D E|C G C|R|
         GDF-3: |V - - P T K L S P I S M L Y|Q D S D - K N V|I L R H Y E D M V V D E|C G C|G|
         GDF-9: |V - - P G K Y S P L S V L T|I E P D - G S I|A Y K E Y E D M I A T R|C T C|R|
       PATTERN: |V - - P X n f S P c S c L X|X k X r - X r a|X f n r Y E D M a X r p|C j C|X|
INHIBIN SUBGROUP-------------------------+-------------------------+--------+-+
      INHIBIN α: |A A L P G T M R P L H V R T|T S D G G Y S F|K Y E T V P N L L T Q H|C A C|I|
     INHIBIN ßA: |V - - P T K L R P M S M L Y|Y D D G - Q N I|I K K D I Q N M I V E E|C G C|S|
     INHIBIN ßB: |I - - P T K L S T M S M L Y|F D D E - Y N I|V K R D V P N M I V E E|C G C|A|
       PATTERN: |X z z P j r b r j b r c X X|X r D X z X r f|X X p r a X N b c X o r|C h C|X|
              +---------------------------+-------------------------+--------+-+
              |      80           | 90              | 100           |110  | |
              |     BETA          | LOOP            |  BETA         |RING | |
              |                   FINGER_2                          |KNOT2|C|
              |_____|
```

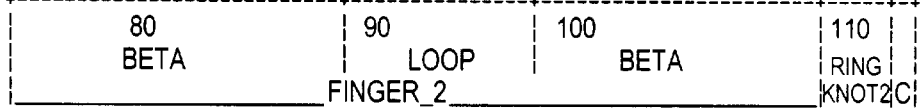

*FIG. 6C*

MUTATIONS OF THE C-TERMINAL PORTION OF TGF-β SUPERFAMILY PROTEINS

The present utility application is based on provisional patent application No. 60/103,418, filed on Oct. 7, 1998, the entire contents of which is incorporated by reference herein; and the instant application is related to utility applications Ser. Nos. 09/375,333 and 09/374,936, filed on even date herewith, also based on the above-identified provisional application, the disclosures of which are incorporated by reference herein.

FIELD OF THE INVENTION

The invention relates to modified proteins, and DNAs encoding the same, which are biosynthetic, chemosynthetic or recombinant constructs derived from the TGF-β superfamily of structurally related proteins, including modified morphogenic proteins.

BACKGROUND OF THE INVENTION

The TGF-β superfamily includes five distinct forms of TGF-β (Sporn and Roberts (1990) in *Peptide Growth Factors and Their Receptors*, Sporn and Roberts, eds., Springer-Verlag: Berlin pp. 419–472), as well as the differentiation factors Vg-1 (Weeks and Melton (1987) *Cell* 51: 861–867), DPP-C polypeptide (Padgett et al. (1987) *Nature* 325: 81–84), the hormones activin and inhibin (Mason et al. (1985) *Nature* 318: 659–663; Mason et al. (1987) *Growth Factors* 1: 77–88), the Mullerian-inhibiting substance, MIS (Cate et al. (1986) *Cell* 45:685–698), osteogenic and morphogenic proteins OP-1 (PCT/US90/05903), OP-2 (PCT/US91/07654), OP-3 (PCT/WO94/10202), the BMPs, (see U.S. Pat. Nos. 4,877,864; 5,141,905; 5,013,649; 5,116,738; 5,108,922; 5,106,748; and 5,155,058), the developmentally regulated protein Vgr-1 (Lyons et al. (1989) *Proc. Natl. Acad. Sci. USA* 86: 4554–4558) and the growth/differentiation factors GDF-1, GDF-3, GDF-9 and dorsalin-1 (McPherron et al. (1993) *J. Biol. Chem.* 268: 3444–3449; Basler et al. (1993) *Cell* 73: 687–702), to name but a few.

The proteins of the TGF-β superfamily are disulfide-linked homo- or heterodimers that are expressed as large precursor polypeptide chains containing a hydrophobic signal sequence, a long and relatively poorly conserved N-terminal pro region sequence of several hundred amino acids, a cleavage site, a mature domain comprising an N-terminal region that varies among the family members and a highly conserved C-terminal region. This C-terminal region, present in the processed mature proteins of all known family members, contains approximately 100 amino acids with a characteristic cysteine motif having a conserved six or seven cysteine skeleton. Although the position of the cleavage site between the mature and pro regions varies among the family members, the cysteine pattern of the C-terminus of all of the proteins is in the identical format, ending in the sequence Cys-X-Cys-X (Sporn and Roberts (1990), supra).

A unifying feature of the biology of the proteins of the TGF-β superfamily is their ability to regulate developmental processes, including endochondral bone morphogenesis. These structurally related proteins have been identified as being involved in a variety of developmental events. For example, TGF-β and the polypeptides of the inhibin/activin group appear to play a role in the regulation of cell growth and differentiation. MIS causes regression of the Mullerian duct in development of the mammalian male embryo, and dpp, the gene product of the Drosophila decapentaplegic complex, is required for appropriate dorsal-ventral specification. Similarly, Vg-1 is involved in mesoderm induction in Xenopus, and Vgr-1 has been identified in a variety of developing murine tissues. Regarding bone formation, proteins in the TGF-β superfamily, for example OP-1 and a subset of other proteins identified as BMPs (bone morphogenic proteins) play the major role. OP-1 (BMP-7) and other osteogenic proteins have been produced using recombinant techniques (U.S. Pat. No. 5,011,691 and PCT Application No. US 90/05903) and shown to be able to induce formation of true endochondral bone in vivo. The osteogenic proteins generally are classified in the art as a subgroup of the TGF-β superfamily of growth factors (Hogan (1996), *Genes & Development*, 10:1580–1594).

Recently certain members of this same family of proteins have been recognized to be morphogenic, i.e., capable of inducing the developmental cascade of tissue morphogenesis in a mature mammal (See PCT Application No. US 92/01968). In particular, these morphogens are capable of inducing the proliferation of uncommitted progenitor cells, and inducing the differentiation of these stimulated progenitor cells in a tissue-specific manner under appropriate environmental conditions. In addition, the morphogens are capable of supporting the growth and maintenance of these differentiated cells. These morphogenic activities allow the proteins to initiate and maintain the developmental cascade of tissue morphogenesis in an appropriate, morphogenically permissive environment, stimulating stem cells to proliferate and differentiate in a tissue-specific manner, and inducing the progression of events that culminate in new tissue formation. These morphogenic activities also allow the proteins to induce the "redifferentation" of cells previously stimulated to stray from their differentiation path. Under appropriate environmental conditions it is anticipated that these morphogens also may stimulate the "redifferentiation" of committed cells.

Members of this morphogenic class of proteins include the mammalian osteogenic protein-1 (OP-1, also known as BMP-7, and the Drosophila homolog 60A), osteogenic protein-2 (OP-2, also known as BMP-8), osteogenic protein-3 (OP-3), BMP-2 (also known as BMP-2A or CBMP-2A, and the Drosophila homolog DPP), BMP-3, BMP-4 (also known as BMP-2B or CBMP-2B), BMP-5, BMP-6 and its murine homolog Vgr-1, BMP-9, BMP-10, BMP-11, BMP-12, GDF-3 (also known as Vgr2), GDF-8, GDF-9, GDF-10, GDF-11, GDF-12, BMP-13, BMP-14, BMP-15, GDF-5 (also known as CDMP-1 or MP52), GDF-6 (also known as CDMP-2 or BMP-13), GDF-7 (also known as CDMP-3 or BMP-12), the Xenopus homolog Vg1 and NODAL, UNWIN, SCREW, ADMP, and NEURAL, to name but a few.

By way of illustration using exemplary family members, the tertiary and quaternary structure of both TGF-β2 and OP-1 have been determined. Although TGF-β2 and OP-1 exhibit only about 35% amino acid identity in their respective amino acid sequences the tertiary and quaternary structures of both molecules are strikingly similar. Both TGF-β2 and OP-1 are dimeric in nature and have a unique folding pattern involving six of the seven C-terminal cysteine residues. In each subunit four cysteines bond to generate an eight residue ring, and two additional cysteine residues form a disulfide bond that passes through the ring to form a knot-like structure. With a numbering scheme beginning with the most N-terminal cysteine of the 7 conserved cysteine residues assigned number 1, the 2nd and 6th cysteine residues bond to close one side of the eight residue ring while the 3rd and 7th cysteine residues close the other side. The 1st and 5th conserved cysteine residues bond through the center of the ring to form the core of the knot. The 4th cysteine forms an interchain disulfide bond with the corresponding residue in the other subunit.

The TGF-β2 and OP-1 monomer subunits comprise three major structural elements and an N-terminal region. The structural elements are made up of regions of contiguous polypeptide chain that possess over 50% secondary structure of the following types: (1) loop, (2) α-helix and (3) β-sheet. Furthermore, in these regions the N-terminal and C-terminal strands are not more than 7 Å apart. The residues between the 1st and 2nd conserved cysteines form a structural region characterized by an anti-parallel β-sheet finger, referred to herein as the finger 1 region (F1). Similarly the residues between the 5th and 6th conserved cysteines also form an anti-parallel β-sheet finger, referred to herein as the finger 2 region or sub-domain (f2). A β-sheet finger is a single amino acid chain, comprising β-strand that folds back on itself by means of a β-turn or some larger loop so that the entering and exiting strands forth one or more anti-parallel β-sheet structures. The third major structural region, involving the residues between the 3rd and 4th conserved cysteines is characterized by a three turn α-helix referred to herein as the heel region (H). In the dimeric forms of both TGF-β2 and OP-1, the subunits are oriented such that the heel region of one subunit contacts the finger regions of the other subunit with the knot regions of the connected subunits forming the core of the molecule. The 4th cysteine forms a disulfide bridge with its counterpart on the second chain thereby equivalently linking the chains at the center of the palms. The dimer thus formed is an ellipsoidal (cigar shaped) molecule when viewed from the top looking down the two-fold axis of symmetry between the subunits.

Whether naturally-occurring, or recombinantly or synthetically prepared, true morphogens within the TGF-β superfamily, such as osteogenic proteins, can induce recruitment and stimulation of progenitor cells, thereby inducing their differentiation, e.g., into chondrocytes and osteoblasts, and further inducing differentiation of intermediate cartilage, vascularization, bone formation, remodeling, and, finally, marrow differentiation. Numerous practitioners have demonstrated the ability of osteogenic proteins, when admixed with either naturally-sourced matrix materials such as collagen or synthetically-prepared polymeric matrix materials, to induce true bone formation, including endochondral bone formation, under conditions where true replacement bone would not otherwise occur. For example, when combined with a matrix material, these osteogenic proteins induce formation of new bone in large segmental bone defects, calvarial defects, spinal fusions, and fractures, to name but a few.

Bacterial and other prokaryotic expression systems are relied on in the art as preferred means for generating both native and biosynthetic or recombinant proteins. Further, total chemical synthesis is an emerging possibility for producing small proteins. Prokaryotic systems such as *E. coli* are useful for producing commercial quantities of proteins, as well as for evaluating biological and chemical properties of naturally occurring or synthetically prepared mutants and analogs. Typically, an over-expressed eukaryotic protein aggregates into an insoluble intracellular precipitate ("inclusion body") in the prokaryote host cell. The aggregated protein is then collected from the inclusion bodies, solubilized using one or more standard denaturing agents, and then allowed, or induced, to refold into a functional state. Chemically synthesized proteins would also require proper refolding.

Optimal refolding requires proper formation of any disulfide bonds to form and stabilize a biologically active protein structure. However, not all naturally-occurring proteins when solubilized readily refold. Despite careful manipulation of the chemistries for refolding, the yields of optimally folded, stable and/or biologically active protein remain low. Many of the aforementioned proteins, including BMPs, fall into the category of poor refolder proteins. For example, while some members of the BMP protein family can be folded relatively efficiently in vitro as, for example, when produced in *E. coli* or other prokaryotic hosts, many others, including BMP-5, BMP-6, and BMP-7, are not. See, e.g., EP 0433225 and U.S. Pat. No. 5,399,677, U.S. Pat. No. 5,756,308, and U.S. Pat. No. 5,804,416.

A need remains for improved means for designing and successfully producing recombinant, chemosynthetic and/or biosynthetic members of the TGF-β superfamily of proteins, including morphogenic proteins.

SUMMARY OF THE INVENTION

The present invention provides modified proteins, and DNAs encoding the same, of the TGF-β superfamily including morphogenic proteins. As used herein, the terms "modified TGF-β superfamily", "mutant TGF-β superfamily", "mutant protein", "mutant construct", and "mutant" refer to any TGF-β superfamily member synthetic construct wherein specific amino acids have been substituted by other amino acids or where any or all of a finger 2 sub-domain of one TGF-β superfamily member is replaced by any or all of a finger 2 sub-domain of another TGF-β superfamily member. Also contemplated herein, mutant proteins comprise recombinant and/or biosynthetic and/or chemosynthetic proteins. Additionally, mutant proteins of the invention have altered refolding attributes relative to naturally occurring proteins. Mutant proteins of the invention can have altered stability, specific activity, solubility, bioactivity and/or biospecificity attributes, and are useful for tissue-specific targeting.

In one embodiment, the invention provides synthetic mutant proteins that improve the refolding properties of the native "poor refolder" proteins. As used herein, a "poor refolder" protein means any protein that, when induced to refold under typically suitable refolding conditions, yields less than about 1% optimally refolded material (see below). Specifically, poor refolders are transformed to good refolders by specific amino acid sequence changes within the poor refolder's C-terminal finger 2 sub-domain. The poor refolder protein's folding capabilities also are enhanced by increasing the number of hydrophilic residues, particularly acidic (negatively charged) residues, in the protein's finger 2 sub-domain.

Increasing the number of acidic residues in the base region of the finger 2 sub-domain improves the refolding properties of the substituted sequence as compared with the refolding properties of the unsubstituted parent sequence. The poor refolder protein's folding capabilities also are enhanced by increasing the number of hydroxyl-group carrying polar residues in the protein's finger 2 sub-domain, particularly in the base region of the finger 2 sub-domain. Further, it has been discovered that individual sub-domains of the C-terminal active region of a TGF-β superfamily member protein can be exchanged to acquire a desired biological or biochemical property.

In a preferred embodiment, pail or all of the finger 2 base region of a poor refolder is exchanged for the finger 2 base region of a good refolder to improve the folding properties of the parent protein without substantially affecting the biological specificity of the TGF-β superfamily member protein. It is anticipated that the receptor binding specificity of a given TGF-β superfamily member protein is altered by exchanging the finger 2 tip region of one TGF-β superfamily member protein with that of a different TGF-β superfamily member protein without substantially affecting the folding properties of the parent protein.

As a result of these discoveries, means are now available for predicting and designing de novo TGF-β superfamily member mutants having altered attributes, including altered folding capabilities, altered solubility, altered stability, altered isoelectric points, altered surface or carrier binding properties, and/or altered biological activities and specificities, as desired. The invention also provides means for easily and quickly evaluating biological and/or biochemical attributes of chimeric constructs, including mapping epitopes. In particular, candidates are constructed with particular specific amino acid sequences in the finger 2 sub-domain, thereby allowing expression of the candidate sequence in a prokaryotic host, such as *E. coli*, followed by refolding in vitro.

As used herein, a "poor refolder" protein means any protein that, when induced to refold under typically suitable refolding conditions, yields less than about 1% optimally refolded material, as measured using a standard protocol. As contemplated herein, "typically suitable refolding conditions" are conditions under which proteins can be refolded to the extent required to confer functionality. One skilled in the an will recognize that at least Section I.B.1.(c) and Example 3 disclose non-limiting examples of such refolding conditions. Structural parameters relevant to the compositions and methods of the instant invention include one or more disulfide bridges properly distributed throughout the dimeric protein's structure and which require a reduction-oxidation ("redox") reaction step to yield a folded structure. Redox reactions typically occur at neutral pHs. Accordingly, as used herein, "suitable refolding conditions" include a redox reaction step at a substantially neutral pH, i.e., in the range of about pH 5.0–10.0, typically in the range of about pH 6.0–9.0, and preferably under physiologically compatible conditions. The skilled artisan will appreciate and recognize optimal conditions for success.

In one preferred embodiment, the invention provides recombinant, chemosynthetic or biosynthetic TGF-β superfamily member proteins having altered refolding properties under neutral or otherwise physiologically-compatible conditions. By way of example only, the recombinant, chemosynthetic or biosynthetic proteins of the invention have altered refolding properties at a pH in the range of about 5.0–10.0, preferably in the range of about 6.0–9.0, more preferably in the range of about 7.0–8.5, including in the range of about pH 7.5–8.5.

In another embodiment, the invention provides recombinant, chemosynthetic or biosynthetic TGF-β superfamily member proteins having altered solubility attributes under neutral or otherwise physiologically compatible conditions. In one embodiment, the proteins of the invention have altered solubility at a pH in the range of about 5.0–10.0, preferably in the range of about 6.0–9.0, more preferably in the range of about 6.0–8.5, including in the range of about pH 7.0–7.5. In another embodiment, the stability of a protein is altered by the modifications and manipulations disclosed herein. "Altered" is intended to mean different from the native protein's attribute(s), and includes embodiments which can be more stable or less stable, and/or more soluble or less soluble, etc.

In still another embodiment, the invention provides recombinant, chemosynthetic or biosynthetic TGF-β superfamily member proteins competent to refold under physiologically compatible conditions and having altered isoelectric points as compared with the native protein. In another embodiment, the invention provides recombinant, chemosynthetic or biosynthetic TGF-β superfamily member proteins having altered refolding properties as compared with the native protein, and wherein the mutant proteins also have, for example, altered receptor binding specificity, altered stability, altered solubility and/or biological activity.

In another aspect, the invention provides recombinant, chemosynthetic or biosynthetic TGF-β superfamily member proteins having improved refolding properties as compared with the parent protein, and, in certain preferred embodiments, wherein at least one residue, preferably two, more preferably three or more residues, in the neck or base region of a poor refolder protein's finger 2 sub-domain is replaced with an acidic residue. In certain other embodiments more than five residues are replaced. In one embodiment the substituting acidic residue is Glu or Asp. In another preferred embodiment, the acidic residue replaces a basic residue or an amide group-carrying hydrophilic residue in the base region. In still another preferred embodiment the parent protein is any one of OP-1 BMP-5, BMP-6, OP-2, OP-3 or 60-A, including chimerics, heterodimers and amino acid variants thereof, and the substitution with an acidic residue is made at least at one of the following positions 4(Q), 6(N), 25(R), 26(N), 30(R), and potentially also at 22(K), 23(K) and 31(A). Counting from the first residue following the cysteine doublet in the C-terminal domain of OP-1. (See e.g., FIG. 1). In another embodiment the parent protein is any one of NODAL, TGF-β1, TGF-β2, TGF-β3, TGF-β4 and TGF-β5, and the substitution is made at one or more of the following positions, 4(K, D, T, A, V), 6 (K, E, D), 24 (K, S), 25 (D, N), 29 (E, K, R) and possibly 30 (E, S, A).

In another aspect, the invention provides recombinant, chemosynthetic or biosynthetic TGF-β superfamily member proteins having improved refolding properties as compared with the parent protein, and, in certain preferred embodiments, wherein at least one residue, preferably two, more preferably three or more residues, in the neck or base region of a poor refolder protein's finger 2 sub-domain is replaced with a hydroxyl group-carrying polar residue. In certain other embodiments more than five residues are replaced. In one embodiment the substituting polar residue is Ser or Thr. In another preferred embodiment, the substituting residue replaces a basic residue or an amide group-carrying hydrophilic residue in the base region. In still another preferred embodiment the parent protein is any one of OP-1 BMP-5, BMP-6, OP-2, OP-3 or 60-A, including chimerics, heterodimers and amino acid variants thereof, and the substitution with an acidic residue is made at least at one of the following positions: 4, 6, 25, 26, 30, potentially 22, 23, and 31 from the first residue following the cysteine doublet in the C-terminal domain. (See e.g., FIG. 1). In another embodiment the parent protein is any one of NODAL, TGF-01, TGF-β2, TGF-β3, TGF-β4 and TGF-β5, and the substitution is made at one or more of the positions, 4, 6, 24, 25, 29 and potentially 30.

In another embodiment the substitution of residues with an acidic residue and/or hydroxyl group-carrying polar residue occurs at least at one of the following positions in OP-1 (SEQ ID NO: 39): 400, 402, 405, 421, 422, 426, corresponding to residues 4, 6, 9, 25, 26 and 30, respectively, when counting from the first residue following the conserved cysteine doublet in the C-terminal active domain (see FIG. 1).

In another aspect, the invention provides recombinant, chemosynthetic, or biosynthetic TGF-β superfamily member proteins, including heterodimers and chimeras, wherein the C-terminal residue has been replaced with any one of the amino acid residues: arginne, serene, isoleucine, leucine or alanine and having improved refolding properties as compared to the unsubstituted parent TGF-β superfamily member protein sequence. In one preferred embodiment, the TGF-β superfamily member is OP-1. In another embodiment the TGF-β superfamily member is any one of BMP-5, BMP-6, 60-A, or OP-2. In still another embodiment, the TGF-β superfamily member is any of GDF-3, SCREW or NODAL. In one preferred embodiment, the substituting residue is arginine. In another preferred embodiment the C-terminal residue in the parent sequence that is replaced is histidine. In another preferred embodiment, the parent protein is any poor refolder protein included in the list of any one of OP-1, BMP-5, BMP-6, OP-2, OP-3, 60-A, NODAL, GDF-3 or SCREW, chimerics and/or amino acid variants thereof, and the substituting C-terminal residue is arginine. In another embodiment, the parent protein is any poor refolder protein included in the list of TGF-β1, TGF-β2, TGF-β3, TGF-β3 and TGF-β5, including chimeras and/or amino acid variants thereof, and the substituting C-terminal residue is arginine. In one embodiment these C-terminally substituted proteins further include one or more amino acid residue substitutions in the finger 2 sub-domain to increase the number of acidic (negatively charged) residues in this region to at least 3, preferably 4, more preferably 5. In a preferred embodiment, the acidic residue substitution is made in the neck or base region of the finger 2 sub-domain. In one embodiment the substituting acidic residue is Asp or Glu. In still another embodiment, the acidic residues replace hydrophilic residues, particularly amide groups-carrying and/or positively charged residues in this region. In still another embodiment, these replaced residues include: Asn, Gln, His, Arg and Lys. In another embodiment, the C-terminally substituted proteins further include one or more amino acid residue substitutions in the finger 2 sub-domain to reduce the number of amide group carrying residues and/or positively charged residues in this region. In one embodiment, the substituted finger 2 sub-domain has less than five positively charged residues, preferably 4 or less, more preferably 3 or less, positively charged residues in the base region of finger 2. In still another embodiment, the C-terminally substituted proteins further include one or more amino acid residue substitutions in the finger 2 sub-domain to increase the number of hydroxyl group carrying residues in this region. In one embodiment the substituting polar residue is Ser or Thr. In another embodiment the substituting residue replaces a basic or amide group-carrying residue.

Modified proteins of the invention can be used in conjunction with a biocompatible matrix such as collagen, hydroxyapatite, ceramics or carboxymethylcellulose, or other suitable matrix material. Such combinations are particularly useful in methods for regenerating bone, cartilage and/or other non-mineralized skeletal or connective tissues such as, but not limited to, ligament, tendon, muscle, articular cartilage, fibrocartilage, joint capsule, menisci, intervertabral discs, synovial membrane tissue, and fasica to name but a few. See e.g. U.S. Pat. Nos. 5,496,552, 5,674,292, 5,840,325 and U.S. Ser. No. 08/253,398, soon-to-issue as U.S. Pat. No. 5,906,827, the disclosures of which are incorporated by reference herein; also incorporated by reference herein are co-pending U.S. Ser. Nos. 08/459,129 and 08/458,811 each filed on Jun. 2, 1995. The instant application contemplates that the binding and/or adherence properties to such matrix materials can be altered using the specific mutations and techniques disclosed herein.

In another embodiment, the invention provides a method for folding those native TGF-β superfamily proteins which are poor refolders, such as BMP homodimers and heterodimers, as well as for folding the mutant proteins of the present invention under physiologically compatible and/or neutral pH conditions. In one preferred embodiment, the method comprises the steps of providing one or more solubilized substituted TGF-β superfamily member mutants of the invention, exposing the solubilized mutant to a redox reaction in a suitable refolding buffer, and allowing the protein subunits to refold into homodimers and/or heterodimers, as desired. In another embodiment, the redox reaction system can utilize oxidized and reduced forms of glulathione, DTT, β-mercaptoethanol, β-mercaptomethanol, cystine and cystamine. In another embodiment the redox reaction system relies on air oxidation, preferably in the presence of a metal catalyst, such as copper. In still another embodiment, ratios of reluctant to oxidant of about 1:10 to about 10:1, preferably in the range of about 1:2 to 2:1, can be used. In another preferred embodiment, the mutant protein is solubilized in the presence of a detergent, including a non-ionic detergent, e.g. digitonin N-octyl glucoside, or zwitterionic detergents, such as 3-[(3-cholamidopropyl) dimethylammonio]-1-propanesulfate (CHAPS). In still another embodiment, the refolding reaction occurs in a pH range of about 5.0–10.0, preferably in the range of about 6.0–9.0, more preferably in the range of about 7.0–8.5. In still another embodiment, the refolding reaction occurs at a temperature within the range of about 0–32° C., preferably in the range of about 4–25° C. Where heterodimers are being created, optimal ratios for adding the two different subunits readily can be determined empirically and without undue experimentation.

Purification of heterodimers can be facilitated by adjusting the two monomeric sequences so that they differ in a property useful for purification, such as net charge.

Certain of the compositions of the present invention preferably are manufactured in accordance with the principles disclosed herein by assembly of nucleotides and/or joining DNA restriction fragments to produce synthetic DNAs. The DNAs are transfected into an appropriate protein expression vehicle, the encoded protein expressed, folded, and purified. Particular constructs can be tested for agonist activity in vitro. The tertiary structure of the candidate constructs can be iteratively refined and modulated by site-directed or nucleotide sequence directed mutagenesis aided by the principles disclosed herein, computer-based protein structure modeling, and recently developed rational molecular design techniques to improve or modulate specific properties of a molecule of interest. Known phage display or other expression systems can be exploited to produce simultaneously a large number of candidate constructs. The pool of candidate constructs subsequently can be screened for altered and/or improved binding specificity using, for example, a chromatography column comprising surface immobilized receptors, salt gradient elution to select for, and to concentrate high binding candidates, and in vitro assays to determine whether or not particular isolated candidates agonize the activity of the template superfamily member(s). Identification of a useful construct is followed by production of cell lines expressing commercially useful quantities of the construct far laboratory use and ultimately for producing therapeutically useful molecules. It is contemplated also that preferred constructs, once identified and characterized by the protein and DNA methodologies described herein, can be produced by standard chemical synthesis methodologies.

In another aspect, the invention provides methods for producing TGF-β superfamily member proteins in a host cell, including a bacterial host, or any other host cell where overexpressed protein aggregates in a form that requires solubilization and/or refolding in vitro. The method comprises the steps of providing a host cell transfected with nucleic acid molecules encoding one or more of the recombinant or biosynthetic proteins of the invention, cultivating the host cells under conditions suitable for expressing the recombinant protein, collecting the aggregated protein, and solubilizing and refolding the protein using the steps outlined above. In another embodiment, the method comprises the additional step of transfecting the host cell with a nucleic acid encoding the recombinant or biosynthetic protein of the invention.

In another aspect the invention provides recombinant, chemosynthetic or biosynthetic TGF-β superfamily member proteins having little or no substantial increase in immunogenic effect in a mammal as compared with the parent sequence. The immunogenic effect of a molecule can be readily detected by injecting the molecule, or a portion thereof, into an animal, e,g., a test mouse, and assaying for antibodies produced by the animal in response to the injection and specific for the molecule. Useful assays include any standard protocol for detecting antibodies in serum, for example standard western blots, ELISA's or radio immunoassays.

In still another aspect the invention provides novel methods for creating recombinant, chemosynthetic or biosynthetic TGF-β superfamily member proteins having altered biological properties, including chimeric constructs. In one embodiment individual sub-domains of the C-terminal active region can be exchanged between TGF-β superfamily member molecules to create a chimeric construct with the desired property. For example, the finger 2 sub-domain of a poor refolder can be exchanged for the finger 2 sub-domain of a good refolder to improve the folding properties of the parent protein. Preferably, only non-conserved residues corresponding to the neck or base region finger 2 are exchanged and the loop or tip sequence of the parent sequence is maintained so as to maintain the biological activity of the parent sequence. Alternatively, the biological activity and the folding properties of a parent pour refolder protein can be altered by changing non-conserved residues in both the neck/base region and the tip/loop region of finger 2. Conversely, the biological activity of a good refolder can be altered, without substantially affecting the refolding properties of the protein by replacing the parent protein's finger 1 sub-domain and/or heel sub-domain with that of a TGF-β superfamily member protein having the desired activity, thereby producing a mutant protein. Alternatively, just non conserved residues in the tip of finger 2 can be altered.

The foregoing and other objects, features and advantages of the present invention will be made more apparent from the following detailed description of preferred embodiments of the invention.

BRIEF DESCRIPTION OF THE DRAWINGS

FIG. 1 lists the aligned C-terminal residues defining the finger 2 sub-domain for various known members of the BMP family, and TGF-β superfamily of proteins, starting with the first residue following the cysteine doublet. OP-1 (amino acid residues 66–102 of SEQ ID NO: 55); BMP-5 (amino acid residues 66–102 of SEQ ID NO: 52); BMP-6 (amino acid residues 66–102 of SEQ ID NO: 53); OP-2 (amino acid residues 66–102 of SEQ ID NO: 56); OP-3 (amino acid residues 66–102 of SEQ ID NO: 57); 60A (amino acid residues 82–118 of SEQ ID NO: 48); Vg-1 (amino acid residues 66–102 of SEQ ID NO: 46); Univin (amino acid residues 1–35 of SEQ ID NO: 34); BMP-2 (amino acid residues 66–102 of SEQ ID NO: 49); BMP-4 (amino acid residues 65–101 of SEQ ID NO: 51); GDF-5 (amino acid residues 66–102 of SEQ ID NO: 83); GDF-6 (amino acid residues 66–102 of SEQ ID NO: 85); GDF-7 (amino acid residues 66–102 of SEQ ID NO: 87); CDMP-2 (amino acid residues 66–102 of SEQ ID NO: 86); DPP (amino acid residues 66–102 of SEQ ID NO: 45); BMP-9 (amino acid residues 1–35 of SEQ ID NO: 7); Dorsalin (amino acid residues 66–103 of SEQ ID NO: 54); BMP-10 (amino acid residues 1–35 of SEQ ID NO: 8); GDF-3 (amino acid residues 65–101 of SEQ ID NO: 59); GDF-1 (amino acid residues 71–107 of SEQ ID NO: 58); SCREW (amino acid residues 1–35 of SEQ ID NO: 28); SMP-3 (amino acid residues 67–103 of SEQ ID NO: 50); NODAL (amino acid residues 1–34 of SEQ ID NO: 25); TGF-β1 (amino acid residues 63–98 of SEQ ID NO: 40); TGF-β2 (amino acid residues 63–98 of SEQ ID NO: 41); TGF-β3 (amino acid residues 63–98 of SEQ ID NO: 42); TGF-β4 (amino acid residues 63–98 of SEQ ID NO: 43); TGF-β5 (amino acid residues 63–98 of SEQ ID NO: 44); GDF-5 (amino acid residues 63–98 of SEQ ID NO: 40); Inhibin α (amino acid residues 66–105 of SEQ ID NO: 61); Inhibin βA (amino acid residues 70–106 of SEQ ID NO: 62); Inhibin βB (amino acid residues 70–106 of SEQ ID NO: 63); Inhibin βC (amino acid residues 1–35 of SEQ ID NO: 23); MIS (amino acid residues 1–34 of SEQ ID NO: 24); GDNF (amino acid residues 1–32 of SEQ ID NO: 19); BMP-11 (amino acid residues 1–35 of SEQ ID NO: 9); GDF-9 (amino acid residues 66–102 of SEQ ID NO: 60).

FIG. 3A is a nucleotide sequence and the corresponding amino acid sequence of the OP-1 C-terminal seven cysteine active domain. The DNA sequence corresponds to nucleotides 1036–1341 of SEQ ID NO: 38. The protein sequence corresponds to amino acid residues 330–431 of SEQ ID NO: 39.

FIG. 3B is the nucleotide sequence (SEQ ID NO: 89), and corresponding amino acid sequence (SEQ ID NO:90) of BMP-5 and its alterations for refolding.

FIG. 4A is a schematic representation of exemplary embodiments of chimeric protein constructs of the present invention.

FIG. 4B is a schematic representation of exemplary embodiments of embodiments of the present invention relating to attributes of refolding and ROS activity.

FIG. 5 illustrates a correlation between refolding efficiency and charged amino acids in the TGF-β 7-cysteine domain.

FIGS. 6A, 6B, and 6C are sequence alignments using single letter amino acid code, arranged to indicate homologies of the finger 1, heel, and finger 2 regions, respectively, of some known members of the TGF-b superfamily. Shown are the respective amino acids comprising each region of human TGF-β1 through TGF-β5 (the TGF-β Subgroup), the Vg/dpp subgroup consisting of dpp, Vg-1, Vgr-1, 60A (see copending U.S. Ser. No. 08/271,556), BMP-2A (also known in the literature as BMP-2), dorsalin, BMP-2B (also known in the literature as BMP-4), BMP-3, BMP-5, BMP-6, OP-1 (also known in the literature as BMP-7), OP-2 (see PCT/US91/07635 and U.S. Pat. No. 5,266,683) and OP-3 (U.S. Ser. No. 07/971,091), the GDF subgroup consisting of GDF-1, GDF-3, and GDF-9, the Inhibin subgroup consisting of Inhibin α, Inhibin βA, and Inhibin βB. The dashes (-) indicate a peptide bond between adjacent amino acids. A consensus sequence pattern for each subgroup is shown at the bottom of each subgroup. In FIG. 6A the finger 1 sequences correspond to the following SEQ ID NOS: TGF-β1 (residues 1–34 of SEQ ID NO:40); TGF-β2 (residues 1–34 of SEQ ID NO:41); TGF-β3 (residues 1–34 of SEQ ID NO:42); TGF-β4 (residues 1–34 of SEQ ID NO:43); TGF-β5 (residues 1–34 of SEQ ID NO:44); TGF-β pattern (1–34 of SEQ ID NO: 64); dpp (residues 1–34 of SEQ ID NO:45); Vg-1 (residues 1–34 of SEQ ID NO:46); Vgr-1 (residues 1–34 of SEQ ID NO:47); 60A (residues 1–34 of SEQ ID NO:48); BMP-2A (residues 1–34 of SEQ ID NO:49); DORSALIN (residues 1–34 of SEQ ID NO:54); BMP-2B/BMP-4 (residues 1–34 of SEQ ID NO: 51); BM-3 (residues 1–34 of SEQ ID NO: 50); BMP-5 (residues 1–34 of SEQ ID NO:52); BMP-6 (residues 1–34 of SEQ ID NO:53); OP-1/BMP-7 (residues 1–34 of SEQ ID NO:55); OP-2 (residues 1–34 of SEQ ID NO:56); OP-3 (residues 1–34 of SEQ ID NO:57); Vg/dpp subgroup pattern (residues 1–34 of SEQ ID NO:65); GDF-1 (residues 1–34 of SEQ ID NO:58); GDF-3 (residues 1–34 of SEQ ID NO:59); GDF-9 (residues 1–34 of SEQ ID NO:60); GDF subgroup pattern (residues 1–34 of SEQ ID NO:66); Inhibin α (residues 1–34 of SEQ ID NO:61); Inhibin βA (residues 1–34 of SEQ ID NO:62); Inhibin βB (residues 1–34 of SEQ ID NO:63); Inhibin subgroup pattern (residues 1–34 of SEQ ID NO:67). In FIG. 6B the heel sequences correspond to the following SEQ ID NOS: TGF-β1 (residues 35–64 of SEQ ID NO:40); TGF-β2 (residues 35–64 of SEQ ID NO:41); TGF-β3 (residues 35–64 of SEQ ID NO:42); TGF-β4 (residues 35–64 of SEQ ID NO:43); TGF-β5 (residues 35–64 of SEQ ID NO:44); TGF-β pattern (residues 35–64 of SEQ ID NO: 64); dpp (residues 35–67 of SEQ ID No:45); Vg-1 (residues 35–67 of SEQ ID NO:6); Vgr-1 (residues 35–67 of SEQ ID NO:47); 60A (residues 35–67 of SEQ ID NO:48); BMP-2A (residues 35–66 of SEQ ID NO:49); DORSALIN (residues 35–67 of SEQ ID NO:54); BMP-2B/BMP-4 (residues 35–66 of SEQ ID NO: 51); BMP-3 (residues 35–68 of SEQ ID NO: 50); BMP-5 (residues 35–67 of SEQ ID NO:52); BMP-6 (residues 35–67 of SEQ ID NO:53); OP-1/BMP-7 (residues 35–67 of SEQ ID 35–67 of SEQ ID NO:57); Vg/dpp subgroup pattern (residues 35–68 of SEQ ID NO:65); GDF-1 (residues 35–72 of SEQ ID NO:58); GDF-3 (residues 35–66 of SEQ ID NO:59); GDF-9 (residues 35–67 of SEQ ID NO:60); GDF subgroup pattern (residues 35–72 of SEQ ID NO:66); Inhibin α (residues 35–67 of SEQ ID NO:61); Inhibin A (residues 35–71 of SEQ ID NO:62); Inhibin β3 (residues 35–71 of SEQ ID NO:63); Inhibin subgroup pattern (residues 35–71 of SEQ ID NO:67). In FIG. 6C the finger 2 sequences correspond to the following SEQ ID NOS: TGF-β1 (residues 65–98 of SEQ ID NO:40); TGF-β2 (residues 65–98 of SEQ ID NO:41); TGF-β3 (residues 65–98 of SEQ ID NO:42); TGF-β4 (residues 65–98 of SEQ ID NO:43); TGF-β5 (residues 65–98 of SEQ ID NO:44); TGF-β pattern (residues 65–98 of SEQ ID NO: 64); dpp (residues 68–102 of SEQ ID NO:45); Vg-1 (residues 68–102 of SEQ ID NO:46); Vgr-1 (residues 68–102 of SEQ ID NO:47); 60A (residues 68–102 of SEQ ID NO:48); BMP-2A (residues 68–102 of SEQ ID NO:49); DORSALIN (residues 68–103 of SEQ ID NO:54); BMP-2B/BMP-4 (residues 68–102 of SEQ ID NO: 51); BMP-3 (residues 68–102 of SEQ ID NO: 50); BMP-5 (residues 68–102 of SEQ ID NO:52); BMP-6 (residues 68–102 of SEQ ID NO:53); OP-1/BMP-7 (residues 66–102 of SEQ ID NO:55); OP-2 (residues 66–102 of SEQ ID NO:56); OP-3 (residues 68–102 of SEQ ID NO:57); Vg/dpp subgroup pattern (residues 68–103 of SEQ ID NO:65); GDF-1 (residues 73–107 of SEQ ID NO:58); GDF-3 (residues 67–101 of SEQ ID NO:59); GDF-9 (residues 68–102 of SEQ ID NO:60); GDF subgroup pattern (residues 73–107 of SEQ ID NO:66); Inhibin α (residues 68–105 of SEQ ID NO:61); Inhibin βA (residues 72–106 of SEQ ID NO:62); Inhibin βB (residues 72–106 of SEQ ID NO:63); Inhibin subgroup pattern (residues 72–109 of SEQ ID NO:67)

FIG. 7 identifies preferred pattern sequences for constituting the finger 1, heel, and finger 2 regions of biosynthetic constructs of the invention. The dashes (-) indicate a peptide bond between adjacent amino acids. The SEQ ID NOS for the subgroup patterns are as follows: TGF-β subgroup pattern finger 1 (residues 1–34 of SEQ ID NO:64); TGF-β subgroup pattern heel (residues 35–64 of SEQ ID NO:64); TGF-β subgroup pattern finger 2 (residues 65–98 of SEQ ID NO:64); Vg/dpp subgroup pattern finger 1 (residues 1–34 of SEQ ID NO:65); Vg/dpp subgroup pattern heel (residues 35–68 of SEQ ID NO:65); Vg/dpp subgroup pattern finger 2 (residues 69–104 of SEQ ID NO:65); GDF subgroup pattern finger 1 (residues 1–34 of SEQ ID NO:66); GFD subgroup pattern heel (residues 35–72 of SEQ ID NO:66); GDF subgroup pattern finger 2 (residues 73–107 of SEQ ID NO:66); Inhibin subgroup pattern finger 1 (residues 1–34 of SEQ ID NO:61); Inhibin subgroup pattern heel (residues 35–71 of SEQ ID NO:67); Inhibin subgroup pattern finger 2 (residues 72–109 of SEQ ID NO:67).

DETAILED DESCRIPTION OF PREFERRED EMBODIMENTS

Figure 2:
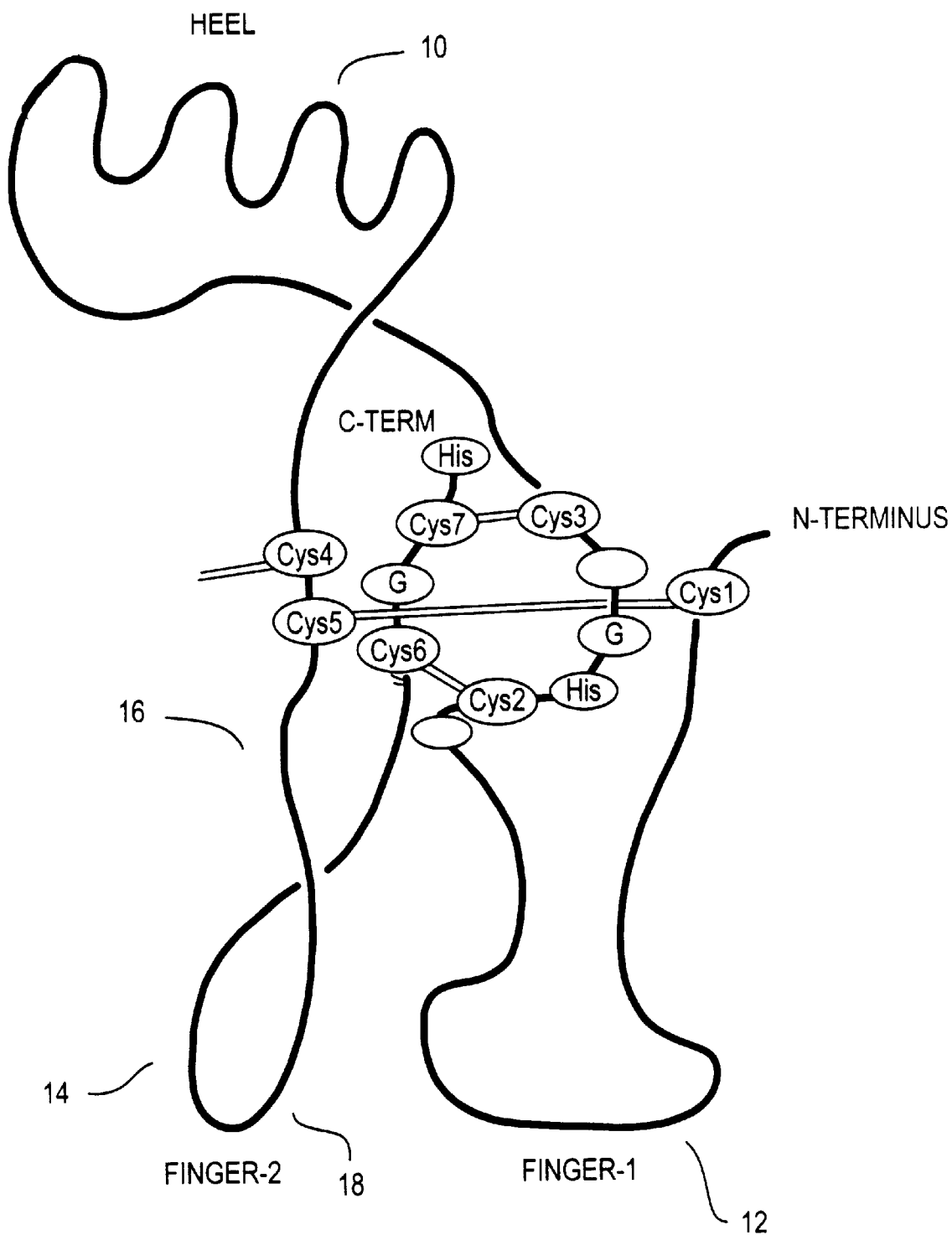
FIG. 2 is a schematic representation of a ribbon model of a BMP C-terminal active domain, showing the seven cysteine skeleton and the three distinct sub-domains: heel (10), finger 1 (12), and finger 2 (14), including the neck or base region (16) and the tip or loop region (18).

Before proceeding further with a detailed description of the currently preferred embodiments of the instant invention, an explanation of certain terms and phrases will be provided. Accordingly, it is understood that each of the terms or phrases set forth below is defined herein at least as follows:

As used herein, "acidic" or "negatively charged residues" are understood to include any amino acid residue, naturally-occurring or synthetic, that carries a negative charge on its R group under neutral pHs, including but not limited to physiologically compatible conditions. Examples include, without limitation, aspartic acid ("Asp") and glutamic acid ("Glu"). Similarly, basic or positively charged residues include any amino acid residue, naturally-occurring or synthetically created, that carries a positive charge on its R group under physiological conditions. Examples include, without limitation, arginine ("Arg"), lysine ("Lys") and histidine ("His"), As used herein, "hydrophilic" residues include both acidic and basic amino acid residues, as well as uncharged residues carrying amide groups on their R groups, including, without limitation, glutamine ("Gln") and asparagine ("Asn"), and polar residues carrying hydroxyl groups on their R groups, including, without limitation, serine ("Ser") and threonine ("Thr").

As used herein, "biosynthesis" or "biosynthetic" means occurring as a result of, or originating from ligation of naturally- or synthetically-derived fragments. For example, but not limited to, site directed mutagenesis, and ligating peptide or nucleic acid fragments corresponding to one or more sub-domains (or fragments /hereon disclosed herein. "Chemosynthesis" or "chemosynthetic" means occurring as a result of, or originating from, a chemical means of production. For example, but not limited to, synthesis of a peptide or nucleic acid sequence using a standard automated synthesizer from a commercially-available source. It is contemplated that both natural and non-natural amino acids can be used to obtain the desired attributes as taught herein. "Recombinant" production or technology means occurring as a result of, or originating from, a genetically engineered means of production. For example, but not limited to, expression of a genetically-engineered DNA sequence or gene encoding a chimeric protein (or fragment thereof) of the present invention. Also included within the meaning of the foregoing are the teachings set forth below in at least Sections I.B.1. (a) and (b); Section II; and at least Examples 1, 2 and 9 (Section III). "Synthetic" means occurring or originating non naturally, i.e., not naturally occurring.

As used herein, "corresponding residue position" refers to a residue position in a protein sequence that corresponds to a given position in a reference amino acid sequence, when the two sequences are aligned. As will be appreciated by those skilled in the art and as illustrated in FIG. 1, the sequences of the BMP family members are highly conserved in the C-terminal active domain, and particularly in the finger 2 sub-domain. Amino acid sequence alignment methods and programs are well developed in the art. See, e.g., the method of Needleman, et al. (1970) *J. Mol. Biol.* 48:443–453, implemented conveniently by computer programs such as the Align program (DNAstar, Inc.). Internal gaps and amino acid insertions in the second sequence are ignored for purposes of calculating the alignment. For ease of description, hOP-1 (human OP-1, also referred to in the art as "BMP-7") is provided below as a representative TGF-β superfamily member. It will be appreciated however, that OP-1 is merely representative of the TGF-β subclass of true tissue morphogens competent to induce tissue morphogenesis.

"Osteogenic protein", or "bone morphogenic protein," means a TGF-β superfamily protein which can induce the full cascade of morphogenic events culminating in skeletal tissue formation, including but not limited to cartilage, ligament, tendon and/or endochondral bone formation. Osleogenic proteins useful herein include any known naturally-occurring native proteins including allelic, phylogenetic counterpart and other variants thereof, whether naturally-occurring or biosynthetically produced (e.g., including "muteins" of "mutant proteins"), as well as new, osteogenically active members of the general morphogenic family of proteins. As described herein, this class of proteins is generally typified by human osteogenic protein (hOP-1). Other osteogenic proteins useful in the practice of the invention include osteogenically active forms of proteins included within the list of: OP-1, OP-2, OP-3, BMP-2, BMP-3, BMP-4, BMP-5, BMP-6, BMP-9, dpp, Vg-1, Vgr, 60A protein, CDMP-1, CDMP-2, CDMP-3, GDF-1, GDF-3, GDF-5, GDF-6, GDF-7, MP-52, BMP-10, BMP-11, BMP-12, BMP-13, BMP-15, UNIVIN, NODAL, SCREW, ADMP or NEURAL, including amino acid sequence variants thereof, and/or heterodimers thereof In one currently preferred embodiment, osteogenic protein useful in the practice of the invention includes any one of: OP-1, BMP-2, BMP-3, BMP-4, BMP-5, BMP-6, BMP-12, BMP-13, GDF-5, GDF-6, GDF-7, CDMP-1, CDMP-2, CDMP-3, MP-52 and amino acid sequence variants and homologs thereof, including species homologs thereof. In still another preferred embodiment, useful osteogenically active proteins have polypeptide chains with amino acid sequences comprising a sequence encoded by a nucleic acid that hybridizes, under low, medium or high stringency hybridization conditions to DNA or RNA encoding reference osteogenic sequences, e.g., C-terminal sequences defining the conserved seven cysteine domains of OP-1, OP-2, BMP-2, BMP-4, BMP-5, BMP-6, 60A, GDF-5, GDF-6, GDF-7 and the like. As used herein, medium stringent hybridization conditions are defined as hybridization according to known techniques in 40% formamide, 5×SSPE, 5×Denhardt's Solution, and 0.1% SDS at 37° C. overnight, and washing in 0.1×SSPE, 0.1% SDS at 50° C. Standard stringency conditions are well characterized in commercially available, standard molecular cloning texts. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984): *Nucleic Acid Hybridization* (B. D. Hames & J. Higgins eds. 1984); and B. Perbal, *A Practical Guide To Molecular Cloning* (1984); the disclosures of the foregoing are incorporated by reference herein. See also, U.S. Pat. Nos. 5,750,651 and 5,863,758, the disclosures of which are incorporated by reference herein.

Other members of the TGF-β superfamily of related proteins having utility in the practice of the instant invention include native poor refolder proteins among the list: TGF-β1, TGF-β2, TGF-β3, TGF-β4 and TGF-β5, various inhibins, activins, BMP-11 and MIS, to name a few. FIG. 1 lists the C-terminal residues defining the finger 2 sub-domain, along with the flanking cysteines, of various known members of the TGF-β superfamily. Any one of the proteins on the list that is a poor refolder can be improved by the methods of the invention, as can other known or discoverable family members. As further described herein, the biologically active osteogenic proteins suitable for use with the present invention can be identified by means of routine experimentation using the bioassay described by Reddi and Sampath as recognized in the art. A detailed description of useful proteins follows. Equivalents can be identified by the artisan using no more than routine experimentation and ordinary skill.

"Morphogens" or "morphogenic proteins" as contemplated herein includes members of the TGF-β superfamily which have been recognized to be morphogenic, i.e., capable of inducing the developmental cascade of tissue morphogenesis in a mature mammal (See PCT Application No. US 92/01968). In particular, these morphogens are capable of inducing the proliferation of uncommitted progenitor cells, and inducing the differentiation of these stimulated progenitor cells in a tissue-specific manner under appropriate environmental conditions. In addition, the morphogens are capable of supporting the growth and maintenance of these differentiated cells. These morphogenic activities allow the proteins to initiate and maintain the developmental cascade of tissue morphogenesis in an appropriate, morphogenically permissive environment, stimulating stem cells to proliferate and differentiate in a tissue-specific manner, and inducing the progression of events that culminate in new tissue formation These morphogenic activities also allow the proteins to induce the "redifferentiation" of cells previously stimulated to stray from their differentiation path Under appropriate environmental conditions it is anticipated that these morphogens also may stimulate the "redifferentiation" of committed cells. To guide the skilled artisan, described herein are numerous means for testing morphogenic proteins in a variety of tissues and for a variety of attributes typical of morphogenic proteins. It will be understood that these teachings can be used to assess morphogenic attributes of native proteins as well as chimeric proteins of the present invention. See, for example, Sections III, Examples 11A–11G for teachings related to morphogenesis of brain, liver, to name but a few.

Useful native or parent proteins of the present invention also include those sharing at least 70% amino acid sequence homology within the C-terminal seven-cysteine domain of human OP-1. To determine the percent homology of a candidate amino acid sequence to the conserved seven-cysteine domain, the candidate sequence and the seven cysteine domain are aligned. The first step for performing an alignment is to use an alignment tool, such as the dynamic programming algorithm described in Needleman et al., *J. Mol. Biol.* 48: 443 (1970), the teachings of which are incorporated by reference herein and the Align Program, a commercial software package produced by DNAstar, Inc. After the initial alignment is made, it is then refined by comparison to a multiple sequence alignment of a family of related proteins. Once the alignment between the candidate sequence and the seven-cysteine domain is made and refined, a percent homology score is calculated. The individual amino acids of each sequence are compared sequentially according to their similarity to each other. Similarity factors include similar size, shape and electrical charge. One particularly preferred method of determining amino acid similarities is the PAM250 matrix described in Dayhoff et al, 5 *Atlas of Protein Sequence and Structure* 345–352 (1978 & Supp.), incorporated by reference herein. A similarity score is first calculated as the sum of the aligned pairwise amino acid similarity scores. Insertions and deletions are ignored for the purposes of percent homology and identity. Accordingly, gap penalties are not used in this calculation. The raw score is then normalized by dividing it by the geometric mean of the scores of the candidate compound and the seven cysteine domain. The geometric mean is the square root of the product of these scores. The normalized raw score is the percent homology.

As used herein, "conservative substitutions" are residues that are physically or functionally similar to the corresponding reference residues, e.g., that have similar size, shape, electric charge, chemical properties including the ability to form covalent or hydrogen bonds, or the like. Particularly preferred conservative substitutions are those fulfilling the criteria defined for an accepted point mutation in Dayhoff et al. (1978), 5 *Atlas of Protein Sequence and Structure*, Suppl. 3, ch. 22 (pp. 354–352), Natl. Biomed. Res. Found., Washington, D.C. 20007, incorporated by reference herein. Examples of conservative substitutions include the substitution of one amino acid for another with similar characteristics, e.g., substitutions within the following groups are well-known: (a) glycine, alanine; (b) valine, isoleucine, leucine; (c) aspartic acid, glutamic acid; (d) asparagine, glutamine; (e) serine, threonine; (f) lysine, arginine, histidine; and (g) phenylalanine, tyrosine. The term "conservative variant" or "conservative variation" also includes the use of a substituted amino acid in place of an unsubstituted parent amino acid in a given polypeptide chain, provided that antibodies having binding specificity for the resulting substituted polypeptide chain also have binding specificity (i.e., "crossreact" or "immunoreact" with) for the unsubstituted or parent polypeptide chain.

As used herein, a "conserved residue position" refers to a location in a reference amino acid sequence occupied by the same amino acid or a conservative variant thereof in at least one other member sequence. For example, in FIG. 1, comparing BMP-2, BMP-4, BMP-5, and BMP-6with OP-1 as the reference sequence, positions such as 2(P), 3(T), 5(L), 7(A), 8(I) and 9(S), etc. are conserved positions, and positions such as 4 (K, E) and 6 (N, S), etc. are non-conserved positions.

As used herein the "base" or "neck" region of the finger 2 sub-domain is defined by residues 1–10 and 22–31, as exemplified by OP-1, and counting from the first residue following the cysteine doublet in the C-terminal active domain. (See FIG. 1). As is readily apparent from a sequence alignment of other TGF-β superfamily protein members with OP-1, the corresponding base or neck region for a longer protein, such as BMP-9 or Dorsalin, is defined by residues 1–10 and 23–32; for a shorter protein, such as NODAL, the corresponding region is defined by residues 1–10 and 21–30 (See FIG. 1). In SEQ ID NO: 39, (human OP-1), the residues corresponding to the base or neck region of the finger 2 sub-domain are residues 397–406 (corresponding to residues 1–10 in FIG. 1) and residues 418–427 (corresponding to residues 22–31 in FIG. 1).

As used herein, "amino acid sequence homology" includes both amino acid sequence identity and similarity. Homologous sequences share identical and/or similar amino acid residues, where similar residues are conservative substitutions for, or "allowed point mutations" of, corresponding amino acid residues in an aligned reference sequence.

As used herein, the terms "chimeric protein", "chimera", "chimeric polypeptide chain", "chimeric construct" and "chimeric mutant" refer to any TGF-β superfamily member synthetic construct wherein the amino acid sequence of at least one defined region, domain or sub-domain, such as a first finger 1, finger 2 or heel sub-domain, has been replaced in whole or in part (e.g., at least about 3, 5, 10, or 15 consecutive amino acid residues) with a second amino acid sequence from at least one other, different TGF-β superfamily member protein, such that the resulting construct has an amino acid sequence recognizable as non-naturally occurring and derived from the different protein sources. Certain preferred chimerics contain a sub-domain from a third different TGF-β superfamily protein or contain two different sub-domains from the second protein. It is understood that a hallmark of preferred embodiments is a refolded structure in which the conserved TGF-β superfamily di-sulfide bridges are retained; see Section I.A. below for a discussion of the conserved 1st, 2nd, 3rd, 5th, 6th and 7th cysteine residues versus the semi-conserved 4th residue.

As used herein, useful expression host cells include prokaryotes and eukaryotes, including any host cell capable of making an inclusion body. Particularly useful host cells include, without limitation, bacterial hosts such as *E. coli*, as well as *B. subtilis* and Pseudomonas. Other useful hosts include lower eukaryotes, such as yeast (*Saccharomyces cereviceae*) and higher eukaryotes, including insect cells such as Drosophila, mammalian cells, such as CHO and the like. An alternative means of production would be chemical synthesis of the mutant construct followed by proper refolding.

The present invention provides recombinant, chemosynthetic or biosynthetic TGF-β superfamily member proteins that have altered refolding attributes, and altered activity profiles compared to naturally-occurring forms. Mutant constructs of the invention comprise amino acid substitutions in naturally-occurring TGF-β superfamily members. The detailed description provided below describes the array of substitutions that result in improved morphogen and pharmaceutical properties. Methods of producing mutant constructs are also taught.

According to the present invention, the attributes of native BMPs or other members of the TGF-β superfamily of proteins, including heterodimers and homodimers thereof, are altered by replacing one or more defined amino acid residues in the C-terminal finger 2 sub-domain with another amino acid residue. As a result of this discovery, it is possible to design TGF-β superfamily proteins that (1) are expressed recombinantly in prokaryotic or eukaryotec cells or chemically synthesized using polypeptide or nucleotide synthesizers; (2) have altered folding attributes; (3) have altered solubility under neutral pHs, including but not limited to physiologically compatible conditions; (4) have altered isoelectric points; (5) have altered stability; (6) have an altered tissue or receptor specificity; (7) have a re-designed, altered biological activity, (8) have altered binding or adherence properties to solid surfaces, such as, but not limited to, biocompatible matrices or metals, and/or (9) have the ability to facilitate formulation. Making use of the discoveries disclosed herein, mutant proteins, which otherwise could not be optimally expressed in a prokaryotic host such as $E.$ $coli$, can now be designed to allow expression in $E.$ $coli$ and optimal refolding in vitro.

Thus, the present invention can provide mechanisms for designing quick-release, slow-release and/or timed-release formulations containing a preferred chimeric protein. Other advantages and features will be evident from the teachings below. Moreover, making use of the discoveries disclosed herein, modified proteins having altered surface-binding/surface-adherent properties can be designed and selected. Surfaces of particular significance include, but are not limited to, solid surfaces which can be naturally-occurring such as bone; or porous particulate surfaces such as collagen or other biocompatible matrices; or the fabricated surfaces of prosthetic implants, including metals. As contemplated herein, virtually any surface can be assayed for differential binding of constructs. Thus, the present invention embraces a diversity of functional molecules having alterations in their surface-binding/surface-adherent properties, thereby rendering such constructs useful for altered in vivo applications, including slow-release, fast-release and/or timed-release formulations.

The skilled artisan will appreciate that mixing-and-matching any one or more the above-recited attributes provides specific opportunities to manipulate the uses of customized mutant proteins (and DNAs encoding the same). For example, the attribute of altered stability can be exploited to manipulate the turnover of mutant proteins in vivo. Moreover, in the case of mutant proteins also having attributes such as altered re-folding and/or function, there is likely an interconnection between folding, function and stability. See, for example, Lipscomb et al., 7 $Protein$ $Sci.$ 765–73 (1998); and Nikolova et al., 95 $Proc.$ $Natl.$ $Acad.$ $Sci.$ $USA$ 14675–80 (1998). For purposes of the present invention, stability alterations can be routinely monitored using well known techniques of circular dichroism other indices of stability as a function of denaturant concentration or temperature. One can also use routine scanning calorimetry. Similarly, there is likely an interconnection between any of the foregoing attributes and the attribute of solubility.

In the case of solubility, it is possible to manipulate this attribute so that a chimeric protein is either more or less soluble under physiologically-compatible and it consequently diffuses readily or remains localized, respectively, when administered in vivo.

Provided below are detailed descriptions of suitable recombinant, chemosynthetic or biosynthetic proteins and DNAs, as well as methods useful in the practice of the invention, and methods for using and testing proteins constructs; also, provided below are numerous, nonlimiting examples which 1) illustrate the utility of the recombinant, chemosynthetic or biosynthetic proteins, DNAs and methods described herein: and 2) provide assays with which to test and use these protein and DNA constructs.

I. PROTEIN CONSIDERATIONS

A. Biochemical, Structural and Functional Properties of Exemplary Members of the TGF-β Superfamily.

Each of the subunits in either TGF β2 or OP-1 have a characteristic folding pattern, that involves six of the seven C-terminal cysteine residues. Briefly, four of the cysteine residues in each subunit form two disulfide bonds which together create an eight residue ring, while two additional cysteine residues form a disulfide bond that passes through the ring to form a knot-like structure. With a numbering scheme beginning with the most N-terminal cysteine of the 7 conserved cysteine residues assigned number 1, the 2nd and 6th cysteine residues are disulfide bonded to close one side of the eight residue ring while the 3rd and 7th cysteine residues are disulfide bonded to close the other side of the ring. The 1st and 5th conserved cysteine residues are disulfide bonded through the center of the ring to form the core of the knot Amino acid sequence alignment patterns suggest this structural motif is conserved between members of the TGF-β superfamily. The 4th cysteine is semi-conserved and when present typically forms an interchain disulfide bond (ICDB) with the corresponding cysteine residue in the other subunit.

The structure of each subunit in TGF-β2 and OP-1 comprise three major tertiary structural elements and an N-terminal region. The structural elements are made up of regions of contiguous polypeptide chain that possess over 50% secondary structure of the following types: (1) loop, (2) α-helix and (3) β-sheet. Another defining criterion for each structural region is that the entering (N-terminal) and exiting (C-terminal) peptide strands are fairly close together, being about 7 Å apart.

The amino acid sequence between the 1st and 2nd conserved cysteines, forms a structural region characterized by an anti-parallel β-sheet finger referred to herein as the finger 1 region. Similarly the residues between the 5th and 6th conserved cysteines, also form an anti-parallel β-sheet finger, referred to herein as the finger 2 region. A β-sheet finger is a single amino acid chain, comprising a β-strand that folds back on itself by means of a β-turn or some larger loop so that the polypeptide chain entering and exiting the region form one or more anti-parallel β-sheet structures. The third major structural region, involving the residues between the 3rd and 5th conserved cysteines, is characterized by a three turn α-helix, referred to herein as the heel region. The organization of the monomer structure is similar to that of a left hand where the knot region is located at the position equivalent to the palm, the finger 1 region is equivalent to the index and middle fingers, the α-helix, or heel region, is equivalent to the heel of the hand, and the finger 2 region is equivalent to the ring and small fingers. The N-terminal region, whose sequence is not conserved across the TGF-β superfamily, is predicted to be located at a position roughly equivalent to the thumb.

In a conformationally active TGF-β2 dimer complex, the two monomer subunits in the dimer complex are oriented with two-fold rotational symmetry such that the heel region of one subunit contacts the finger regions of the other subunit with the knot regions of the connected subunits forming the core of the molecule. The 4th cysteine forms an interchain disulfide bond with its counterpart on the second chain thereby equivalently linking the chains at the center of the palms. The dimer thus formed is an ellipsoidal (cigar shaped) molecule when viewed from the top looking down the two-fold axis of symmetry between the subunits. Viewed from the side, the molecule resembles a bent "cigar" since the two subunits are oriented at a slight angle relative to each other.

The heel region from one subunit, and the finger 1 and finger 2 regions, respectively from the other subunit, interact with one another. These three elements co-operate with one other to define a structure interactive with, and complimentary to the ligand binding interactive surface of the cognate receptor.

Selection of Finger and Heel Regions

It is contemplated that the amino acid sequences defining the finger and heel regions can correspond to the respective finger and heel region sequences of any known member of the TGF-β superfamily. Furthermore, it is contemplated also that the size of the constructs of the invention can be reduced significantly by truncating the natural finger and heel regions of the template TGF-β superfamily member.

As mentioned above, amino acid sequences defining finger and heel regions can be from the respective finger and heel region sequences of any known TGF-β superfamily member, identified herein, or from amino acid sequences of a new superfamily member discovered hereafter, can be used in the present invention.

FIG. 6 summarizes the amino acid sequences of currently identified TGF-β superfamily members aligned into finger 1 (FIG. 6A), heel (FIG. 6B) and finger 2 (FIG. 6C) regions. The sequences were aligned by a computer algorithm which in order to optimally align the sequences inserted gaps into regions of amino acid sequence known to define loop structures rather than regions of amino acid sequence known to have conserved amino acid sequence or secondary structure. For example, if possible, no gaps were introduced into amino acid sequences of finger 1 and finger 2 regions defined by β sheet or heel regions defined by α helix. The dashes (-) indicate a peptide bond between adjacent amino acids. A consensus sequence pattern for each subgroup is shown at the bottom of each subgroup.

After the amino acid sequences of each of the TGF-β superfamily members were aligned, the aligned sequences were used to produce amino acid sequence alignment patterns which identify amino acid residues that may be substituted by another amino acid or group of amino acids without altering the overall tertiary structure of the resulting construct. The amino acids or groups of amino acids that may be useful at a particular position in the finger and heel regions were identified by a computer algorithm implementing the amino acid hierarchy pattern structure shown in FIG. 8.

Briefly, the algorithm performs four levels of analysis. In level I, the algorithm determines whether a particular amino acid residue occurs with a frequency greater than 75% at a specific position within the amino acid sequence. For example, if a glycine residue occurs 8 out of 10 times at a particular position in an amino acid sequence, then a glycine is designated at that position. If the position to be tested consists of all gaps then a gap character (-) is assigned to the position, otherwise, if at least one gap exists then a "z" (standing for any residue or a gap) is assigned to the position. If, no amino acid occurs in 75% of the candidate sequences at a particular position the algorithm implements the Level II analysis.

Level II defines pattern sets a, b, d, l, k, o, n, i, and h, wherein l, k, and o share a common amino acid residue. The algorithm then determines whether 75% or more of the amino acid residues at a particular position in the amino acid sequence satisfy one of the aforementioned patterns. If so, then the pattern is assigned to that position. It is possible, however, that both patterns l and k may be simultaneously satisfied because they share the same amino acid, specifically aspartic acid. If simultaneous assignment of l and k occurs then pattern m (Level III) is assigned to that position. Likewise, it is possible that both patterns k and o may be simultaneously assigned because they share the same amino acid, specifically glutamic acid. If simultaneous assignment of k and o occurs, then pattern q (Level III) is assigned to that position. If neither a Level II pattern nor the Level III patterns, m and q, satisfy a particular position in the amino acid sequence then the algorithm implements a Level III analysis.

Level III defines pattern sets c, e, m, q, p, and j, wherein m, q, and p share a common amino residue. Pattern q, however, is not tested in the Level III analysis. It is possible that both patterns m and p may be simultaneously satisfied because they share the same amino acid, specifically, glutamic acid. If simultaneous assignment of m and p occurs then pattern r (Level IV) is assigned to that position. If 75% of the amino acids at a pre-selected position in the aligned amino acid sequences satisfy a Level III pattern, then the Level III pattern is assigned to that position. If a Level III pattern cannot be assigned to that position then the algorithm implements a Level IV analysis.

Level IV comprises two non-overlapping patterns f and r. If 75% of the amino acids at a particular position in the amino acid sequence satisfy a Level IV pattern then the pattern is assigned to the position. If no Level IV pattern is assigned the algorithm assigns an X representing any amino acid (Level V) to that position.

In FIG. 8, Level I lists in upper case letters in single amino acid code the 20 naturally occurring amino acids. Levels II–V define, in lower case letters, groups of amino acids based upon the amino acid hierarchy set forth in Smith et al., supra. The amino acid sequences set forth in FIG. 6 were aligned using the aforementioned computer algorithms.

It is contemplated that if the artisan wishes to produce a construct based upon currently identified members of the TGF-β superfamily, then the artisan can use the amino acid sequences shown in FIG. 6 to provide the finger 1, finger 2 and heel regions useful in the production of the mutants of the invention. In the case of members of the TGF-β superfamily discovered hereafter, the amino acid sequence of the new member can be aligned, either manually or by means of a computer algorithm, with the sequences set forth in FIG. 6 to define heel and finger regions useful in the practice of the invention.

Table 1 below summarizes publications which describe the amino acid sequences of each TGF-β superfamily member that were used to produce the sequence alignment patterns set forth in FIGS. 6–8.

TABLE 1

| TGF-β Superfamily Member | SEQ ID NO: | Publication |
|---|---|---|
| TGF-β1 | 40 | Derynck et al. (1987) Nucl. Acids. Res. 15:3187 |
| TGF-β2 | 41 | Burt et al. (1991) DNA Cell Biol. 10:723–734 |
| TGF-β3 | 42 | Ten Dijke et al. (1988) Proc. Natl. Acad. Sci. USA 85:4715–4719; Derynck et al. (1988) EMBO J. 7:3737–3743. |
| TGF-β4 | 43 | Burt et al. (1992) Mol. Endcrinol. 6:989–922. |
| TGF-β5 | 44 | Kondaiah et al. (1990) J. Biol. Chem 265:1089–1093 |
| dpp | 45 | Padgett et al. (1987) Nature 325:81–84; Paganiban et al. (1990) Mol. Cell Biol. 10:2669–2677. |
| vg-1 | 46 | Weeks et al. (1987) Cell 51:861–867 |
| vgr-1 | 47 | Lyons et al. (1989) Proc. Natl. Acad. Sci USA 86:4554–4558 |
| 60A | 48 | Wharton et al. (1991) Proc. Natl. Acad. Sci. USA 88:9214–9218; Doctor et al. (1992) Dev. Biol. 151:491–505 |
| BMP-2A | 49 | Wozney et al. (1988) Science 242:1528–1534 |
| BMP-3 | 50 | Wozney et al. (1988) Science 242:1528–1534 |
| BMP-4 | 51 | Wozney et al. (1988) Science 242:1528–1534 |
| BMP-5 | 52 | Celeste et al. (1990) Proc. Natl. Acad. Sci. USA 87:9843–9847 |
| BMP-6 | 53 | Celeste et al. (1990) Proc. Natl. Acad. Sci. USA 87:9843–9847 |
| Dorsalin | 54 | Basler et al. (1993) Cell 73:687–702 |
| OP-1 | 55 | Ozkaynak et al. (1990) Embo J. 9:2085–2093; Celeste et al. (1990) Proc. Natl. Acad. Sci. USA 87:9843–9847 |
| OP-2 | 56 | Ozkaynak et al. (1992) J. Biol. Chem. 267:25220–25227 |
| OP-3 | 57 | Ozkaynak et al. PCT/WO94/10203 SEQ ID NO: 1 |
| GDF-1 | 58 | Lee (1990) Mol. Endcrinol. 4:1034–1040 |
| GDF-3 | 59 | McPherron et al. (1993) J. Biol. Chem. 268:3444–3449 |
| GDF-9 | 60 | McPherron et al. (1993) J. Biol. Chem. 268:3444–3449 |
| Inhibin α | 61 | Mayo et al. (1986) Proc. Natl. Acad. Sci. USA 83:5849–5853; Stewart et al. (1986) FEBS Lett 206:329–334; Mason et al. (1986) Biochem. Biophys. Res. Commun. 135:957–964 |
| Inhibin βA | 62 | Forage et al. (1986) Proc. Natl. Acad. Sci. USA 83:3091–3095; Chertov et al. (1990) Biomed. Sci. 1:499–506 |
| Inhibin βB | 63 | Mason et al. (1986) Biochem. Biophys. Res. Commun. 135:957–964 |

In particular, it is contemplated that amino acid sequences defining finger 1 regions useful in the practice of the instant invention correspond to the amino acid sequence defining a finger 1 region for any TGF-β superfamily member identified herein. The finger 1 sub-domain can confer at least biological and/or functional attribute(s) which are characteristic of the native protein. Useful intact finger 1 regions include, but are not limited to

| TGF-β1 | SEQ ID NO: 40, residues 2 through 29, |
|---|---|
| TGF-β2 | SEQ ID NO: 41, residues 2 through 29, |
| TGF-β3 | SEQ ID NO: 42, residues 2 through 29, |
| TGF-β4 | SEQ ID NO: 43, residues 2 through 29, |
| TGF-β5 | SEQ ID NO: 44, residues 2 through 29, |
| dpp | SEQ ID NO: 45, residues 2 through 29, |
| Vg-1 | SEQ ID NO: 46, residues 2 through 29, |
| Vgr-1 | SEQ ID NO: 47, residues 2 through 29, |
| 60A | SEQ ID NO: 48, residues 2 through 29, |
| BMP-2A | SEQ ID NO: 49, residues 2 through 29, |
| BMP-3 | SEQ ID NO: 50, residues 2 through 29, |
| BMP-4 | SEQ ID NO: 51, residues 2 through 29, |
| BMP-5 | SEQ ID NO: 52, residues 2 through 29, |
| BMP-6 | SEQ ID NO: 53, residues 2 through 29, |
| Dorsalin | SEQ ID NO: 54, residues 2 through 29, |
| OP-1 | SEQ ID NO: 55, residues 2 through 29, |
| OP-2 | SEQ ID NO: 56, residues 2 through 29, |
| OP-3 | SEQ ID NO: 57, residues 2 through 29, |
| GDF-1 | SEQ ID NO: 58, residues 2 through 29, |
| GDF-3 | SEQ ID NO: 59, residues 2 through 29, |
| GDF-9 | SEQ ID NO: 60, residues 2 through 29, |
| Inhibin α | SEQ ID NO: 61, residues 2 through 29, |
| Inhibin βA | SEQ ID NO: 62, residues 2 through 29, |
| Inhibin βB | SEQ ID NO: 63, residues 2 through 29, |
| CDMP-1/GDF-5 | SEQ ID NO: 83, residues 2 through 29, |
| CDMP-2/GDF-6 | SEQ ID NO: 84, residues 2 through 29, |
| GDF-6 (murine) | SEQ ID NO: 85, residues 2 through 29, |
| CDMP-2 (bovine) | SEQ ID NO: 86, residues 2 through 29, and |
| GDF-7 (murine) | SEQ ID NO: 87, residues 2 through 29. |

The invention further contemplates the use of corresponding finger 1 subdomain sequences from the well-known proteins BMP-12 and BMP-13 (as disclosed in U.S Pat. No. 5,658,882, the entire disclosure of which is incorporated by reference herein).

It is contemplated also that amino acid sequences defining heel regions useful in the practice of the instant invention correspond to the amino acid sequence defining an intact heel region for any TGF-β superfamily member identified herein. The heel region can at least influence attributes of the native protein, including functional and/or folding attributes. Useful intact heel regions may include, but are not limited to

| TGF-β1 | SEQ ID NO: 40, residues 35 through 62, |
|---|---|
| TGF-β2 | SEQ ID NO: 41, residues 35 through 62, |
| TGF-β3 | SEQ ID NO: 42, residues 35 through 62, |
| TGF-β4 | SEQ ID NO: 43, residues 35 through 62, |
| TGF-β5 | SEQ ID NO: 44, residues 35 through 62, |
| dpp | SEQ ID NO: 45, residues 35 through 65, |
| Vg-1 | SEQ ID NO: 46, residues 35 through 65, |
| Vgr-1 | SEQ ID NO: 47, residues 35 through 65, |
| 60A | SEQ ID NO: 48, residues 35 through 65, |
| BMP-2A | SEQ ID NO: 49, residues 35 through 64, |
| BMP3 | SEQ ID NO: 50, residues 35 through 66, |
| BMP-4 | SEQ ID NO: 51, residues 35 through 64, |
| BMP-5 | SEQ ID NO: 52, residues 35 through 65, |
| BMP-6 | SEQ ID NO: 53, residues 35 through 65, |
| Dorsalin | SEQ ID NO: 54, residues 35 through 65, |
| OP-1 | SEQ ID NO: 55, residues 35 through 65, |
| OP-2 | SEQ ID NO: 56, residues 35 through 65, |
| OP-3 | SEQ ID NO: 57, residues 35 through 65, |
| GDF-1 | SEQ ID NO: 58, residues 35 through 70, |
| GDF-3 | SEQ ID NO: 59, residues 35 through 64, |
| GDF-9 | SEQ ID NO: 60, residues 35 through 65, |
| Inhibin α | SEQ ID NO: 61, residues 35 through 65, |
| Inhibin βA | SEQ ID NO: 62, residues 35 through 69, |
| Inhibin βB | SEQ ID NO: 63, residues 35 through 68, |
| CDMP-1/GDF-5 | SEQ ID NO: 83, residues 35 through 65, |
| CDMP-2/GDF-6 | SEQ ID NO: 84, residues 35 through 65, |
| GDF-6 (murine) | SEQ ID NO: 85, residues 35 through 65, |
| CDMP-2 (bovine) | SEQ ID NO: 86, residues 35 through 65, and |
| GDF-7 (murine) | SEQ ID NO: 87, residues 35 through 65. |

The invention further contemplates the use of corresponding heel region sequences from the well-known proteins BMP-12 and BMP-13 (as disclosed in U.S Pat. No. 5,658,882, the entire disclosure of which is incorporated by reference herein).

It is contemplated also that amino acid sequences defining finger 2 regions useful in the practice of the instant invention correspond to the amino acid sequence defining an intact finger 2 region for any TGF-β superfamily member identified herein. The finger 2 sub-domain can confer at least folding attribute(s) which are characteristic of the native protein. Useful intact finger 2 regions may include, but are not limited to

| | |
|---|---|
| TGF-β1 | SEQ ID NO: 40, residues 65 through 94, |
| TGF-β2 | SEQ ID NO: 41, residues 65 through 94, |
| TGF-β3 | SEQ ID NO: 42, residues 65 through 94, |
| TGF-β4 | SEQ ID NO: 43, residues 65 through 94, |
| TGF-β5 | SEQ ID NO: 44, residues 65 through 94, |
| dpp | SEQ ID NO: 45, residues 68 through 98, |
| Vg-1 | SEQ ID NO: 46, residues 68 through 98, |
| Vgr-1 | SEQ ID NO: 47, residues 68 through 98, |
| 60A | SEQ ID NO: 48, residues 68 through 98, |
| BMP-2A | SEQ ID NO: 49, residues 67 through 97, |
| BMP-3 | SEQ ID NO: 50, residues 69 through 99, |
| BMP-4 | SEQ ID NO: 51, residues 67 through 97, |
| BMP-5 | SEQ ID NO: 52, residues 68 through 98, |
| BMP-6 | SEQ ID NO: 53, residues 68 through 98, |
| Dorsalin | SEQ ID NO: 54, residues 68 through 99, |
| OP-1 | SEQ ID NO: 55, residues 68 through 98, |
| OP-2 | SEQ ID NO: 56, residues 68 through 98, |
| OP-3 | SEQ ID NO: 57, residues 68 through 98, |
| GDF-1 | SEQ ID NO: 58, residues 73 through 103, |
| GDF-3 | SEQ ID NO: 59, residues 67 through 97, |
| GDF-9 | SEQ ID NO: 60, residues 68 through 98, |
| Inhibin α | SEQ ID NO: 61, residues 68 through 101, |
| Inhibin βA | SEQ ID NO: 62, residues 72 through 102, |
| Inhibin βB | SEQ ID NO: 63, residues 71 through 101, |
| CDMP-1/GDF-5 | SEQ ID NO: 83, residues 68 through 98, |
| CDMP-2/GDF-6 | SEQ ID NO: 84, residues 68 through 98, |
| GDF-6 (murine) | SEQ ID NO: 85, residues 68 through 98, |
| CDMP-2 (bovine) | SEQ ID NO: 86, residues 68 through 98, and |
| GDF-7 (murine) | SEQ ID NO: 87, residues 68 through 98. |

The invention further contemplates the use of corresponding finger 2 subdomain sequences from the well-known proteins BMP-12 and BMP-13 (as disclosed in U.S. Pat. No. 5,658,882, the entire disclosure of which is incorporated by reference herein).

Figure 8:
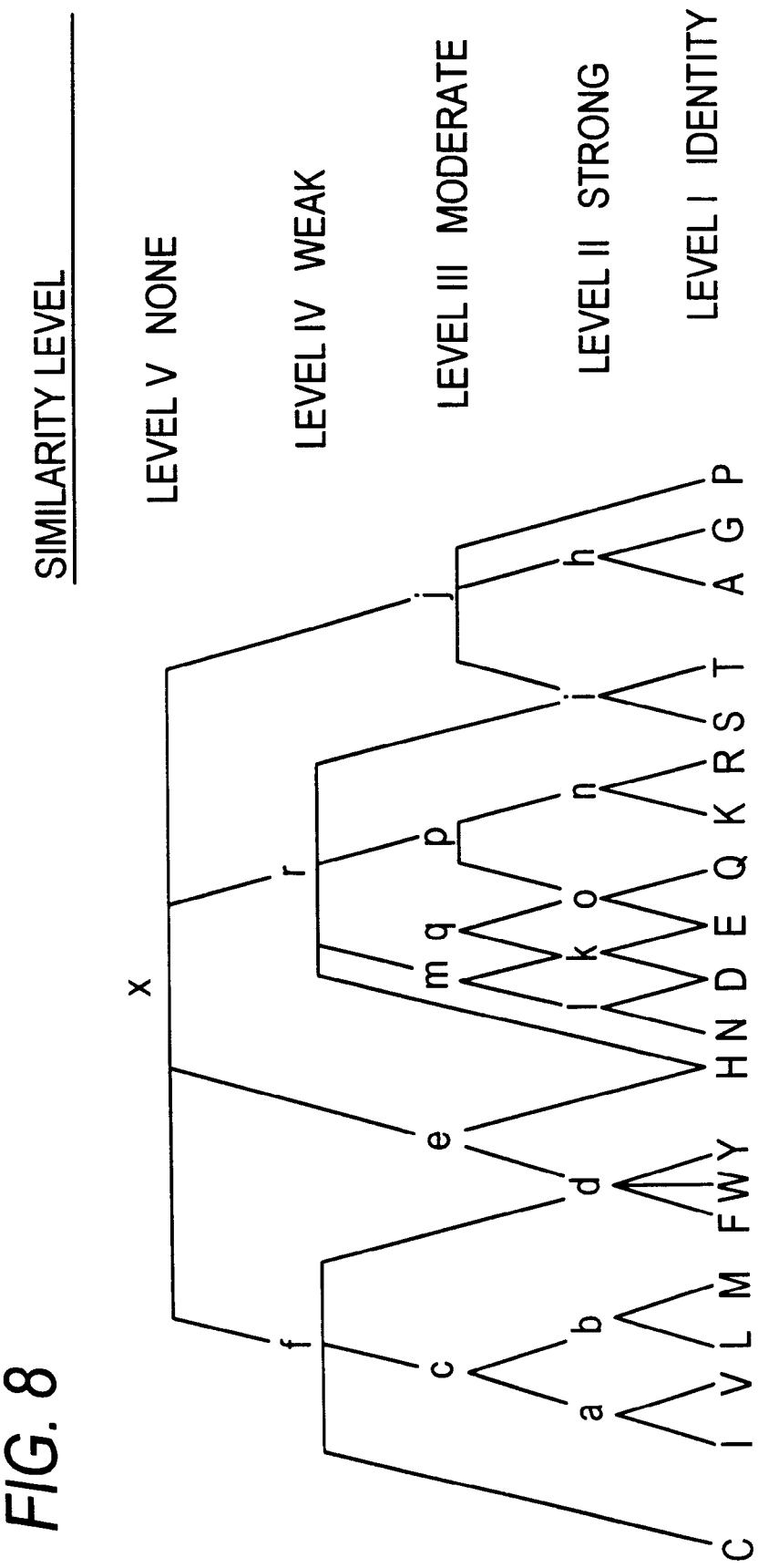
FIG. 8 is a pattern definition table prepared in accordance with the teaching of Smith and Smith (1990) *Proc. Natl. Acad. Sci. USA* 87:118–122.

In addition, it is contemplated that the amino acid sequences of the respective finger and heel regions can be altered by amino acid substitution, for example by exploiting substitute residues as disclosed herein or selected in accordance with the principles disclosed in Smith et al. (1990), supra. Briefly, Smith et al. disclose an amino acid class hierarchy similar to the one summarized in FIG. 8, which can be used to rationally substitute one amino acid for another while minimizing gross conformational distortions of the type which could compromise protein function. In any event, it is contemplated that many synthetic first finger, second finger, and heel region sequences, having only 70% homology with natural regions, preferably 80%, and most preferably at least 90%, can be used to produce the constructs of the present invention.

Amino acid sequence patterns showing amino acids preferred at each location in the finger and heel regions, deduced in accordance with the principles described in Smith et al. (1990) supra, also are show in FIGS. 6–7, and are referred to as the: TGF-β; Vg/dpp; GDF; and Inhibin subgroup patterns. The amino acid sequences defining the finger 1, heel and finger 2 sequence patterns of each subgroup are set forth in FIGS. 6A, 6B, and 6C, respectively. In addition, the amino acid sequences defining the entire TGF-β, Vg/dpp, GDF and Inhibin subgroup patterns are set forth in the Sequence Listing as SEQ ID NOs: 64, 65, 66, and 67, respectively.

Figure 6B:
Figure 7:
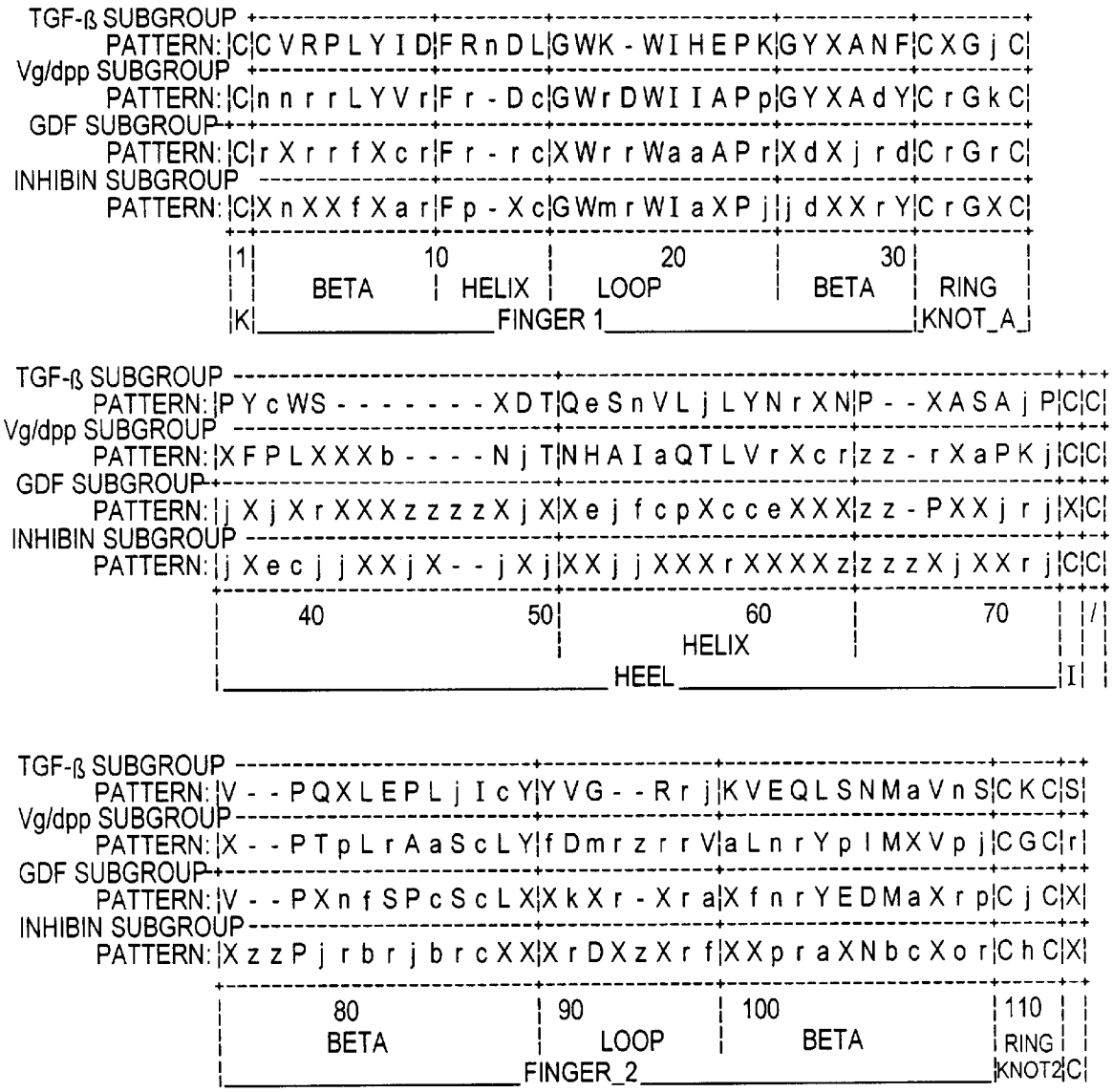
FIG. 7 is a single letter code listing of amino acid sequences, identified in capital letter in standard single letter amino acid code, and in lower case letters to identify groups of amino acids useful in that location, wherein the lower case letters stand for the amino acids indicated in accordance with the pattern definition key table set forth in FIG. 8.

The preferred amino acid sequence patterns for each subgroup, disclosed in FIGS. 6A, 6B, and 6C, and summarized in FIG. 7, enable one skilled in the art to identify alternative amino acids that can be incorporated at specific positions in the finger 1, heel, and finger 2 elements. The amino acids identified in upper case letters in a single letter amino acid code identify conserved amino acids that together are believed to define structural and functional elements of the finger and heel regions. The upper case letter "X" in FIGS. 6 and 7 indicates that any naturally occurring amino acid is acceptable at that position. The lower case letter "z" in FIGS. 6 and 7 indicates that either a gap or any of the naturally occurring amino acids is acceptable at that position. The lower case letters stand for the amino acids indicated in accordance with the pattern definition table set forth in FIG. 8 and identify groups of amino acids which are useful in that location.

In accordance with the amino acid sequence subgroup patterns set forth in FIGS. 6–7, it is contemplated, for example, that the skilled artisan can predict that where applicable, one amino acid may be substituted by another without inducing disruptive stereochemical changes within the resulting protein construct. For example, in FIG. 6A, in the Vg/dpp subgroup pattern at residue numbers 2 and 3, it is contemplated that either a lysine residue (K) or a arginine residue (R) may he present at this position without affecting the structure of the resulting construct. Accordingly, the sequence pattern at position 2 and 3 contain an "n" which, in accordance with FIG. 8, defines an amino acid residue selected from the group consisting of lysine or arginine. It is contemplated, therefore, that many synthetic finger 1, finger 2 and heel region amino acid sequences, having 70% homology, preferably 80%, and most preferably at least 90% with the natural regions, can be used to produce conformationally active constructs of the invention.

In accordance with these principles, it is contemplated that one can design a synthetic construct by starting with the amino acid sequence patterns belonging to the TGF-β, Vg/dpp, GDF, or inhibin subgroup patterns shown in FIGS. 6 and 7. Thereafter, by using conventional recombinant or synthetic methodologies a preselected amino acid may be substituted by another as guided by the principles herein and the resulting protein construct tested as provided below.

The TGF-β subgroup pattern, SEQ ID NO: 64, accommodates the homologies shared among members of the TGF-β subgroup identified to date including TGF-β1, TGF-β2, TGF-β3, TGF-β4, and TGF-β5. The generic sequence, shown below, includes both the conserved amino acids (standard three letter code) as well as alternative amino acids (Xaa) present at the variable positions within the sequence and defined by the rules set forth in FIG. 8.

| TGF-β Subgroup Pattern | | | | | | | | | | | | | | |
|---|---|---|---|---|---|---|---|---|---|---|---|---|---|---|
| Cys 1 | Cys | Val | Arg | Pro 5 | Leu | Tyr | Ile | Asp | Phe 10 | Arg | Xaa | Asp | Leu | Gly 15 | Trp |
| Lys | Trp | Ile | His 20 | Glu | Pro | Lys | Gly | Tyr 25 | Xaa | Ala | Asn | Phe | Cys 30 | Xaa | Gly |
| Xaa | Cys | Pro 35 | Tyr | Xaa | Trp | Ser | Xaa 40 | Asp | Thr | Gln | Xaa | Ser 45 | Xaa | Val | Leu |
| Xaa | Leu 50 | Tyr | Asn | Xaa | Xaa | Asn 55 | Pro | Xaa | Ala | Ser | Ala 60 | Xaa | pro | Cys | Cys |
| Val 65 | Pro | Gln | Xaa | Leu | Glu 70 | Pro | Leu | Xaa | Ile | Xaa 75 | Tyr | Tyr | Val | Gly | Arg 80 |
| Xaa | Xaa | Lys | Val | Glu 85 | Gln | Leu | Ser | Asn | Met 90 | Xaa | Val | Xaa | Ser | Cys 95 | Lys |
| Cys | Ser. | | | | | | | | | | | | | | |

Each Xaa can be independently selected from a group of one or more specified amino acids defined as follows, wherein: Xaa12 is Arg or Lys; Xaa26 is Ala, Arg, Asn, Asp, Cys, Glu, Gln, Gly, His, Ile, Leu, Lys, Met, Phe, Pro, Ser, Thr; Trp, Tyr or Val; Xaa31 is Ala, Arg, Asn, Asp, Cys, Glu, Gln, Gly, His, Ile, Leu, Lys, Met, Phe, Pro, Ser, Thr, Trp, Tyr or Val; Xaa33 is Ala, Gly, Pro, Ser, or Thr; Xaa37 is Ile, Leu, Met or Val, Xaa40 is Ala, Arg, Asn, Asp, Cys, Glu, Gln, Gly, His, Ile, Leu, Lys, Met, Phe, Pro, Ser, Thr, Trp, Tyr or Val; Xaa44 is His, Phe, Trp or Tyr; Xaa46 is Arg or Lys; Xaa49 is Ala, Gly, Pro, Ser, or Thr; Xaa53 is Arg, Asn, Asp, Gln, Glu, His, Lys, Ser or Thr; Xaa54 is Ala, Arg, Asn, Asp, Cys, Glu, Gln, Gly, His, Ile, Leu, Lys, Met, Phe, Pro, Ser, Thr, Trp, Tyr or Val; Xaa57 is Ala, Arg, Asn, Asp, Cys, Glu, Gln, Gly, His, Ile, Leu, Lys, Met, Phe, Pro, Ser, Thr, Trp, Tyr or Val; Xaa61 is Ala, Gly, Pro, Ser, or Thr; Xaa68 is Ala, Arg, Asn, Asp, Cys, Glu, Gln, Gly, His, Ile, Leu, Lys, Met, Phe, Pro, Ser, Thr, Trp, Tyr or Val; Xaa73 is Ala, Gly, Pro, Ser, or Thr, Xaa75 is Ile, Leu, Met or Val; Xaa81 is Arg, Asn, Asp, Gln, Glu, His, Lys, Ser or Thr; Xaa82 is Ala, Gly, Pro, Ser, or Thr; Xaa91 is Ile or Val; Xaa93 is Arg or Lys.

The Vg/dpp subgroup pattern, SEQ ID NO: 65, accommodates the homologies shared among members of the Vg/dpp subgroup identified to date including dpp, vg-1, vgr-1, 60A, BMP-2A (BMP-2), Dorsalin, BMP-2B (BMP-4), BMP-3, BMP-5, BMP-6, OP-1 (BMP-7), OP-2 and OP-3. The generic sequence, below, includes both the conserved amino acids (standard three letter code) as well as alternative amino acids (Xaa) present at the variable positions within the sequence and defined by the rules set forth in FIG. 8.

| Vg/dpp Subgroup Pattern | | | | | | | | | | | | | | |
|---|---|---|---|---|---|---|---|---|---|---|---|---|---|---|
| Cys 1 | Xaa | Xaa | Xaa | Xaa 5 | Leu | Tyr | Val | Xaa | Phe 10 | Xaa | Asp | Xaa | Gly | Trp 15 | Xaa |
| Asp | Trp | Ile | Ile 20 | Ala | Pro | Xaa | Gly | Tyr 25 | Xaa | Ala | Xaa | Tyr | Cys 30 | Xaa | Gly |
| Xaa | Cys | Xaa 35 | Phe | Pro | Leu | Xaa | Xaa 40 | Xaa | Xaa | Asn | Xaa | Thr 45 | Asn | His | Ala |
| Ile | Xaa 50 | Gln | Thr | Leu | Val | Xaa 55 | Xaa | Xaa | Xaa | Xaa | Xaa 60 | Xaa | Xaa | Xaa | Pro |
| Lys 65 | Xaa | Cys | Cys | Xaa | Pro 70 | Thr | Xaa | Leu | Xaa | Ala 75 | Xaa | Ser | Xaa | Leu | Tyr 80 |
| Xaa | Asp | Xaa | Xaa | Xaa 85 | Xaa | Xaa | Val | Xaa | Leu 90 | Xaa | Xaa | Tyr | Xaa | Xaa 95 | Met |
| Xaa | Val | Xaa | Xaa | Cys 100 | Gly | Cys | Xaa. | | | | | | | | |

Each Xaa can be independently selected from a group of one or more specified amino acids defined as follows, wherein: Xaa2 is Arg or Lys; Xaa3 is Arg or Lys; Xaa4 is Arg, Asn, Asp, Gln, Glu, His, Lys, Ser or Thr; Xaa5 is Arg, Asn, Asp, Gln, Glu, His, Lys, Ser or Thr; Xaa9 is Arg, Asn, Asp, Gln, Glu, His, Lys, Ser or Thr; Xaa11 is Arg, Asn, Asp, Gln, Glu, His, Lys, Ser or Thr; Xaa13 is Ile, Leu, Met or Val; Xaa16 is Arg, Asn, Asp, Gln, Glu, His, Lys, Set or Thr; Xaa23 is Arg, Gln, Glu, or Lys; Xaa26 is Ala, Arg, Asn, Asp, Cys, Gln, Gln, Gly, His, Ile, Leu, Lys, Met, Phe, Pro, Ser, Thr, Trp, Tyr or Val; Xaa28 is Phe, Trp or Tyr; Xaa31 is Arg, Asn, Asp, Gln, Glu, His, Lys, Ser or Thr; Xaa33 is Asp or Gln; Xaa35 is Ala, Arg, Asn, Asp, Cys, Gln, Gln, Gly, His, Ile, Leu, Lys, Met, Phe, Pro, Ser, Thr, Trp, Tyr or Val; Xaa39 is Ala, Arg, Asn, Asp, Cys, Gln, Gln, Gly, His, Ile, Leu, Lys, Met, Phe, Pro, Ser, Thr, Tip, Tyr or Val; Xaa40 is Ala, Arg, Asn, Asp, Cys, Glu, Gln, Gly, His, Ile, Leu, Lys, Met, Phe, Pro, Ser, Thr, Trp, Tyr or Val; Xaa41 is Ala, Arg, Asn, Asp, Cys, Glu, Gln, Gly, His, Ile, Leu, Lys, Met, Phe, Pro, Ser, Thr, Trp, Tyr or Val; Xaa42 is Leu or Met; Xaa44 is Ala, Gly, Pro, Ser, or Thr; Xaa50 is Ile or Val; Xaa55 is Arg, Asn, Asp, Gln, Glu, His, Lys, Ser or Thr; Xaa56 is Ala, Arg, Asn, Asp, Cys, Glu, Gln, Gly, His, Ile, Leu, Lys, Met, Phe, Pro, Ser, Thr, Trp, Tyr or Val; Xaa57 is Ile, Leu, Met or Val; Xaa58 is Arg, Asn, Asp, Gln, Glu, His, Lys, Ser or Thr; Xaa59 is Ala, Arg, Asn, Asp, Cys, Gln, Gln, Gly, His, Ile, Leu, Lys, Met, Phe, Pro, Ser, Thr, Trp, Tyr, Val or a peptide bond; Xaa60 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa61 is Arg, Asn, Asp, Gln, Glu, His, Lys, Ser or Thr; Xaa62 is Ala, Arg, Asn, Asp, Cys, Glu, Gln, Gly, His, Ile, Leu, Lys, Met, Phe, Pro, Ser, Thr, Trp, Tyr or Val; Xaa63 is Ile or Val; Xaa66 is Ala, Gly, Pro, Ser, or Thr; Xaa69 is Ala, Arg, Asn, Asp, Cys, Glu, Gln, Gly, His, Ile, Leu, Lys, Met, Phe, Pro, Ser, Thr, Trp, Tyr or Val; Xaa72 is Arg, Gln, Glu, or Lys; Xaa74 is Arg, Asn, Asp, Gln, Glu, His, Lys, Ser or Thr; Xaa76 is Ile or Val; Xaa78 is Ile, Leu, Met or Val; Xaa81 is Cys, Ile, Leu, Met, Phe, Trp, Tyr or Val; Xaa83 is Asn, Asp or Glu; Xaa84 is Arg, Asn, Asp, Gln, Gln, His, Lys, Ser or Thr; Xaa85 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa86 is Arg, Asn, Asp, Gln, Glu, His, Lys, Ser or Thr; Xaa87 is Arg, Asn, Asp, Gln, Gln, His, Lys, Ser or Thr; Xaa89 is Ile or Val; Xaa91 is Arg or Lys; Xaa92 is Arg, Asn, Asp, Gln, Glu, His, Lys, Ser or Thr; Xaa94 is Arg, Gln, Glu,or Lys; Xaa95 is Asn or Asp; Xaa97 is Ala, Arg, Asn, Asp, Cys, Glu, Gln, Gly, His, Ile, Leu, Lys, Met, Pre, Pro, Ser, Thr, Trp, Tyr or Val; Xaa99 is Arg, Gln, Glu, or Lys; Xaa100 is Ala, Gly, Pro, Ser, or Thr; Xaa104 is Arg, Asn, Asp, Gln, Glu, His, Lys, Ser or Thr.

The GDF subgroup pattern, SEQ ID NO: 66, accommodates the homologies shared among members of the GDF subgroup identified to date including GDF-1, GDF-3, and GDF-9. The generic sequence, shown below, includes both the conserved amino acids (standard three letter code) as well as alternative amino acids (Xaa) present al the variable positions within the sequence and defined by the rules set forth in FIG. 8.

Each Xaa can be independently selected from a group of one or more specified amino acids defined as follows, wherein: Xaa2 is Arg, Asn, Asp, Gln, Glu, His, Lys, Ser or Thr; Xaa3 is Ala, Arg, Asn, Asp, Cys, Glu, Gln, Gly, His, Ile, Leu, Lys, Met, Phe, Pro, Ser, Thr, Trp, Tyr or Val; Xaa4 is Arg, Asn, Asp, Glu, Gln, His, Lys, Ser or Thr; Xaa5 is Arg, Asn, Asp, Gln, Glu, His, Lys, Ser or Thr; Xaa6 is Cys, Ile, Leu, Met, Phe, Trp, Tyr or Val; Xaa7 is Ala, Arg, Asn, Asp, Cys, Glu, Gln, Gly, His, Ile, Leu, Lys, Met, Phe, Pro, Ser, Thr, Trp, Tyr or Val; Xaaa is Ile, Leu, Met or Val; Xaa9 is Arg, Asn, Asp, Gln, Glu, His, Lys, Ser or Thr; Xaa11 is Arg, Asn, Asp, Gln, Glu, His, Lys, Ser or Thr; Xaa12 is Arg, Asn, Asp, Gln, Glu, His, Lys, Ser or Tin; Xaa13 is Ile, Leu, Met or Val; Xaa14 is Ala, Arg, Asn, Asp, Cys, Glu, Gln, Gly, His, Ile, Leu, Lys, Met, Phe, Pro, Ser, Thr, Trp, Tyr or Val; Xaa16 is Arg, Asn, Asp, Gln, Gln, His, Lys, Ser or Thr; Xaa17 is Arg, Asn, Asp, Gln, Glu, His, Lys, Ser or Thr; Xaa19 is Ile or Val; Xaa20 is Ile or Val; Xaa23 is Arg, Asn, Asp, Gln, Glu, His, Lys, Ser or Thr; Xaa24 is Ala, Arg, Asn, Asp, Cys, Gln, Gln, Gly, His, Ile, Leu, Lys, Met, Phe, Pro, Ser, Thr, Trp, Tyr or Val; Xaa25 is Phe, Trp or Tyr; Xaa26 is Ala, Arg, Asn, Asp, Cys, Glu, Gln, Gly, His, Ile, Leu, Lys, Met, Phe, Pro, Ser, Thr, Trp, Tyr or Val; Xaa27 is Ala, Gly, Pro, Ser, or Thr; Xaa28 is Arg, Asn, Asp, Gln, Glu, His, Lys, Ser or Thr; Xaa29 is Phe, Trp or Tyr; Xaa31 is Arg, Asn, Asp, Gln, Glu, His, Lys, Ser or Thr; Xaa33 is Arg, Asn, Asp, Gln, Glu, His, Lys, Ser or Thr; Xaa35 is Ala, Gly, Pro, Ser, or Thr, Xaa36 is Ala, Arg, Asn, Asp, Cys, Glu, Gln, Gly, His, Ile, Leu, Lys, Met, Phe, Pro, Ser, Thr, Trp, Tyr or Val; Xaa37 is Ala, Gly, Pro, Ser, or Thr; Xaa38 is Ala, Arg, Asn, Asp, Cys, Glu, Gln, Gly, His, Ile, Leu, Lys, Met, Phe, Pro, Ser, Thr, Trp, Tyr or Val; Xaa39 is Arg, Asn, Asp, Gln, Glu, His, Lys, Ser or Thr; Xaa40 is Ala, Arg, Asn, Asp, Cys, Gln, Gln, Gly, His, Ile, Leu; Lys, Met, Phe, Pro, Ser, Thr, Trp, Tyr or Val; Xaa41 is Ala, Arg, Asn, Asp, Cys, Glu, Gln, Gly, His, Ile, Leu, Lys, Met, Phe, Pro, Ser, Thr, Trp, Tyr or Val; Xaa42 is Ala, Arg, Asn, Asp, Cys, Glu, Gln, Gly, His, Ile, Leu, Lys, Met, Phe, Pro, Ser, Thr, Trp, Tyr or Val; Xaa43 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa44 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa45 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa46 is Ala, Arg, Asn, Asp, Cys, Glu, Gln, Gly, His, Ile, Leu, Lys, Met,

---

GDF Subgroup Pattern

```
Cys Xaa Xaa Xaa Xaa Xaa Xaa Xaa Xaa Phe Xaa Xaa Xaa Xaa Trp Xaa
1           5                       10                      15

Xaa Trp Xaa Xaa Ala Pro Xaa Xaa Xaa Xaa Xaa Xaa Cys Xaa Gly
            20              25                  30

Xaa Cys Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Pro Xaa Xaa Xaa Xaa Xaa Cys Val Pro Xaa Xaa Xaa Ser Pro Xaa
65              70                  75                  80

Ser Xaa Leu Xaa Xaa Xaa Xaa Xaa Xaa Xaa Xaa Xaa Xaa Xaa Tyr
            85                  90                  95

Glu Asp Met Xaa Xaa Xaa Xaa Cys Xaa Cys Xaa.
            100             105
```

Phe, Pro, Ser, Thr, Trp, Tyr, Val or a peptide bond; Xaa47 is Ala, Arg, Asn, Asp, Cys, Glu, Gln, Gly, His, Ile, Leu, Lys, Met, Phe, Pro, Ser, Thr, Trp, Tyr or Val; Xaa48 is Ala, Gly, Pro, Ser, or Thr; Xaa49 is Ala, Arg, Asn, Asp, Cys, Glu, Gln, Gly, His, Ile, Leu, Lys, Met, Phe, Pro, Ser, Thr, Trp, Tyr or Val; Xaa50 is Ala, Arg, Asn, Asp, Cys, Glu, Gln, Gly, His, Ile, Leu, Lys, Met, Phe, Pro, Ser, Thr, Trp, Tyr or Val; Xaa51 is His, Phe, Trp or Tyr; Xaa52 is Ala, Gly, Pro, Ser, or Thr; Xaa53 is Cys, Ile, Leu, Met, Phe, Trp, Tyr or Val; Xaa54 is Ile, Leu, Met or Val; Xaa55 is Arg, Gln, Glu,or Lys; Xaa56 is Ala, Arg, Asn, Asp, Cys, Glu, Gln, Gly, His, Ile, Leu, Lys, Met, Phe, Pro, Ser, Thr, Trp, Tyr or Val; Xaa57 is Ile, Leu, Met or Val; Xaa58 is Ile, Leu, Met or Val; Xaa59 is His, Phe, Trp or Tyr; Xaa60 is Ala, Arg, Asn, Asp, Cys, Glu, Gln, Gly, His, Ile, Leu, Lys, Met, Phe, Pro, Ser, Thr, Trp, Tyr or Val; Xaa61 is Ala, Arg, Asn, Asp, Cys, Glu, Gln, Gly, His, Ile, Leu, Lys, Met, Phe, Pro, Ser, Thr, Trp, Tyr or Val; Xaa62 is Ala, Arg, Asn, Asp, Cys, Glu, Gln, Gly, His, Ile, Leu, Lys, Met, Phe, Pro, Ser, Thr, Trp, Tyr or Val; Xaa63 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa64 is Ala, Arg, Asn, Asp, Cys, Glu, Gln, Gly, His, Ile, Leu, Lys, Met, Phe, Pro, Ser, Thr, Trp, Tyr, Val or a peptide band; Xaa66 is Ala, Arg, Asn, Asp, Cys, Glu, Gln, Gly, His, Ile, Leu, Lys, Met, Phe, Pro, Ser, Thr, Trp, Tyr or Val; Xaa67 is Ala, Arg, Asn, Asp, Cys, Glu, Gln, Gly, His, Ile, Leu, Lys, Met, Phe, Pro, Ser, Thr, Trp, Tyr or Val; Xaa68 is Ala, Gly, Pro, Ser, or Thr; Xaa69 is Arg, Asn, Asp, Gln, Glu, His, Lys, Ser or Thr; Xaa70 is Ala, Gly, Pro, Ser, or Thr; Xaa71 is Ala, Arg, Asn, Asp, Cys, Glu, Gln, Gly, His, Ile, Leu, Lys, Met, Phe, Pro, Ser, Thr, Trp, Tyr or Val; Xaa75 is Ala, Arg, Asn, Asp, Cys, Glu, Gln, Gly, His, Ile, Leu, Lys, Met, Phe, Pro, Ser, Thr, Trp, Tyr or Val; Xaa76 is Arg or Lys; Xaa77 is Cys, Ile, Leu, Met, Phe, Trp, Tyr or Val; Xaa80 is Ile, Leu, Met or Val; Xaa82 is Ile, Leu, Met or Val; Xaa84 is Ala, Arg, Asn, Asp, Cys, Glu, Gln, Gly, His, Ile, Leu, Lys, Met, Phe, Pro, Ser, Thr, Tip, Tyr or Val; Xaa85 is Ala, Arg, Asn, Asp, Cys, Glu, Gln, Gly, His, Ile, Leu, Lys, Met, Phe, Pro, Ser, Thr, Trp, Tyr or Val; Xaa86 is Asp or Gln; Xaa87 is Ala, Arg, Asn, Asp, Cys, Glu, Gln, Gly, His, Ile, Leu, Lys, Met, Phe, Pro, Ser, Thr, Trp, Tyr or Val; Xaa88 is Arg, Asn, Asp, Gln, Gly, His, Lys, Ser or Thr; Xaa89 is Ala, Arg, Asn, Asp, Cys, Glu, Gln, Gly, His, Ile, Leu, Lys, Met, Phe, Pro, Ser, Thr, Trp, Tyr or Val; Xaa90 is Arg, Asn, Asp, Gln, Glu, His, Lys, Ser or Thr; Xaa91 is Ile or Val; Xaa92 is Ala, Arg, Asn, Asp, Cys, Glu, Gln, Gly, His, Ile, Leu, Lys, Met, Phe, Pro, Ser, Thr, Trp, Tyr Or Val; Xaa93 is Cys, Ile, Leu, Met, Phe, Trp, Tyr or Val; Xaa94 is Arg or Lys; Xaa95 is Arg, Asn, Asp, Gln, Glu, His, Lys, Ser or Thr; Xaa100 is Ile or Val; Xaa101 is Ala, Arg, Asn, Asp, Cys, Glu, Gln, Gly, His, Ile, Leu, Lys, Met, Phe, Pro, Ser, Thr, Trp, Tyr or Val; Xaa102 is Arg, Asn, Asp, Gln, Glu, His, Lys, Ser or Thr; Xaa103 is Arg, Gln, Glu, or Lys; Xaa105 is Ala, Gly, Pro, Ser, or Thr; Xaa107 is Ala, Arg, Asn, Asp, Cys, Glu, Gln, Gly, His, Ile, Leu, Lys, Met, Phe, Pro, Ser, Thr, Trp, Tyr or Val.

The Inhibin subgroup pattern, SEQ ID NO: 67, accommodates the homologies shared among members of the Inhibin subgroup identified to date including Inhibin α, Inhibin βA and Inhibin βB. The generic sequence, shown below, includes both the conserved amino acids (standard three letter code) as well as alternative amino acids (Xaa) present at the variable positions within the sequence and defined by the rules set forth in FIG. 8.

```
                    Inhibin Subgroup pattern

Cys Xaa Xaa Xaa Xaa Xaa Xaa Xaa Xaa Phe Xaa Xaa Xaa Gly Trp Xaa
1               5                   10                  15

Xaa Trp Ile Xaa Xaa Pro Xaa Xaa Xaa Xaa Xaa

Xaa31 is Arg, Asn, Asp, Gln, Glu, His, Lys, Ser, or Thr; Xaa33 is Ala, Arg, Asn, Asp, Cys, Glu, Gln, Gly, His, Ile, Leu, Lys, Met, Phe, Pro, Ser, Thr, Trp, Tyr or Val; Xaa35 is Ala, Gly, Pro, Ser, or Thr; Xaa36 is Ala, Arg, Asn, Asp, Cys, Glu, Gln, Gly, His, Ile, Leu, Lys, Met, Phe, Pro, Ser, Thr, Trp, Tyr or Val; Xaa37 is His, Phe, Trp or Tyr; Xaa38 is Ile, Leu, Met or Val; Xaa39 is Ala, Gly, Pro, Ser, or Thr; Xaa40 is Ala, Gly, Pro, Ser, or Thr; Xaa41 is Ala, Arg, Asn, Asp, Cys, Glu, Gln, Gly, His, Ile, Leu, Lys, Met, Phe, Pro, Ser, Thr, Trp, Tyr or Val; Xaa42 is Ala, Arg, Asn, Asp, Cys, Glu, Gln, Gly, His, Ile, Leu, Lys, Met, Phe, Pro, Ser, Thr, Trp, Tyr or Val; Xaa43 is Ala, Gly, Pro, Ser, or Thr; Xaa44 is Ala, Arg, Asn, Asp, Cys, Glu, Gln, Gly, His, Ile, Leu, Lys, Met, Phe, Pro, Ser, Thr, Trp, Tyr or Val; Xaa45 is Ala, Gly, Pro, Ser, or Thr; Xaa46 is Ala, Arg, Asn, Asp, Cys, Glu, Gln, Gly, His, Ile, Leu, Lys, Met, Phe, Pro, Ser, Thr, Trp, Tyr or Val; Xaa47 is Ala, Gly, Pro, Ser, or Thr; Xaa48 is Ala, Arg, Asn, Asp, Cys, Glu, Gln, Gly, His, Ile, Leu, Lys, Met, Phe, Pro, Ser, Thr, Trp, Tyr or Val; Xaa49 is Ala, Arg, Asn, Asp, Cys, Glu, Gln, Gly, His, Ile, Leu, Lys, Met, Phe, Pro, Ser, Thr, Trp, Tyr or Val; Xaa50 is Ala, Gly, Pro, Ser, or Thr; Xaa51 is Ala, Gly, Pro, Ser, or Thr; Xaa52 is Ala, Arg, Asn, Asp, Cys, Glu, Gln, Gly, His, Ile, Leu, Lys, Met, Phe, Pro, Ser, Thr, Trp, Tyr or Val; Xaa53 is Ala, Arg, Asn, Asp, Cys, Glu, Gln, Gly, His, Ile, Leu, Lys, Met, Phe, Pro, Ser, Thr, Trp, Tyr or Val; Xaa54 is Ala, Arg, Asn, Asp, Cys, Glu, Gln, Gly, His, Ile, Leu, Lys, Met, Phe, Pro, Ser, Thr, Trp, Tyr or Val; Xaa55 is Arg, Asn, Asp, Gln, Glu, His, Lys, Ser or Thr; Xaa56 is Ala, Arg, Asn, Asp, Cys, Glu, Gln, Gly, His, Ile, Leu, Lys, Met, Phe, Pro, Ser, Thr, Trp, Tyr or Val; Xaa57 is Ala, Arg, Asn, Asp, Cys, Glu, Gln, Gly, His, Ile, Leu, Lys, Met, Phe, Pro, Ser, Thr, Trp, Tyr or Val; Xaa58 is Ala, Arg, Asn, Asp, Cys, Glu, Gln, Gly, His, Ile, Leu, Lys, Met, Phe, Pro, Ser, Thr, Trp, Tyr or Val; Xaa59 is Ala, Arg, Asn, Asp, Cys, Glu, Gln, Gly, His, Ile, Leu, Lys, Met, Phe, Pro, Ser, Thr, Trp, Tyr or Val; Xaa60 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa67 is Ala, Arg, Asn, Asp, Cys, Glu, Gln, Gly, His, Ile, Leu, Lys, Met, Phe, Pro, Ser, Thr, Tip, Tyr, Val or a peptide bond; Xaa62 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa63 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa64 is Ala, Arg, Asn, Asp, Cys, Glu, Gln, Gly, His, Ile, Leu, Lys, Met, Phe, Pro, Ser, Thr, Trp, Tyr or Val; Xaa65 is Ala, Gly, Pro, Ser, or Thr; Xaa66 is Ala, Arg, Asn, Asp, Cys, Glu, Gln, Gly, His, Ile, Leu, Lys, Met, Phe, Pro, Ser, Thr, Trp, Tyr or Val; Xaa67 is Ala, Arg, Asn, Asp, Cys, Glu, Gln, Gly, His, Ile, Leu, Lys, Met, Phe, Pro, Ser, Thr, Trp, Tyr or Val; Xaa68 is Arg, Asn, Asp, Gln, Gln, His, Lys, Ser or Thr; Xaa69 is Ala, Gly, Pro, Ser, or Thr; Xaa72 is Ala, Arg, Asn, Asp, Cys, Glu, Gln, Gly, His, Ile, Leu, Lys, Met, Phe, Pro, Ser, Thr, Trp, Tyr or Val; Xaa73 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa74 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa76 is Ala, Gly, Pro, Ser, or Thr; Xaa77 is Arg, Asn, Asp, Gln, Glu, His, Lys, Ser or Thr; Xaa78 is Leu or Met; Xaa79 is Arg, Asn, Asp, Gln, Glu, His, Lys, Ser or Thr; Xaa80 is Ala, Gly, Pro, Ser, or Thr; Xaa81 is Leu or Met; Xaa82 is Arg, Asn, Asp, Gln, Gln, His, Lys, Ser or Thr; Xaa83 is Ile, Leu, Met or Val; Xaa84 is Ala, Arg, Asn, Asp, Cys, Glu, Gln, Gly, His, Ile, Leu, Lys, Met, Phe, Pro, Ser, Thr, Trp, Tyr or Val; Xaa85 is Ala, Arg, Asn, Asp, Cys, Glu, Gln, Gly, His, Ile, Leu, Lys, Met, Phe, Pro, Ser, Thr, Trp, Tyr or Val; Xaa86 is Ala, Arg, Asn, Asp, Cys, Glu, Gln, Gly, His, Ile, Leu, Lys, Met, Phe, Pro, Ser, Thr, Trp, Tyr or Val; Xaa87 is Arg, Asn, Asp, Gln, Glu, His, Lys, Ser or Thr; Xaa89 is Ala, Arg, Asn, Asp, Cys, Glu, Gln, Gly, His, Ile, Leu, Lys, Met, Phe, Pro, Ser, Thr, Trp, Tyr or Val; Xaa90 is Ala, Arg, Asn, Asp, Cys, Gln, Gln, Gly, His, Ile, Leu, Lys, Met, Phe, Pro, Ser, Thr, Trp, Tyr, Val or a peptide bond; Xaa91 is Ala, Arg, Asn, Asp, Cys, Glu, Gln, Gly, His, Ile, Leu, Lys, Met, Phe, Pro, Ser, Thr, Trp, Tyr or Val; Xaa92 is Arg, Asn, Asp, Gln, Glu, His, Lys, Ser or Thr; Xaa93 is Cys, Ile, Leu, Met, Phe, Trp, Tyr or Val; Xaa94 is Ala, Arg, Asn, Asp, Cys, Glu, Gln, Gly, His, Ile, Leu, Lys, Met, Phe, Pro, Ser, Thr, Trp, Tyr or Val; Xaa95 is Ala, Arg, Asn, Asp, Cys, Glu, Gln, Gly, His, Ile, Leu, Lys, Met, Phe, Pro, Ser, Thr, Trp, Tyr or Val; Xaa96 is Arg, Gln, Glu,or Lys; Xaa97 is Arg, Asn, Asp, Gln, Glu, His, Lys, Ser or Thr, Xaa98 is Ile or Val; Xaa99 is Ala, Arg, Asn, Asp, Cys, Gln, Gln, Gly, His, Ile, Leu, Lys, Met, Phe, Pro, Ser, Thr, Trp, Tyr or Val; Xaa101 is Leu or Met; Xaa102 is Ile, Leu, Met or Val; Xaa103 is Ala, Arg, Asn, Asp, Cys, Glu, Gln, Gly, His, Ile, Leu, Lys, Met, Phe, Pro, Ser, Thr, Trp, Tyr or Val; Xaa104 is Gln or Glu; Xaa105 is Arg, Asn, Asp, Gln, Glu, His, Lys, Ser or Thr; Xaa107 is Ala or Gly; Xaa109 is Ala, Arg, Asn, Asp, Cys, Glu, Gln, Gly, His, Ile, Leu, Lys, Met, Phe, Pro, Ser, Thr, Trp, Tyr or Val.

B. Recombinant Production Considerations

1. Design and Production of the Protein and DNA Constructs of the Present Invention As mentioned above, the constructs of the invention can be manufactured by using conventional recombinant DNA methodologies well known and thoroughly documented in the art, as well as by using well-known biosynthetic and chemosynthetic methodologies using routine peptide or nucleotide chemistries and automated peptide or nucleotide synthesizers. Such routine methodologies are described for example in the following publications, the teachings of which are incorporated by reference herein: Hilvert, 1 *Chem. Biol.* 201–3 (1994); Muir et al., 95 *Proc. Natl. Acad. Sci. USA* 6705–10 (1998); Wallace, 6 *Curr. Opin. Biotechnol.* 403–10 (1995); Miranda et al., 96 *Proc. Natl. Acad. Sci. USA* 1181–86 (1999); Liu et al., 91 *Proc. Natl. Acad. Sci. USA* 6584–88 (1994), Suitable for use in the present invention are naturally-occurring amino acids and nucleotides; non-naturally occurring amino acids and nucleotides; modified or unusual amino acids; modified bases; amino acid sequences that contain post-translationally modified amino acids and/ or modified linkages, cross-links and end caps, non-peptidyl bonds, etc.; and, further including without limitation, those moieties disclosed in the *World Intellectual Property Organization* (WIPO) Handbook on Industrial Property Information and Documentation, Standard St. 25 (1998) including Tables 1 through 6 in Appendix 2, herein incorporated by reference. Equivalents of the foregoing will be appreciated by the skilled artisan relying only on routine experimentation together with the knowledge of the art.

For example, the contemplated DNA constructs may be manufactured by the assembly of synthetic nucleotide sequences and/or joining DNA restriction fragments to produce a synthetic DNA molecule. The DNA molecules then are ligated into an expression vehicle, for example an expression plasmid, and transfected into an appropriate host cell, for example *E. coli*. The contemplated protein construct encoded by the DNA molecule then is expressed, purified, refolded, tested in vitro for certain attributes, e.g., binding activity with a receptor having binding affinity for the template TGF-β superfamily member, and subsequently tested to assess whether the biosynthetic construct mimics other preferred attributes of the template superfamily member.

Alternatively, a library of synthetic DNA constructs can be prepared simultaneously for example, by the assembly of synthetic nucleotide sequences that differ in nucleotide composition in a preselected region. For example, it is contemplated that during production of a construct based upon a specific TGF-β superfamily member, the artisan can choose appropriate finger and heel regions for such a superfamily member (for example from FIGS. 6–7). Once the appropriate finger and heel regions have been selected, the artisan then can produce synthetic DNA encoding these regions. For example, if a plurality of DNA molecules encoding different linker sequences are included into a ligation reaction containing DNA molecules encoding finger and heel sequences, by judicious choice of appropriate restriction sites and reaction conditions, the artisan may produce a library of DNA constructs wherein each of the DNA constructs encode finger and heel regions but connected by different linker sequences. The resulting DNAs then are ligated into a suitable expression vehicle, i.e., a plasmid useful in the preparation of a phage display library, transfected into a host cell, and the polypeptides encoded by the synthetic DNAs expressed to generate a pool of candidate proteins. The pool of candidate proteins subsequently can be screened to identify specific proteins having the desired binding affinity and/or selectivity for a pre-selected receptor.

Screening can be performed by passing a solution comprising the candidate proteins through a chromatographic column containing surface immobilized receptor. Then proteins with the desired binding specificity are eluted, for example by means of a salt gradient and/or a concentration gradient of the template TGF-β superfamily member. Nucleotide sequences encoding such proteins subsequently can be isolated and characterized. Once the appropriate nucleotide sequences have been identified, the lead proteins subsequently can be produced, either by conventional recombinant DNA or peptide synthesis methodologies, in quantities sufficient to test whether the particular construct mimics the activity of the template TGF-β superfamily member.

It is contemplated that, which ever approach is adopted to produce DNA molecules encoding constructs of the invention, the tertiary structure of the preferred proteins can subsequently be modulated in order to optimize binding and/or biological activity by, for example, by a combination of nucleotide mutagenesis methodologies aided by the principles described herein and phage display methodologies. Accordingly, an artisan can produce and test simultaneously large numbers of such proteins.

(a) Gene and Protein Synthesis

The processes for manipulating, amplifying, and recombining DNA which encode amino acid sequences of interest generally are well known in the art, and therefore, are not described in detail herein. Methods of identifying and isolating genes encoding members of the TGF-β superfamily also are well understood, and are described in the patent and other literature.

Briefly, the construction of DNAs encoding the biosynthetic constructs disclosed herein is performed using known techniques involving the use of various restriction enzymes which make sequence specific cuts in DNA to produce blunt ends or cohesive ends, DNA ligases, techniques enabling enzymatic addition of sticky ends to blunt-ended DNA, construction of synthetic DNAs by assembly of short or medium length oligonucleotides, cDNA synthesis techniques, polymerase chain reaction (PCR) techniques for amplifying appropriate nucleic acid sequences from libraries, and synthetic probes for isolating genes of members of the TGF-β superfamily and their cognate receptors. Various promoter sequences from bacteria, mammals, or insects to name a few, and other regulatory DNA sequences used in achieving expression, and various types of host cells are also known and available. Conventional transfection techniques, and equally conventional techniques for cloning and subcloning DNA are useful in the practice of this invention and known to those skilled in the art. Various types of vectors may be used such as plasmids and viruses including animal viruses and bacteriophages. The vectors may exploit various marker genes that impart to a successfully transfected cell a detectable phenotypic property that can be used to identify which of a family of clones has successfully incorporated the recombinant DNA of the vector.

One method for obtaining DNA encoding the biosynthetic constructs disclosed herein is by assembly of synthetic oligonucleotides produced in a conventional, automated, oligonucleotide synthesizer followed by ligation with appropriate ligases. For example, overlapping, complementary DNA fragments may be synthesized using phosphoramidite chemistry, with end segments left unphosphorylated to prevent polymerization during ligation. One end of the synthetic DNA is left with a "sticky end" corresponding to the site of action of a particular restriction endonuclease, and the other end is left with an end corresponding to the site of action of another restriction endonuclease. The complementary DNA fragments are ligated together to produce a synthetic DNA construct.

Alternatively nucleic acid strands encoding finger 1, finger 2 and heel regions can be isolated from libraries of nucleic acids, for example, by colony hybridization procedures such as those described in Sambrook et al. eds. (1989) "*Molecular Cloning*", Coldspring Harbor Laboratories Press, NY, and/or by PCR amplification methodologies, such as those disclosed in Innis et al. (1990) "*PCR Protocols, A guide to methods and applications*", Academic Press. The nucleic acids encoding the finger and heel regions then are joined together to produce a synthetic DNA encoding the biosynthetic single-chain morphon construct of interest.

It is appreciated, however, that a library of DNA constructs encoding a plurality thereof can be produced simultaneously by standard recombinant DNA methodologies, such as the ones, described above, For example, the skilled artisan by the use of cassette mutagenesis or oligonucleotide directed mutagenesis can produce, for example, a series of DNA constructs each of which contain different DNA sequences within a predefined location, e.g., within a DNA cassette encoding a linker sequence. The resulting library of DNA constructs subsequently can be expressed, for example, in a phage or viral display library or a eukaryotic cell line (e.g., CHO cell line); and any protein constructs that binds to a specific receptor may be isolated by affinity purification, e.g., using a chromatographic column comprising surface immobilized receptor. Once molecules that bind the preselected receptor have been isolated, their binding and agonist properties can be modulated using empirical refinement techniques.

Methods of mutagenesis of proteins and nucleic acids are well known and well described in the art. See, e.g., Sambrook et al., (1990) *Molecular Cloning. A Laboratory Manual.*, 2d ed. (Cold Spring Harbor, N.Y.: Cold Spring Harbor Laboratory Press). Useful methods include PCR (overlap extension, see, e.g., *PCR Primer* (Dieffenbach and Dveksler, eds., Cold Spring Harbor Press, Cold Spring Harbor, N.Y., 1995, pp. 603–611)); cassette mutagenesis and single-stranded mutagenesis following the method of Kunkel. It will be appreciated by the artisan that any suitable method of mutagenesis can be utilized and the mutagenesis method is not considered a material aspect of the invention. The nucleotide codons competent to encode amino acids, including arginine (Arg), glutamic acid (Glu) and aspartic acid (Asp) also are well known and described in the art. See, for example, Lehninger, Biochemistry (Worth Publishers, N.Y., N.Y.). Standard codons encoding arginine, glutamic acid and aspartic acid are: Arg: CGU, CGC, CGA, CGG, AGA, AGG; Glu: CAA, GAG; and Asp: GAU, GAC. Mutant constructs of the invention can readily be constructed by aligning the nucleic acid sequences or domains to be switched, and identifying compatible splice sites and/or constructing suitable crossover sequences using PCR overlap extension.

(b) Protein Expression

One of the advantages of the present invention relates to protein expression and production, especially commercially significant quantities of protein. As disclosed herein, mutant proteins can be endowed with certain preferred attributes such as enhanced/improved refolding attributes. Moreover, chimeric proteins with enhanced proteins with enhanced/ improved refolding attribute can be designed to be expressed in bacterial cells that could not be properly expressed in mammalian cells. It is contemplated that such enhanced refolding will improve recovery and commercial production TGF-$\beta$ superfamily proteins. It is also now appreciated that mammalian cells can identify misfolded proteins and have cellular processes that permit such proteins to be recycled and then refolded properly. Such proteins will be discarded, however, if they fail to refold properly ultimately. Thus the less time a cell spends re-cycling poor refolder proteins the more time available to produce usable refolded proteins. See, for example, Trombetta et al., 8 *Curr. Opin. Struct. Biol.* 587–92 (1998).

If a single DNA construct of interest has been synthesized, it can be integrated into an expression vector and transfected into an appropriate host cell for protein expression. Useful prokaryotic host cells include, but are not limited to, *E. coli*, and *B. Subtilis*. Useful eukaryotic host cells include, but are not limited to, yeast cells, insect cells, myeloma cells, fibroblast 3T3 cells, monkey kidney or COS cells, chinese hamster ovary (CHO) cells, mink-lung epithelial cells, human foreskin fibroblast cells, human glioblastoma cells, and teratocarcinoma cells. Alternatively, synthetic genes may be expressed in a cell-free system such as the rabbit reticulocyte lysate system.

The vector additionally can include various sequences to promote correct expression of the recombinant protein, including transcriptional promoter and termination sequences, enhancer sequences, preferred ribosome binding site sequences, preferred mRNA leader sequences, preferred protein processing sequences, preferred signal sequences for protein secretion, and the like. The DNA sequence encoding the gene of interest also can be manipulated to remove potentially inhibiting sequences or to minimize unwanted secondary structure formation. The modified proteins of the present invention also may be expressed as fusion proteins. After being translated, the protein can be purified from the cells themselves or recovered from the culture medium and then cleaved at a specific protease site if so desired.

For example, if the gene is to be expressed in *E. coli*, it is cloned into an appropriate expression vector. This can be accomplished by positioning the engineered gene downstream of a promoter sequence such as Trp or Tac, and/or a gene coding for a leader peptide such as fragment B of protein A (FB). During expression, the resulting fusion proteins accumulate in refractile bodies in the cytoplasm of the cells, and may be harvested after disruption of the cells by French press or sonication. The isolated refractile bodies then are solubilized, and the expressed proteins refolded as taught herein.

If desired, expression of the engineered genes in eukaryolic cells can be achieved. This requires cells and cell lines that are easy to transient, are capable of stably maintaining foreign DNA with an unreatranged sequence, and which have the necessary cellular components for efficient transcription, translation, post-translation modification, and secretion of the protein. In addition, a suitable vector carrying the gene of interest also is necessary. DNA vector design for transfection into mammalian cells should include appropriate sequences to promote expression of the gene of interest as described herein, including appropriate transcription initiation, termination, and enhancer sequences, as well as sequences that enhance translation efficiency, such as the Kozak consensus sequence. Preferred DNA vectors also include a marker gene and means for amplifying the copy number of the gene of interest. A detailed review of the state of the art of the production of foreign proteins in mammalian cells, including useful cells, protein expression-promoting sequences, marker genes, and gene amplification methods, is disclosed in Bendig (1988) *Genetic Engineering* 7:91–127.

The best characterized transcription promoters useful for expressing a foreign gene in a particular mammalian cell are the SV40 early promoter, the adenovirus promoter (AdMLP), the mouse metallothionein-I promoter (mMT-I), the Rous sarcoma virus (RSV) long terminal repeat (LTR), the mouse mammary tumor virus long terminal repeat (MMTV-LTR), and the human cytomegalovirus major intermediate-early promoter (hCMV). The DNA sequences for all of these promoters are known in the art and are available commercially.

The use of a selectable DHFR gene in a dhfr-cell line is a well characterized method useful in the amplification of genes in mammalian cell systems. Briefly, the DHFR gene is provided on the vector carrying the gene of interest, and addition of increasing concentrations of the cytotoxic drug methotrexate, which is metabolized by DHFR, leads to amplification of the DHFR gene copy number, as well as that of the associated gene of interest. DHFR as a selectable, amplifiable marker gene in transfected chinese hamster ovary cell lines (CHO cells) is particularly well characterized in the art. Other useful ampliftable marker genes include the adenosine deaminase (ADA) and glutamine synthetase (GS) genes.

The choice of cells/cell lines is also important and depends on the needs of the experimenter. COS cells provide high levels of transient gene expression, providing a useful means for rapidly screening the biosynthetic constructs of the invention. COS cells typically are transfected with a simian virus 40 (SV40) vector carrying the gene of interest. The transfected COS cells eventually die, thus preventing the long term production of the desired protein product. However, transient expression does not require the time consuming process required for the development of a stable cell line, and thus provides a useful technique for testing preliminary constructs for binding activity.

A particular advantage of the methods and biosynthetic recombinant or chemosynthetic proteins of the instant invention is that they are well suited for use in yeast and bacterial cell systems such as *E. coli* and other systems where overexpression results in formation of inclusion bodies from which the proteins must be resolubilized and refolded in vitro. Even though TGF-β superfamily member protein mutants can be made in mammalian cells, some designed protein constructs and mutants appear to be unstable in mammalian cells and can only be made, at the current slate of the art, by using bacterial cells and refolding the mutants in vitro. Detailed descriptions of the proteins useful in the practice of this invention, including how to make, use and test them for osteogenic activity, are disclosed in numerous publications, including U.S. Pat. Nos. 5,266,683 and 5,011,691, the disclosures of which are incorporated by reference herein, as well as in any of the publications recited herein, the disclosures of which are incorporated herein by reference.

Briefly, the mutant forms of the present invention can be expressed and produced in bacteria and yeast using standard, well-known methods. Full-length mature forms or shorter sequences defining only the C-terminal seven cysteine domain can be provided to the host cell. It may be preferred to modify the N-terminal sequences to optimize bacterial expression. For example, the preferred form of native OP-1 for bacterial expression is the sequence encoding the mature, active sequence (residues 293–431 of SEQ ID NO: 39) or a fragment thereof encoding the C-terminal seven cysteine domain (e.g., residues 330–431 of SEQ ID NO: 39). A methionine can be introduced at position 293, replacing the native serine residue, or it can precede this serine residue. Alternatively, a methionine can be introduced anywhere within the fast thirty-six residues of the natural sequence (residues 293–329), The DNA sequence further can be modified at its N-terminus to improve purification, for example, by adding a "hexa-His" tail to assist purification on an IMAC column; or by using a FB leader sequence, which facilitates purification on an IgG/column. These and other methods are well described and well known in the art. Other bacterial species and/or proteins may require or benefit from analogous modifications to optimize the yield of the mutant BMP obtained therefrom. Such modifications are well within the level of ordinary skill in the art and are not considered material aspects of the invention.

The synthetic nucleic acids preferably are inserted into a vector suitable for overexpression in the host cell of choice. Any expression vector can be used, so long as it is capable of directing the expression of a heterologous protein such as a BMP in the host cell of choice. Useful vectors include plasmids, phagemids, mini chromosomes and YACs, to name a few. Other vector systems are well known and characterized in the art. The vector typically includes a replicon, one or more selectable marker gene sequences, and means for maintaining a high copy number of the vector in the host cell. Well known selectable marker genes include antibiotics like ampicillin, tetracycline and the like, as well as resistance to heavy metals. Useful use with an auxotrophic yeast mutant host. In addition, the vector also includes a suitable promoter sequence for expressing the gene of interest and which may or may not be inducible, as desired, as well as useful transcription and translation initiation sites, terminators, and other sequences that can maximize transcription and translation of the gene of interest. Well characterized promoters particularly useful in bacterial cells include the lac, lac, trp, and tpp promoters, to name a few. Promoters useful in yeast include ADHI, ADHII, or PHO5 promoter, for example.

(c) Refolding Considerations

Proteins produced by *E-coli* for example, are first isolated from inclusion bodies, and then solubilized using a denaturant or chaotropic agent such as guanidine HCl or area, preferably in the range of about 4–9 M and at an elevated temperature (e.g., 25–37° C.) and/or basic pH (8–10). Alternatively, the proteins can be solubilized by acidification, e.g., with acetic acid or trifluoroacetic acid, generally at a pH in the range of 1.4. Preferably, a reducing agent such as β-mercaptoethanol or dithiothreitol (DTT) is used in conjunction with the solubilizing agent. The solubilized heterologous protein can be purified further from solubilizing chaotropes by dialysis and/or by known chromatographic methods such as size exclusion chromatography, ion exchange chromatography, or reverse phase high performance liquid chromatography (RP-HPLC), for example.

In accordance with the present invention, a solubilized mutant can be refolded as follows. The dissolved protein is diluted in a refolding medium, typically a Tris-buffered medium having a pH in the range of about pH 5.0–10.0, preferably in the range of about pH 6–9 and one which includes a detergent and/or chaotropic agent. Useful commercially available detergents can be ionic, nonionic, or zwitterionic, such as NP40 (Nonidet 40), CHAPS (such as 3-[(3-cholamidopropyl) dimethylammonio]-1-propanesulfate, digironin, deoxycholate, or N-octyl glucoside. Useful chaotropic agents include guanidine; urea, or arginine. Preferably the chaotropic agent is present at a concentration in the range of about 0.1–10M, preferably in the range of about 0.5–4M. When CHAPS is the detergent, it preferably comprises about 0.5–5% of the solution, more preferably about 1–3% of the solution. Preferably the solution also includes a suitable redox system such as the oxidized and reduced forms of glutathione, DTT, β-mercaptoethanol, β-mercaptomethanol, cysteine or cystamine, to name a few. Preferably, the redox systems are present at ratios of reductant to oxidant in the range of about 1:1 to about 5:1. When the glutathione redox system is used, the ratio of reduced glutathione to oxidized glutathione is preferably is in the range of about 0.5 to 5; more preferably 1 to 1; and most preferably 2 to 1 of reduced forth to oxidized form. Preferably the buffer also contains a salt, typically NaCl, present in the range of about 0.25M–2.5M, preferably in the range of about 0.5–1.5M, most preferably in the range of about 1M. One skilled in the an will recognize that the above conditions and media may be optimized using no more than routine experimentation. Such variations and modifications are within the scope of the present invention.

Preferably the protein concentration for a given refolding reaction is in the range of about 0.001–1.0 mg/ml, more preferably it is in the range of about 0.05–0.25 mg/ml, most preferably in the range of about 0.075–0.125 mg/ml. As will be appreciated by the skilled artisan, higher concentrations tend to produce more aggregates. Where heterodimers are to be produced (for example an OP-1 BMP-2 or BMP-2 IBMP-6 heterodimer) preferably the individual proteins are provided to the refolding buffer in equal amounts.

Typically, the refolding reaction takes place at a temperature range from about 4° C. to about 25° C. More preferably, the refolding reaction is performed at 4° C. and allowed to go to completion. Refolding typically is complete in about one to seven days, generally within 16–72 hours or 24–48 hours, depending on the protein. As will be appreciated by the skilled artisan, rates of refolding can vary by protein, and longer and shorter refolding times are contemplated and within the scope of the present invention. As used herein, a "good refolder" protein is one where at least approximately 10% of the protein, more preferably at least approximately 20% and even more preferably at least approximately 25%, and most preferably greater than 25%, is refolded following a folding reaction when compared to the total protein in the refolding reaction, as measured by any of the refolding assays described herein and without requiring further purification. For example, native BMPs that are considered in the art to be "good refolder" proteins include BMP-2, CDMP-1, CDMP-2 and CDMP-3. BMP-3 also refolds reasonably well. In contrast, a "poor refolder" protein yields less than 1% of optimally-folded protein When attributes are optimally mixed-and-matched as disclosed herein, certain embodiments can yield more than approximately 25% protein in an optimal re-folded state.

2. Summary of Assays for Screening, Binding and Testing of Biological Activity

Irrespective of which protein expression, harvesting and, folding methodologies are used, certain of the mutant proteins can bind preferentially to a preselected receptor and can now be identified using standard methodologies, i.e., ligand/receptor binding assays, well known, and thoroughly documented in the art, See for example: Legerski et al. (1992) *Biochem. Biophys. Res. Comm.* 183: 672–679; Frakar et al. (1978) *Biochem. Biophys. Res. Comm* 80:849–857; Chio et al, (1990) *Nature* 343: 266–269; Dahlman et al. (1988) *Biochem* 27: 1813–1817; Strader et al. (1989) *J. Biol. Chem.* 264, 13572–13578; and D'Dowd et al. (1988) *J. Biol. Chem.* 263: 15985–15992.

Typically, in a ligand/receptor binding assay, the native or parent TGF-β superfamily member of interest having a known, quantifiable affinity for a preselected receptor is labeled with a detectable moiety, for example, a radiolabel, a chromogenic label, or a fluorogenic label. Aliquots of purified receptor, receptor binding domain fragments, or cells expressing the receptor of interest on their surface are incubated with the labeled TGF-β superfamily member in the presence of various concentrations of the unlabeled mutant protein. The relative binding affinity of a candidate mutant may be measured by quantitating the ability of the mutant to inhibit the binding of the labeled TGF-β superfamily member with the receptor. In performing the assay, fixed concentrations of the receptor and the TGF-β superfamily member are incubated in the presence and absence of unlabeled chimera. Sensitivity may be increased by pre-incubating the receptor with the mutant before adding the labeled template TGF-β superfamily member. After the labeled competitor has been added, sufficient time is allowed for adequate competitor binding, and then free and bound labeled superfamily members are separated from one another, and one or the other measured.

Labels useful in the practice of the screening procedures include radioactive labels, i.e., $^{125}I$, $^{131}I$, $^{111}In$ or $^{77}Br$, chromogenic labels, spectroscopic labels such as those disclosed in Haughland (1994) "*Handbook of Fluorescent and Research Chemicals* 5 ed." by Molecular Probes, Inc., Eugene, Oreg., or conjugated enzymes having high turnover rates, i.e., horseradish peroxidase, alkaline phosphatase, or β-galactosidase, used in combination with chemiluminescent or fluorogenic substrates.

The biological activity, namely the agonist or antagonist properties of the resulting mutant constructs can subsequently be characterized using conventional in vivo and in vitro assays that have been developed to measure the biological activity of any TGF-β superfamily member. It is appreciated, however, the type of assay used will depend on the TGF-β superfamily member upon which the mutant is based. For example, mutant constructs based upon natural OP-1 protein may be assayed using any of the biological assays that have been developed to date for measuring OP-1 activity, see, for example, the exemplification's set forth below.

Optimally refolded dimeric proteins readily can be assessed using any of a number of well known and well characterized assays. In particular, any one or more of three assays, all well known and well described in the art, and further described below can be used to advantage.

Useful refolding assays include one or more of the following. First, the presence of dimers can be detected visually either by standard SDS-PAGE in the absence of a reducing agent such as DTT or by HPLC (e.g., C18 reverse phase HPLC). Dimeric proteins of the present invention have an apparent molecular weight in the range about 28–36 kDa, as compared to monomeric subunits, which have an apparent molecular weight of about 14–18 kDa. The dimeric protein can readily be visualized on an electrophoresis gel by comparison to commercially available molecular weight standards. The dimeric protein also elutes from a C18 RP HPLC (45–50% acetonitrile: 0.1%TFA) at about 19 minutes (mammalian produced hOP-1 elutes at 18.95 minutes). A second assay evaluates the presence of dimer by its ability to bind to hydroxyapatite. Optimally-folded dinner binds a hydroxyapatite column well in pH7, 10 mM phosphate, 6M urea, and 0.1–0.2M NaCl (dimer elutes at 0.25 M NaCl) as compared to monomer, which does not bind substantially at those concentrations (monomer elutes at 0.1M NaCl). A third assay evaluates the presence of dimer by the protein's resistant to trypsin or pepsin digestion. The folded dimeric species is substantially resistant to both enzymes, particularly trypsin, which cleaves only a small portion of the N-terminus of the mature protein, leaving a biologically active dimeric species only slightly smaller in size than the untreated dimer (each monomer in 22 amino acids smaller after trypsin cleavage). By contrast, the monomers and misfolded dinners are substantially degraded. In the assay, the protein is subjected to an enzyme digest using standard conditions, e.g., digestion in a standard buffer such as 50 mM Tris buffer, pH 8, containing 4 M urea, 100 mM NaCl, 0.3% Tween-80 and 20 mM methylamine. Digestion is allowed to occur at 37° C. for on the order of 16 hours, and the product visualized by any suitable means, preferably SDS-PAGE.

The biological activity of the refolded mutant proteins, for example BMPs, readily can be assessed by any of a number of means as described below. For example, the protein's ability to induce endochondral bone formation can be evaluated using the well characterized rat subcutaneous bone assay, described in detail below. In the assay bone formation is measured by histology, as well as by alkaline phosphatase and/or osteoclacin production. In addition, osteogenic proteins having high specific bone forming activity, such as OP-1, BMP-2, BMP-4, BMP-5 and BMP-6, also induce alkaline phosphatase activity in an in vitro rat osteoblast or osteosarcoma cell-based assay. Such assays are well described in the art and are detailed herein below. See, for example, Sabokdar et al. (1994) *Bone and Mineral* 27:57–67.; Knutsen et al. (1993) *Biochem. Biophys. Res. Commun.* 194:1352–1358; and Maliakal et al. (1994) *Growth Factors* 1:227–234). By contrast, osteogenic proteins having low specific bone forming activity, such as CDMP-1 and CDMP-2, for example, do not induce alkaline phosphatase activity in the cell based osteoblast assay. The assay thus provides a ready method for evaluating biological activity of BMP mutants. For example, CDMP-1, CDMP-2 and CMDP-3 all are competent to induce bone formation, although with a lower specific activity than BMP-2, BMP-4, BMP-5, BMP-6 or OP-1. Conversely, BMP-2, BMP-4, BMP-5, BMP-6 and OP-1 all can induce articular cartilage formation, albeit with a lower specific activity than CDMP- 1, CDMP-2 or CDMP-3. Accordingly, a CDMP mutant, designed and described herein to be a mutant competent to induce alkaline phosphatase activity in the cell-based assay, is expected to demonstrate a higher specific bone forming activity in the rat animal bioassay. Similarly, an OP-1 mutant designed and described herein to be containing a substitution present in a corresponding position of a CDMP-1, CDMP-2 or CDMP-3 protein, is competent to induce bone in the rat assay but not to induce alkaline phosphatase activity in the cell based assay, and thus is expected to have a higher specific articular cartilage inducing activity in an in vivo articular cartilage assay. As described herein below, a suitable in vitro assay for CDMP activity utilizes mouse embyronic osteoprogenitor or carcinoma cells, such as ATDC5 cells. See Example 6, below.

TGF-β activity can be readily evaluated by the protein's ability to inhibit epithelial cell growth. A useful, well characterized in vitro may utilizes mink lung cells or melanoma cells. See Example 7. Other assays for other members of the TGF-β superfamily are well described in the literature and can be performed without undue experimentation.

3. Formulation and Bioactivity

The resulting mutant proteins can be provided to an individual as part of a therapy to enhance, inhibit, or otherwise modulate in vivo events, such as but not limited to, the binding interaction between a TGF-β superfamily member and one or more of its cognate receptors. The constructs may be formulated in a pharmaceutical composition, as described below, and may be administered in morphogenic effective amounts by any suitable means, preferably directly or systematically, e.g., parentally or orally. Resulting DNA constructs encoding preferred mutant proteins can also be administered directly to a recipient for gene therapeutic purposes; such DNAs can be administered with or without carrier components, or with or without matrix components. Alternatively, cells transferred with such DNA constructs can be implanted in a recipient. Such materials and methods are well-known in the art.

Where any of the constructs disclosed here are to be provided directly (e.g., locally, as by injection, to a desired tissue site), or parentally, such as by intravenous, subcutaneous, intramuscular, intraorbital, ophthalmic, intraventricular, intracranial, intracapsular, intraspinal, intracisternal, intraperitoneal, buccal, rectal, vaginal, intranasal or by aerosol administration, the therapeutic composition preferably comprises part of an aqueous solution. The solution preferably is physiologically acceptable so that in addition to delivery of the desired construct to the patient, the solution does not otherwise adversely affect the patient's electrolyte and volume balance. The aqueous medium for the therapeutic molecule thus may comprise, for example, normal physiological saline (0.9% NaCl, 0.15M), pH 7–7.4 or other pharmaceutically acceptable salts thereof.

Useful solutions for oral or parenteral administration may be prepared by any of the methods well known in the pharmaceutical art, described, for example, in *Remington's Pharmaceutical Sciences*, (Gennaro, A., ed.), Mack Pub., 1990. Formulations may include, for example, polyalkylene glycols such as polyethylene glycol, oils of vegetable origin, hydrogenated naphthalenes, and the like. Formulations for direct administration, in particular, may include glycerol and other compositions of high viscosity. Biocompatible, preferably bioresorbable polymers, including, for example, hyaluronic acid, collagen, tricalcium phosphate, polybutyrate, polylactide, polyglycolide and lactide/glycolide copolymers, may be useful excipients to control the release of the morphogen in vivo.

Other potentially useful parenteral delivery systems for these therapeutic molecules include ethylene-vinyl acetate copolymer particles, osmotic pumps, implantable infusion systems, and liposomes. Formulations for inhalation administration may contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally.

Finally, therapeutic molecules may be administered alone or in combination with other molecules known to effect tissue morphogenesis, i e., molecules capable of tissue repair and regeneration and/or inhibiting inflammation. Examples of useful cofactors for stimulating bone tissue growth in osteoporotic individuals, for example, include but are not limited to, Vitamin $D_3$, calcitonin, prostaglandins, parathyroid hormone, dexamethasone, estrogen and IGF-I or IGF-II. Useful cofactors for nerve tissue repair and regeneration may include nerve growth factors. Other useful cofactors include symptom-alleviating cofactors, including antiseptics, antibiotics, antiviral and antifungal agents and analgesics and anesthetics.

Therapeutic molecules further can be formulated into pharmaceutical compositions by admixture with pharmaceutically acceptable nontoxic excipients and carriers. As noted above, such compositions may be prepared for parenteral administration, particularly in the form of liquid solutions or suspensions; for oral administration, particularly in the form of tablets or capsules; or intranasally, particularly in the form of powders, nasal drops or aerosols. Where adhesion to a tissue surface is desired the composition may include the biosynthetic construct dispersed in a fibrinogen-thrombin composition or other bioadhesive such as is disclosed, for example in PCT US91/09275, the disclosure of which is incorporated herein by reference. The composition then may be painted, sprayed or otherwise applied to the desired tissue surface. The compositions can be formulated for parenteral or oral administration to humans or other mammals in therapeutically effective amounts, e.g., amounts which provide appropriate concentrations of the morphon to target tissue for a time sufficient to induce the desired effect.

Where the therapeutic molecule comprises part of a tissue or organ preservation solution, any commercially available preservation solution may be used to advantage. For example, useful solutions known in the art include Collins solution, Wisconsin solution, Belzer solution, Eurocollins solution and lactated Ringer's solution. A detailed description of preservation solutions and useful components may be found, for example, in U.S. Pat. No. 5,002,965, the disclosure of which is incorporated herein by reference.

It is contemplated that some of the protein constricts, for example those based upon members of the Vg/dpp subgroup, will also exhibit high levels of activity to vivo when combined with a matrix. See for example, U.S. Pat. No. 5,266,683 the disclosure of which is incorporated by reference herein. The currently preferred matrices are xenogenic, allogenic or autogenic in nature. It is contemplated, however, that synthetic materials comprising polylactic acid, polyglycolic acid, polybutyric acid, derivatives and copolymers thereof can also be used to generate suitable matrices. Preferred synthetic and naturally derived matrix materials, their preparation, methods for formulating them with the morphogenic proteins of the invention, and methods of administration are well known in the an and so are not discussed in detailed herein. See for example, U.S Pat. No. 5,266,683, the disclosure of which is herein incorporated by reference. It is further contemplated that binding to, adherence to or association with a matrix or the metal surface of a prosthetic device is an attribute that can be altered using the materials and methods disclosed herein. For example, devices comprising a matrix and an osteoactive construct of the present invention having enhanced matrix-adherent properties can be used as a slow-release device. The skilled artisan will appreciate the variation and manipulations now possible in light of the teachings herein.

As will be appreciated by those skilled in the art, the concentration of the compounds described in a therapeutic composition will vary depending upon a number of factors, including the morphogenic effective amount to be administered, the chemical characteristics (e.g., hydrophobicity) of the compounds employed, and the route of administration. The preferred dosage of drug to be administered also is likely to depend on such variables as the type and extent of a disease, tissue loss or defect, the overall health status of the particular patient, the relative biological efficacy of the compound selected, the formulation of the compound, the presence and types of excipients in the formulation, and the route of administration. In general terms, the therapeutic molecules of this invention may be provided to an individual where typical doses range from about 10 ng/kg to about 1 g/kg of body weight per day; with a preferred dose range being from about 0.1 mg/kg to 100 mg/kg of body weight.

II. SPECIFIC MODIFIED PROTEIN MUTANTS

Several general types of constructs were prepared and evaluated to improve TGF-β superfamily member protein folding with manipulations of the f2 sub-domain. As referred to herein, the f2 sub-domain region starts after the double Cys (see Table 2, residues 1–31). The base/neck region of the f2 sub-domain consists of residues 1–10 and 22–31.

Generally, the types of constructs contemplated by the present invention include mutants in which: (1) the C-terminal residue (generally residue number 35) is replaced with Arg, Ser, Leu, Ala, or Ile; (2) the number of hydrophilic residues in the f2 region is increased; (3) the number of acidic residues in the base region of the f2 sub-domain is increased, typically by using Glu or Asp as a substitute for a basic or amide residue at least one of positions 4, 6, 9, 25, 26, and 30; (4) the number of hydroxyl-group carrying polar residues is increased, typically by replacing at least one basic residue or amide-group carrying hydrophilic residue in the base region (positions 4, 6, 9, 25, 26, and 30) with Ser or Thr; (5) all or part of the f2 region is put onto a good refolder such as BMP-2 or CDMP-2; or (6) part(s) of the f2 domain is exchanged for part(s) of an f2 sub-domain from a good folder. The skilled artisan will appreciate that these specific residues are not limiting and provided as exemplary residues.

The teachings of the present invention may also be combined with the modifications described in copending applications, the disclosures of which are incorporated herein by reference.

According to the present invention, the attributes of native BMPs or other members of the TGF-β superfamily of proteins, including heterodimers and homodimers thereof, are altered by modifying the f2 subdomain of a native protein to alter one or more biological properties of a BMP or TGF-β superfamily member. As a result of this discovery, it is possible to design, TGF-β superfamily proteins that (1) are expressed recombinantly in prokaryotic or eukaryotic cells synthesized using polypeptide or nucleotide synthesizers; (2) have altered folding attributes; (3) have altered solubility under neutral pHs, including but not limited to physiologically compatible conditions; (4) have altered isoelectric points; (5) have altered stability; (6) have an altered tissue or receptor specificity; (7) have a re-designed, altered biological activity; and/or (8) have altered binding or adherence properties to solid surfaces, such as but not limited to, biocompatible matrices or metals. Thus, the present invention can provide mechanisms for designing quick-release, slow-release and/or timed-release formulations containing a preferred protein construct. Other advantages and features will be evident from the teachings below. Moreover, making use of the discoveries disclosed herein, modified proteins having altered surface-binding/surface-adherent properties can be designed and selected. Surfaces of particular significance include, but are not limited to, solid surfaces which can be naturally-occurring such as bone; or porous particulate surfaces such as collagen or other biocompatible matrices; or the fabricated surfaces of prosthetic implants, including metals. As contemplated herein, virtually any surface can be assayed for differential binding of constructs. Thus, the present invention embraces a diversity of functional molecules having alterations in their surface-binding/surface-adherent properties, thereby rendering such constructs useful for altered in vivo applications, including slow-release, fast-release and/or timed-release formulations.

The skilled artisan will appreciate that mixing-and-matching any one or more the above-recited attributes provides specific opportunities to manipulate the uses of customized proteins (and DNAs encoding the same). For example, the attribute of altered stability can be exploited to manipulate the turnover of a protein in vivo, Moreover, in the case of proteins also having attributes such as altered re-folding and/or function, there is likely an interconnection between folding, function and stability. See, for example, Lipscomb et al., 7 *Protein Sci*. 765–73 (1998); and Nikolova et al., 95 *Proc. Natl. Acad. Sci. USA* 14675–80 (1998). For purposes of the present invention, stability alterations can be routinely monitored using well-known techniques of circular dichroism other indices of stability as a function of denaturant concentration or temperature. One can also use routine scanning calorimetry. Similarly, there is likely an interconnection between any of the foregoing attributes and the attribute of solubility. In the case of solubility, it is possible to manipulate this attribute so that a protein construct is either more or less soluble under physiologically-compatible and it consequently diffuses readily or remains localized, respectively, when administered in vivo.

In addition to the aforementioned uses of protein constructs with altered attributes, those with altered stability can also be used to practical advantage for shelf-life, storage and/or shipping considerations. Furthermore, on a related matter, altered stability can also directly affect dosage considerations thereby, for example, reducing the cost of treatment.

A particularly significant class of constructs are those having altered binding to solubilized carriers or excipients. By way of non-limiting example, an altered BMP having enhanced binding to a solubilized carrier such as hyalmonic acid permits the skilled artisan to administer an injectable formulation at a defect site without loss or dilution of the BMP by either diffusion or body fluids. Thus localization is maximized. The skilled artisan will appreciate the variations made possible by the instant teachings. Similarly, another class of constructs having altered binding to body/tissue components can be exploited. By way of non-limiting example, an altered BMP having diminished binding to an in-situ inhibitor can be used to enhance repair of certain tissues in vivo, It is well known in the art, for example, that cartilage tissue is associated with certain proteins found in body fluids and/or within cartilage per se that can inhibit the activity of native BMPs. Chimeric constructs with altered binding properties, however, can overcome the effects of these in-situ inhibitors thereby enhancing repair, etc. The skilled artisan will appreciate the variations made possible by the instant teachings.

Mutants of OP-1, a TGF-β superfamily member protein, may be any of the following, including conservative variants thereof, where the number indicates the residue position of the mutation, followed by the amino acid residue replaced (single letter code) followed by an arrow and the single letter code of the substituting residue.

OP-1 (4Q>E); OP-1 (6N>S); OP-1 (25R>E); OP-1 (26N>D); OP-1 (4Q>E 6N>S); OP-1 (30R>E); OP-1 (25R>E 26N>D); OP-1 (4Q>E 25R>E); OP-1 (4Q>E 30R>E); OP-1 (25R>E 26N>D); OP-1 (25R>E 30R>E); OP-1 (26N>D 30R>E); OP-1 (4Q>E 26N>D 30R>E); OP-1 (4Q>E 26N>D); OP-1 (4Q>E 25R>E 26N>D), as well an any of these mutants with the additional substitution: 35H>R (position 431 in SEQ ID NO: 39).

In nomenclature that encompasses SEQ ID NO: 39, the OP-1 mutant is anyone of the following:

OP-1 (400Q>E); OP-1 (402N>S), OP-1 (421R>E); OP-1 (422N>D); OP-1 (400Q>E 402N>S); OP-1 (426R>E); OP-1 (421R>E 422N>D); OP-1 (400Q>E 421R>E); OP-1 (400Q>E426R>E); OP-1 (421R>E 422N>D); OP-1 (421R>E 426R>E); OP-1 (422N>D 426R>E); OP-1 (400Q>E 422N>D 426R>E); OP-1 (400Q>E 422N>D); OP-1 (400Q>E 421R>E 422N>D), as well as any of these mutants with the additional substitution: 431H>R.

Mutants of other TGF-β superfamily member proteins may also contain substitutions occurring at least at one of the positions 4, 6, 9, 25, 26, 30 in a poor refolder protein including variants and chimerics thereof, among any of: BMP-5 (SEQ ID NO: 5), BMP-6 (SEQ ID NO: 6), OP-2 (SEQ ID NO: 26), OP-3 (SEQ ID NO: 27),60A (SEQ ID NO: 1), Vg1 (SEQ ID NO: 35), DPP (SEQ ID NO: 12), GDF-1 (SEQ ID NO: 13), GDF-3 (SEQ ID NO: 14), GDF-5 (SEQ ID NO: 15), GDF-6 (SEQ ID NO: 16), GDF-7 (SEQ ID NO: 17), BMP-3 (SEQ ID NO: 3), CDMP-2 (SEQ ID NO: 10), BMP-10 (SEQ ID NO: 8), GDF-9 (SEQ ID NO: 18), (InhibinA (SEQ ID NO: 20), Inhibin βA (SEQ ID NO: 21), Inhibin βB (SEQ ID NO: 22), inhibin βC (SEQ ID NO: 23), BMP-11 (SEQ ID NO: 9). In addition, any of these mutants may also include a substitution of the C-terminal residue to any one of arginine, serine, leucine, isoleucine or alanine.

Substitutions may also occur at least at one of the following positions 4, 6, 9, 24, 25, 29 in any of the other TGF-β superfamily member proteins (SEQ ID NOs: 29–33) or NODAL (SEQ ID NO: 25); at least at one of the following positions 4, 6, 9, 25, 26, 30 in UNIVIN (SEQ ID NO: 34); and at least at one of the following positions 4, 6, 9, 26, 27, and 31 in BMP-9 (SEQ ID NO: 7), and Dorsalin (SEQ ID NO: 11).

The TGF-β superfamily member mutants are created through recombinant, chemosynthetic or biosynthetic means, which include using nucleic acid molecules, including DNA, RNA and PNA (peptide-nucleic acid) molecules, encoding any of the substituted TGF-β superfamily member proteins of the invention as well as native or modified amino acids. The substitution can be in the form of replacing a non-acidic residue with an acidic residue, such a s glutamic acid or aspartic acid, atone or more of these positions. Alternatively, the substitution can also include replacing an amino acid with serine or threonine at one or more of these positions in the peptide sequence. Substitutions may also comprise replacing the C-terminal residue with arginine. This can be done by substituting the nucleotide in the triplet to create any of the following: AGA, AGG, CGG, CGC, CGA, or CGU. A TGF-β superfamily, member mutant may contain any one or any combination of the above substitutions.

FIGS. 4A and 4B are schematic drawings of various mutants and their refolding and biological activity properties. In the figure, the thick solid line represents OP-1 (residues 330–431 of SEQ ID NO: 39), the thin solid line represents CDMP-2 /GDF-6 (SEQ ID NO: 84) or GDF-5 (SEQ ID NO: 83), and the hatched line represents BMP-2 (SEQ ID NO: 49). Mutant constructs are presented in FIG. 4A and individual sequence mutants are presented in FIG. 4B. In the figure, individual residue changes are indicated by the substituting residue in the figure. The residue numbering is as described above, counting from the first residue after the cysteine doublet in finger 2. For example, mutant H2233 is OP-1(25R>E 26N>D 30R>E 35H>R). Similarly, mutant H2447 has all the changes in H2233 and, in addition, has 1A>V 4Q>E 6N>S. Mutant H2433 is OP-1(4Q>K 35H>R), and mutant H2456 is OP-1(4Q>E 6N>S 25R>E 26N>D 30R>E35H>R).

Table 2 provides the finger 2 sub-domain sequences of various osteogenic proteins and mutant variant constructs thereof, beginning with the first residue following the cysteine doublet, and which correspond to native sequences as described below. In the table, residues that differ from OP-1 are underlined. One chimeric construct is H2421 residues 1–20 from GDF-5 (SEQ ID NO: 15) and residues 21–34 from OP-1 (SEQ ID NO: 39). Another construct is H2406: res. 1–10 from CDMP, (CMP-2) (SEQ ID NO: 10) and res. 11–34 from OP-1 (SEQ ID NO: 39). Another construct is H2410: res. 1–35 from BMP-2 (SEQ ID NO: 2). Another construct is H2418: res. 1–7 as well as res. 25–35 from GDF-6 (SEQ ID NO: 16) and res. 8–24 from OP-1 (SEQ ID NO: 39). All other constructs correspond in sequence to OP-1 (SEQ ID NO: 39) with one or more individual amino acid changes as indicated by the bolded residues, corresponding to one or more of positions 1, 4, 6, 7, 25, 26, 30, 31, 35 in the table and residues 397, 400, 402, 403, 421, 422, 426 and 431 in SEQ ID NO: 39.

TABLE 2

Finger-2 Sequence

|  | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |  |  |
|---|---|---|---|---|---|---|---|---|---|---|---|---|---|---|---|---|---|---|---|---|---|---|---|---|---|---|---|---|---|---|---|---|---|
| wtOP1 | CC | A | P | T | Q | L | N | A | I | S | V | L | Y | F | D | D | S | S | N | V | I | L | K | K | Y | R | N | M | V | V | R | A | CGC H |
| BMP-2 | CC | V | P | T | E | L | S | A | I | S | M | L | Y | L | D | E | N | E | K | V | V | L | K | N | Y | Q | D | M | V | V | E | G | CGC R |
| CDMP-2 | CC | V | P | T | K | L | T | P | I | S | I | L | Y | I | D | A | A | N | N | V | V | Y | K | Q | Y | E | D | M | V | V | E | S | CGC R |

TABLE 2-continued

Finger-2 Sequence

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| GDF-5 | CC | V | P | T | R | L | S | P | I | S | I | L | F | I | D | S | A | N | N | V | V | Y | K | Q | Y | E | D | M | V | V | E | S | CGC | R |
| H2177 | CC | A | P | T | Q | L | N | A | I | S | V | L | F | I | D | S | A | N | N | V | V | Y | K | Q | Y | E | D | M | V | V | E | S | CGC | R |
| H2406 | CC | V | P | T | K | L | T | P | I | S | I | L | Y | F | D | D | S | S | N | V | I | L | K | K | Y | R | N | M | V | V | R | A | CGC | R |
| H2421 | CC | V | P | T | R | L | S | P | I | S | I | L | F | I | D | S | A | N | N | V | V | L | K | K | Y | R | N | M | V | V | R | A | CGC | R |
| H2247 | CC | A | P | T | Q | L | N | A | I | S | V | L | Y | F | D | D | S | S | N | V | I | L | K | K | Y | R | N | M | V | V | R | A | CGC | R |
| H2464 | CC | A | P | T | Q | L | S | A | I | S | V | L | Y | F | D | D | S | S | N | V | I | L | K | K | Y | R | N | M | V | V | R | A | CGC | R |
| H2467 | CC | A | P | T | E | L | S | A | I | S | V | L | Y | F | D | D | S | S | N | V | I | L | K | K | Y | R | N | M | V | V | R | A | CGC | R |
| H2234 | CC | A | P | T | Q | L | N | A | I | S | V | L | Y | F | D | D | S | S | N | V | I | L | K | K | Y | E | D | M | V | V | R | A | CGC | R |
| H2233 | CC | A | P | T | Q | L | N | A | I | S | V | L | Y | F | D | D | S | S | N | V | I | L | K | K | Y | E | D | M | V | V | E | A | CGC | R |
| H2457 | CC | V | P | T | E | L | N | A | I | S | V | L | Y | F | D | D | S | S | N | V | I | L | K | K | Y | E | D | M | V | V | E | A | CGC | R |
| H2443 | CC | V | P | T | K | L | T | P | I | S | V | L | Y | F | D | D | S | S | N | V | I | L | K | K | Y | E | D | M | V | V | R | A | CGC | R |
| H2418 | CC | V | P | T | K | L | T | P | I | S | V | L | Y | F | D | D | S | S | N | V | I | L | K | K | Y | E | D | M | V | V | E | S | CGC | R |
| H2447 | CC | V | P | T | E | L | S | A | I | S | V | L | Y | F | D | D | S | S | N | V | I | L | K | K | Y | E | D | M | V | V | E | A | CGC | R |
| H2456 | CC | A | P | T | E | L | S | A | I | S | V | L | Y | F | D | D | S | S | N | V | I | L | K | K | Y | E | D | M | V | V | E | A | CGC | R |
| H2460 | CC | A | P | T | Q | L | S | A | I | S | V | L | Y | F | D | D | S | S | N | V | I | L | K | K | Y | E | D | M | V | V | E | A | CGC | R |
| H2475 | CC | A | P | T | K | L | N | A | I | S | V | L | Y | F | D | D | S | S | N | V | I | L | K | K | Y | E | D | M | V | V | E | A | CGC | R |
| H2449 | CC | A | P | T | E | L | N | A | I | S | V | L | Y | F | D | D | S | S | N | V | I | L | K | K | Y | R | N | M | V | V | R | A | CGC | R |

For each mutant listed herein, refolding was measured using at least one of the parameters described herein (see, e.g., Example 4). All values recited were measured against a known good refolder, e.g., CDMP-2 or BMP-2, which yields approximately at least 25% dimer upon refolding, without additional purification. Values are presented in Table 3 (below) and FIG. 4 as follows: (+++)=>25%; (++)= 5–25%; (+)=1–5%; (+/−)=<1%, where native CDMP-2 and BMP-2 each have a +++ refolding value. Activity was measured in the osteosarcoma cell-based assay, which also is a measure of bone inducing activity. That is OP-1 and BMP-2 can induce alkaline phosphatase activity in this cell-based assay, but CDMP-2 and CDMP-1 do not. Yet, all four proteins are competent to induce the full cascade of morphogenic events resulting in endochondral bone formation in the rat subcutaneous assay (Example 8). In the cell-based assay of Example 5, activity measured is alkaline phosphatase activity, as determined by optical density at 405 nm. The hOP-1 value shown is from mammalian cell-produced protein. "N/A" means "not-tested". Figure values are as follows: (+++)=≧1.2; (++) 0.8–1.2; (+)=0.4–0.8; (+/−)=<0.4, where native hOP-1 has a +++ biological activity value.

TABLE 3

| Mutant | Folding | ROS | Comments |
|---|---|---|---|
| wtOP1 | +/− | N/A | OP-1 is poor refolder |
| BMP-2 | +++ | +++ | natural |
| CDMP-2 | +++ | +/− | good |
| GDF-5 | +++ | +/− | refolders |
| H2177 | + | N/A | OP-1 with 13 GDF-5 derived residues refolds |
| H2406 | +/− | N/A | CDMP-2 with 11 OP-1 derived residues fails |
| H2421 | +/− | N/A | GDF-5 with 6 OP-1 residues fails |
| H2247 | + | +++ | improved folding with C-terminal substitution of H |
| H2464 | + | N/A | |
| H2467 | + | N/A | |
| H2234 | +½ | N/A | better folding with |
| H2233 | ++ | +++ | Additional |
| H2457 | ++½ | +++ | E, D substitutions |
| H2443 | +++ | | best refolding |
| H2418 | +++ | ++ | When also |
| H2447 | +++ | ++ | Substituting |
| H2456 | +++ | ++½ | Upstream |
| H2460 | +++ | ++½ | N by S or T |
| H2475 | ++ | +++ | same substitutions in BMP-5 also improve refolding |

As shown in FIGS. 4A and 4B, replacing the C-terminal residue of OP-1 increases refolding of the protein. Chimeric mutants that substitute heel or finger 1 sub-domains from good refolders but maintain an OP-1 finger 2 do not improve the protein's refolding properties substantially (see, e.g., H2360, H2362, H2331, H2383). However, substituting a finger 2 sub-domain from a good refolder does improve refolding. Mutant morphogens such as H2410, H2389, and H2471 are particularly vivid examples of how morphogen domains may be recombined to produce variant forms of morphogens having new or altered properties or activities. For example, replacing only the base of finger 2 with that of a good refolder (such as CDMP-2), and maintaining the tip region of OP-1 (positions 10–20) maintains the binding specificity of OP-1 in the cell-based assay (H2418), in addition to improving refolding.

Additional modifications were obtained by mutating individual codons to change individual amino acids. Minimizing the changes in the finger 2 base region to one, two or three acidic residue substitutions were all equally good at improving refolding and maintaining OP-1 binding specificity (see e.g., H2447, and H2443 in FIG. 4B and H2456 in Tables 2 and 3). Finally, substituting a hydroxyl group-carrying residue for a positively charged or amide carrying residue also improved refolding (H2456). Also, replacing in H2456 Gln4 of OP-1 with the Glu at position 4 of BMP-2 improved refolding. In addition, the positive charge or proline that precedes the cysteine doublet do not appear to contribute significantly to the protein's refolding properties in vitro, as changing the sequence "KP" that precede the "CC" doublet to "NS" had little or no significant effect.

Additional examples of morphogen modifications are shown in Table 2. In contrast to OP-1, some members of the TGF-β superfamily, such as BMP-2, CDMP-2, and GDF-5, are good refolders, and have an innate capability to refold in a standard protein refolding protocol. Various mutants of the osteogenic subgroup of the TGF-β superfamily member proteins were constructed to determine which amino acid residues can be changed to improve the refolding capability of a poor refolder protein. For example, OP1 was modified in its finger 2 sub-domain to contain 13 amino acids, which are found at corresponding positions in GDF-5. The resultant mutant variant protein of OP-1 exhibited improved refolding capability over the wild type OP-1 protein (see, H2177 in Tables 2 and 3). Likewise, the refolding capability of wild type BMP-5 was improved in a mutant variant in which certain amino acid residues of the finger 2 sub domain were replaced with glutamic acid, aspartic acid, arginine, and alanine (see, H2475 in Tables 2 and 3). In contrast, refolding capability was diminished when CDMP-2 was modified to contain 11 amino acids from the OP-1 finger 2 sub-domain (see, H2406 in Tables 2 and 3), or when GDF-5 was modified to contain 6 amino acids from the OP-1 finger 2 sub-domain (see, H2421 in Tables 2 and 3). The charges in the CDMP-2 mutant H2406 and the GDF-5 mutant H2421 in Table 2 basically recreated a region of the finger 2 sub-domain of OP-1 (see, regions of finger 2 amino acid sequences of H2406 and H2421 in Table 2).

Based on observations of wild type proteins and mutant variants thereof, more selective amino acid residue substitutions were made in the finger 2 sub-domain of OP-1 and evaluated for their effect on refolding. Such a selective finger 2 sub-domain mutagenesis of the OP-1 osteogenic protein is demonstrated by the data in Table 3. Table 2 shows the amino acid sequences the finger 2 sub-domain of various osteogenic proteins and mutant variants thereof. In Table 2, all amino acid residues underlined differ from the corresponding residue in wild type OP-1. Residues not underlined in Table 2 correspond to native amino acid residues found in wild type OP-1. Substituting the C-terminal histidine of OP-1 with an arginine (R, as found in natural goad refolder osteogenic proteins such as CDMP-2, GDF-5, and BMP-2) enhanced refolding capability (see, mutant constructs H2247, H2464, and H2467 in Tables 2 and 3). Increasing the negatively-charged residues in the C-terminal finger 2 sub-domain region of OP-1, for example, by substituting glutamic acid (E) or aspartic acid (D) as found in good refolder osteogenic proteins, enhanced refolding capability (see, for example, H2234, H2233, and H2457 in tables 2 and 3). The best refolders have more negative charges in the C-terminal finger 2 sub-domain and also a relatively high total content of charged residues. Further improvement in refolding capability was also achieved by increasing the number of hydroxyl group-carrying polar residues in the finger 2 sub-domain of OP-1. For example, in addition to the substitutions mentioned above, substituting hydroxyl group-carrying polar amino acid residues serine (S) or threonine (T) for the most upstream asparagine (N) in the finger 2 sub-domain enhanced refolding (see, H2443, H2418, H2447, H2456, and H2460 in tables 2 and 3).

Mutants with good ROS activity such as H2247, H2233, H2457, and H2475 contain the original peptide Leu-Asn-Ala (residues 5, 6, 7). Other OP-1 mutants that fold somewhat better contain the modified peptide Leu-Ser-Ala as found in BMP-2, H2456 and H2460, but these proteins are somewhat less active in the ROS assay. See Table 3. Hence, the asparagine in the Leu-Asn-Ala peptide makes a positive contribution in the ROS assay.

As an additional representative of the OP-1 related BMPs, the BMP-5 mutant H2475 (which is very similar in sequence to OP-1 with 88% identity in the 7 cysteine domain) was expressed. In its unmodified form, BMP-5, just like OP-1, did not refold. After the same changes were introduced in finger-2 that permitted refolding of OP-1, a useful refolding yield was obtained. FIG. 3B shows the BMP-5 nucleotide sequence and its alterations for refolding. In the case of BMP-5, the initial change at the C-terminus, lustidine to arginine, was insufficient for refolding. Therefore, three acidic residues were introduced nearby that had proven beneficial for refolding of OP-1. This was done by splicing BMP-5 with the C-terminal sequence from OP-1, which also introduced the additional serine to alanine change. This construct was tested in a ROS assay and had activity which was equal to or better than the successful OP-1 variants, such as H2471 (mutant OP-1 with CDMP-2 finger 2). CDMP-2, tested as a control, showed no activity.

These modified protein mutants are more soluble than their unmodified counterparts. For example, the mutant H2223, which is mutant H2233 (see Table 2) without the pro-domain and which is established in CHO cells, showed a surprising increase in solubility as compared to mature wild type OP-1. H2223 is an OP-1 mutant with four amino acid substitutions, 25R>E 26N>D 30R>E 35H>R, counting the first residue from the double cysteines. The mutant and wild type morphogens were lyophilized and, subsequently, solubilized in PBS of pH 7.4 or pH 7.0. After 40 hours at room temperature, the samples were spun down to collect any unsolubilized protein and the resulting supernatant was subjected to SDS PAGE analysis. A significant portion of the lyophilized H2223 mutant was solubilized in the PBS buffer, whereas the wild type OP-1 was virtually insoluble in neutral pH. The introduction of charged residues to create mutant TGF-β superfamily proteins appears to improve the solubility of those proteins. One can further expect that this increased solubility could account for the increased activity in the ROS assay as compared to wild type OP-1.

Where charged residues were reversed in their polarity, it affected the isoelectric paint of the protein even though its activity in a ROS assay may not have been changed. The mutants H2456, H2457, and H2460 were refolded, purified and analyzed on an isoelectric focusing gel. These mutants differed by only one or two charged amino acids (located near cysteine 4 and cysteine 5, where heel and finger-2 meet). H2460, which has one less acidic residue than H2456, focused in a more basic range than H2456. Likewise, H2457, which has one less basic residue than H2456, focused in a more acidic range than H2456. The introduction of glutamic acid in place of arginine and the introduction of aspartic acid in place of asparagine resulted in a shift of the isoelectric point to the acidic pH. This may result in improved or altered solubility, which can be desirable as compensation for the lack of glycosylation in bacterially produced protein.

Such charge modifications may also be helpful in the purification of heterodimers. If the two subunits in the heterodimers have different binding affinities due to their net charge, the three species resulting from a mixed refolding experiment (i.e., homodimers of each subunit and the heterodimer) can be easily separated from each other on a column.

Practice of the invention will be still more fully understood from the following examples, which are presented herein for illustration only and should not be construed as limiting the invention in any way.

III. EXAMPLES

Example 1

Synthesis of an Exemplary Mutant Protein of the Present Invention: a BMP Mutant

FIG. 3A shows the nucleotide and corresponding amino acid sequence for the OP-1 C-terminal seven cysteine domain. Knowing these sequences permits identification of useful restriction sites for engineering in mutations by, for example, cassette mutagenesis or the well known method of Kunkel (mutagenesis by primer extension using m13-derived single-stranded templates) or by the well-known PCR methods, including overlap extension. An exemplary mutant of OP-1 is H2460, with 4 amino acid changes in the finger 2 sub-domain and an amino acid change in the last C-terminal amino acid, constructed as described below. It is understood by the skilled artisan that the mutagenesis protocol described is exemplary only, and that other means for creating the constructs of the invention are well-known and well described in the art.

Four amino acid changes were introduced into the OP-1 finger 2 sub-domain sequence by means of standard polymerase chain reactions using overlap extension technique, resulting in OP-1 mutant H2460. The four changes in the finger 2 region were N6>S, R25>E, N26>D and $R_{30}$>E. This mutant also contained a further change, H35>R, of the C-terminal residue. The template for these reactions was the mature domain of a wild type OP-1 cDNA clone, which had been inserted into an E. coli expression vector engineered with an ATG start codon at the beginning of the mature region. The ATG had been introduced by PCR using as forward primer a synthetic oligonucleotide of the following sequence: ATG TCC ACG GGG AGC AAA CAG (SEQ ID NO: 36), encoding M S T G S K Q (SEQ ID NO: 37). The PCR reaction was done in combination with an appropriate back-primer complementary to the 3' coding region of the cDNA.

In order to construct the finger 2 mutant H2460, a PCR fragment encoding the modified finger-2 was made in a standard PCR reaction, using a commercially available PCR kit and following the manufacturer's instructions using as primers synthetic oligonucleotides.

To obtain the N6>S change, a forward primer (primer #1) of the sequence GCG CCC ACG CAG CTC AGC GCT ATC TCC GTC CTC (SEQ ID NO: 70) was used, encoding the amino acid sequence: A P T Q L S A I S V L (SEQ ID NO: 71).

For the changes near the C-terminus, a back-primer, 43 nucleotides long, (primer #2) was used which introduced the R25>E and N26>D and R30>E and C-terminal H35>R changes. This primer lit had the sequence: CTA TCT GCA GCC ACA AGC TTC GAC CAC CAT GTC TTC GTA TTT C (SEQ ID NO: 72) which is the complement of the coding sequence, G AAA TAC GAA GAC ATG GTG GTC GAA GCT TGT GGC TGC AGA TAG (SEQ ID NO: 73) encoding the amino acids: K Y E D M V V E A C G C R stop (SEQ ID NO: 74).

The fragment with finger 2 and C-terminus mutations was then combined with another PCR fragment encoding the upstream part of mature OP-1, with N-terminus, finger-1 and heel sub-domains. The latter PCR fragment, encoding the N-terminus, finger 1 and heel sub-domains was constructed again using an OP-1 expression vector for E. coli as template. The vector contained an OP-1 cDNA fragment, encoding the mature OP-1 protein attached to a T7 promoter and ribosome binding site for expression under control of either a T7 promoter in an appropriate host or under control of a trp promoter. In this T7 expression vector, Pet 3d (Novagen Inc., Madison Wisc.) the sequence between the T7 promoter, at the XbaI site, and the ATG codon of mature OP-1 is as follows: TCTAGAATAATTTTGTTTAACCTTTAAGAAGGAGATATACG ATG (SEQ ID NO: 75).

This second PCR reaction was primed with a forward primer (primer #3) TAA TAC GAC TCA CTA TAG G (SEQ ID NO: 76) which primes in the T7 promoter region and a back primer (primer #4) that overlaps with primer #1 and has the nucleotide sequence GCT GAG CTG CGT GGG CGC (SEQ ID NO: 77), which is the complement of the coding sequence GCG CCC ACC CAG CTC AGC (SEQ ID NO: 78), encoding A P T Q L S (SEQ ID NO: 79).

In a third PCR reaction, the actual overlap extension reaction, portions of the above two PCR fragments were combined and amplified by PCR, resulting in a single fragment containing the complete mature OP-1 region. For this reaction, primer #3 was used as forward primer and a new primer (primer #5) was used as a back-primer with the following sequence GG ATC CTA TCT GCA GCC ACA AGC (SEQ ID NO: 80), which is the complement to coding sequence GCT TGT GGC TGC AGA TAG GAT CC (SEQ ID NO: 81), encoding A C G C R stop (SEQ ID NO: 82). This primer also adds a convenient 3' BamHI site for of inserting the gene into the expression vector.

The resulting fragment bearing the complete mutant gene, resulting from the overlap extension PCR, was cloned into a commercial cloning vector designed for cloning of PCR fragments, such as pCR2.1-topo-TA (Invitrogen Inc., Carlsbad Calif.). The cloned PCR fragment was recovered by restriction digest with XbaI and BamHI and inserted into the XbaI and BamHI sites of a commercially available T7 expression vector such as Pet3d (Novagen Inc., Madison Wisc.).

Example 2

E. coli Expression of an Exemplary Mutant Protein of the Present Invention: Expression of a BMP Mutant Transformed cells were grown in standard SPYE 2YT media, 1:1 ratio, (see, Sambrook et al., for example) at 37° C., under standard culturing conditions. Heterologous protein overexpression typically produced inclusion bodies within 8–48 hours. Inclusion bodies were isolated and solubilized as follows. One liter of culture fluid was centrifuged to collect the cells. The cells in the resulting pellet then were resuspended in 60 ml 25 mM Tris, 10 mm EDTA, pH 8.0 (TE Buffer)+100 μg/ml lysozyme and incubated at 37° C. for 2 hours. The cell suspension was then chilled on ice and sonicated to lyse the cells. Cell lysis was ascertained by microscopic examination. The volume of the lysate was adjusted to approximately 300 ml with TE Buffer, then centrifuged to obtain an inclusion body pellet. The pellet was washed by 2–4 successive resuspensions in TE Buffer and centrifugation. The washed inclusion body pellet was solubilized by denaturation and reduction in 40 ml 100 mM Tris,10 mM EDTA, 6M GuHCl (guanidinium hydrochloride), 250 mM DTT, pH 8.8. Proteins then were pre-purified using a standard, commercially available C2 or C8 cartridge (SPICE cartridges, 400 mg, Analtech, Inc.), Protein solutions were acidified with 2% TFA (trifluoroacetic acid), applied to the cartridge, washed with 0.1%/TFA/10% acetonitrile, and eluted with 0.1%/TFA/70% acetonitrile. The eluted material then was dried down or diluted and fractionated by C4 RP-HPLC.

Example 3

Refolding of an Exemplary Mutant Protein of the Present Invention: a Mutant BMP Dimer Proteins prepared as described above were dried down prior to refolding, or diluted directly into refolding buffer. The preferred refolding buffer used was: 100 mM Tris, 10 mM EDTA, 1 M NaCl, 2% CHAPS, 5 mM GSH (reduced glutathione), 2.5 mM GSSG (oxidized glutathione), pH 8.5. Refoldings (12.5–200 μg protein/ml) were carried out at 4° C for 24–90 hours, typically 36–48 hours, although longer than this (up to weeks) are expected to provide good refolding in some mutants, followed by dialysis against 0.1% TFA, then 0.01% TFA, 50% ethanol. Aliquots of the dialyzed material then was dried down in preparation for the various assays.

Example 4

Purification and Testing of a Refolded Exemplary Mutant Dimer of the Present Invention: a Mutant BMP Dimer

4A. SDS-PAGE, RP HPLC—

Samples were dried down and resuspended in Laemmli gel sample buffer and then electrophoresed in a 15% SDS-polyacrydamide gel. All assays included molecular weight standards and/or purified mammalian cell produced OP-1 for comparison. Analysis of OP-1 dinners was performed in the absence of added reducing agents, while OP-1 monomers were produced by the addition of 100 mM DTT to the gel samples. Folded dimer has an apparent molecular weight in the range of about 30–36 kDa, while monomeric species have an apparent molecular weight of about 14–16 kDa.

Alternatively, samples were chromatographed on a commercially available RP-HPLC, as follows. Samples were dried down and resuspended in 0.1%/TFA/30% acetonitrile. The protein then was applied to a C18 column in 0.1% TFA, 30% acetonitrile and fractionated using a 30–60% acetonitrile gradient in 0.1% TFA. Properly folded dimers elute as a discrete peak at 45–50% acetonitrile; monomers elute at 50–60% acetonitrile.

4B. Hydroxyapatite Chromatography—

Samples were loaded onto a hydroxyapatite column in 10 mM phosphate, 6 M area, pH 7.0 (Column Buffer). Unbound material was removed by washing with column buffer, followed by elution of monomer with Column Buffer +100 mM NaCl. Dimers were eluted with Column Buffer+250 mM NaCl.

4C. Trypsin Digest—

Tryptic digests were performed in a digestion buffer of 50 mM Tris, 4 M urea, 100 mM NaCl, 0.3% Tween 80, 20 mM methylamine, pH 8.0. The ratio of enzyme to substrate was 1:50 (weight to weight). After incubation at 37° C. for 16 hours, 15 $\mu$l of digestion mixture was combined with 5 $\mu$l 4× gel sample buffer without DTT and analyzed by SDS-PAGE. Purified mammalian OP-1 and undigested BMP dinner were included for comparison. Under these conditions, properly folded diners are cleaved to produce a species with slightly faster migration than uncleaved standards, while monomers and mis-folded dialers are completely digested and do not appear as bands in the stained gel.

Example 5

Testing the Altered Attributes of a Mutant Protein of the Present Invention: In vitro Cell-Based Bioassay of Osteogenic Activity

This example demonstrates the bioactivity of certain osteogenic mutant proteins of the invention. Native osteogenic proteins having high specific bone forming activity can induce alkaline phosphatase activity in rat osteoblasts, including rat osteosarcoma cells and rat calveria cells. In the assay rat osteosarcoma or calveria cells were plated onto a multi-well plate (e.g., a 48 well plate) at a concentration of 50,000 osteoblasts per well, in $\alpha$MEM (modified Eagle's medium, Gibco, Inc. Long Island) containing 10% FBS (fetal bovine serum), L-glutamine and penicillin/streptomycin. The cells were incubated for 24 hours at 37° C., at which time the growth medium was replaced with $\alpha$ MEM containing 1% FBS and the cells incubated for an additional 24 hours so that cells were in serum-deprived growth medium at the time of the experiment. Cultured cells then were divided into three groups: (1) wells receiving various concentrations of biosynthetic osteogenic protein; (2) a positive control, such as mammalian expressed hOP-1; and a negative control (no protein or TGF-$\beta$). The protein concentrations tested were in the range of 50–500 ng/ml. Cells were incubated for 72 hours. After the incubation period the cell layer was extracted with 0.5 ml of 1% TritonX-100. The resultant cell extract was centrifuged, 100$\mu$l of the extract was added to 90 $\mu$l of PNPP (paranitrosophenylphosphate)glycerine mixture and incubated for 30 minutes in a 37° C. water bath and the reaction stopped with 100 $\mu$l 0.2 N NaOH. The samples then were tun through a plate reader (e.g., Dynatech MR700) and absorbance measured at 400 nm, using p-nitrophenol as a standard, to determine the presence and amount of alkaline phosphatase activity. Protein concentrations were determined by standard means, e.g., the Biorad method, UV scan or RP HPLC area at 214 nm, Alkaline phosphatase activity was calculated in units/$\mu$g protein, where 1 unit equals 1 nmol p-nitrophenol liberated/30 minutes at 37° C.

Native hOP-1 and BMP2 generate approximately 1.0–1.4 units at between 100–200 ng/ml.

Example 6

Testing the Altered Attributes of a Mutant Protein of the Present Invention: In vitro Cell-Based Bioassay of CDMP Activity

This example demonstrates the bioactivity of certain osteogenic mutants of the invention. Native CDMPs fail to induce alkaline phosphatase activity in rat osteosarcoma cells as used in Example 5, but they do induce alkaline phosphatase activity in the mouse teratocarcinoma cell line ATDC-5, a chondroprogenitor cell line (Atsumi, et al., 1990, *Cell Differentiation and Development* 30: 109). Re-folded mutant constructs that are negative in the rat osteocarcinoma cell assay but positive in the ATDC-5 assay are described as having acquired CDMP-like activity. In the ATDC-5 assay, cells were plated at density of $4 \times 10^4$ in serum-free basal medium (BM; Ham's F-12/DMEM [1:1] with ITS™+ culture supplement [Collaborative Biomedical Products, Bedford, Mass.], alpha-ketoglutarate ($1 \times 10^{-4}$M), ceruloplasmin (0.25 U/ml), cholesterol (5 $\mu$l/ml), phosphatidylethanolamine (2 $\mu$g/ml), alpha-tocopherol acid succinate ($9 \times 10^{-7}$M), reduced glutathione (10 $\mu$g/ml), taurine (1.25 $\mu$g/ml), triodothyronin ($1.6 \times 10^{-9}$M), hydrocortisone ($1 \times 10^{-9}$) (parathyroid hormone ($5 \times 10^{-10}$M), $\beta$-glycerophosphate (10 mM), and L-ascorbic acid 2-sulphate (50 $\mu$g/ml)). CDMP of mutant protein (0–300 ng/ml) was added the next day and the culture medium, including CDMP or mutant protein, replaced every other day, Alkaline phosphatase activity was determined in sonicated cell homogenates after 4, 6 and/or 12 days of treatment. After extensive washing with PBS, cell layers were sonicated in 500 $\mu$l of PBS containing 0.05% Triton-X100. 50–100 $\mu$l aliquots were assayed for enzyme activity in assay buffer (0.1M sodium barbital buffer, pH 9.3) and p-nitrophenyl phosphate as substrate. Absorbance was measured at 400 nm, and activity normalized to protein content measured by Bradford protein assay (bovine senun albumin standard).

Native CDMP-1 and CDMP-2 generated approximately 2–3 units of activity at day 10 at 100 ng/ml. The native OP-1 standard generated approximately 6–7 units of activity at day 10 at 100 ng/ml.

Example 7

Testing the Altered Attributes of a Mutant Protein of the Present Invention: In vitro Cell-Based Bioassay of TGF-β-like Activity

This example demonstrates the bioactivity of certain TGF-β-based mutant proteins of the invention. Native TGF-β proteins can inhibit epithelial cell proliferation. Numerous cell inhibition assays are well described in the art. See, for example, Brown, et. al. (1987) *J. Immunol.* 139:2977, describing a colorimenic assay using human melanoma A375 fibroblast cells, and described herein below. Another assay uses epithelial cells, e.g., mink lung epithelial cells, and proliferative effects are determined by $^3$H-thymidine uptake.

Briefly, in the may the TGF-β biosynthetic mutant is serially diluted in a mull-well tissue plate containing RPMI-1640 medium (Gibco) and 5% fetal calf serum. Control wells receive medium only. Melanoma cells then are added to the well ($1.5 \times 10^4$). The plates then are incubated at 37° C. for about 72 hours in 5% $CO_2$, and the cell monolayers washed once, fixed and stained with crystalviolet for 15 minutes. Unbound stain is washed out and the stained cells then lysed with 33% acetic acid to release the stain (confined to the cell nuclei), and the OD measured at 590 nm with a standard, commercially available photometer to calculate the activity of the test molecules. The intensity of staining in each well is directly related to the number of nuclei. Accordingly, active TGF-β molecules are expected to stain lighter than inactive compounds or the negative control well.

In another assay, mink lung cells are used. These cells grow and proliferate under standard culturing conditions, but are arrested following exposure to TGF-β, as determined by $^3$H-thymidine uptake using culture cells from a mink lung epithelial cell line (ATCC No. CCL 64, Rockville, Md.). Briefly cells are grown to confluency with in EMEM, supplemented with 10% FBS, 200 units/ml penicillin, and 200 μg/ml streptomycin. These cells are cultured to a cell density of about 200,000 cells per well. At confluency the media is replaced with 0.5 ml of EMEM containing 1%FBS and penicillin/streptomycin and the culture incubated for 24 hours at 37° C. Candidate proteins then are added to each well and the cells incubated for 18 hours at 37° C. After incubation., 1.0 μCi of $^3$H-thymidine in 10 μl was added to each well, and the cells incubated for four hours at 37° C. The media then is removed from each well and the cells washed once with ice-cold phosphate buffered saline and DNA precipitated by adding 0.5 ml of 10% TCA to each well and incubated at room temperature for 15 minutes. The cells are washed three times with ice-cold distilled water, lysed with 0.5 ml 0.4 M NaOH, and the lysate from each well then transferred to a scintillation vial and the radioactivity recorded using a scintillation counter (Smith-Kline Beckman). Biologically active molecules will inhibit cell proliferation resulting in less thymidine uptake and fewer counts as compared to inactive proteins and/or the negative control well (no added growth factor).

Example 8

Testing the Altered Attributes of a Mutant Protein of the Present Invention: In vivo Bioassay of Osteogenic Activity (Endochondral Bone Formation and Related Properties)

The art-recognized bioassay for bone induction as described by Sampath and Reddi (*Proc. Natl. Acad. Sci. USA* (1983) 80:6591–6595) and U.S. Pat. Nos. 4,968,590, 5,266,683, the disclosures of which is herein incorporated by reference, can be used to establish the efficacy of a given device or formulation. Briefly, the assay consists of depositing test samples in subcutaneous sites in recipient rats under ether anesthesia. A vertical incision (1 cm) is made under sterile conditions in the skin over the thoracic region, and a pocket is prepared by blunt dissection. In certain, to the desired amount of osteogenic protein (10 ng–10 μg) approximately 25 mg of matrix material, using standard procedures such as lyophilization, is added and implanted deep into the pocket and the incision is closed with a metallic skin clip. The heterotropic site allows for the study of bone induction without the possible ambiguities resulting from the use of orthotopic sites. The implants also can be provided intramuscularly which places the devices in closer contact with accessable progenitor cells. Typically intramuscular implants are made in the skeletal muscle of both legs.

The sequential cellular reactions occurring at the heterotropic site are complex. The multistep cascade of endochondral bone formation includes: binding of fibrin and fibronectin to implanted matrix, chemotaxis of cells, proliferation of fibroblasts, differentiation into chondroblasts, cartilage formation, vascular invasion, bone formation, remodeling, and bone marrow differentiation.

Successful implants exhibit a controlled progression through the stages of protein induced endochondral bone development including: (1) transient infiltration by polymorphonuclear leukocytes on day one; (2) mesenchymal cell migration and proliferation on days two and three; (3) chondrocyte appearance on days five and six; (4) cartilage matrix formation on day seven; (5) cartilage calcification on day eight; (6) vascular invasion, appearance of osteoblasts, and formation of new bone on days nine and ten; (7) appearance of osteoblastic and bone remodeling on days twelve to eighteen; and (8) hematopoietic bone marrow differentiation in the ossicle on day twenty-one.

Histological sectioning and staining is preferred to determine the extent of osteogenesis in the implants. Staining with toluidine blue or hemotoxylin/cosin clearly demonstrates the ultimate development of endochondral bone. Twelve day bioassays are sufficient to determine whether bone inducing activity is associated with the test sample.

Additionally, alkaline phosphatase activity and/or total calcium content can be used as biochemical markers for osteogenesis. The alkaline phosphatase enzyme activity can be determined spectrophotometrically after homogenization of the excised test material. The activity peaks at 9–10 days in vivo and thereafter slowly declines. Samples showing no bone development by histology should have no alkaline phosphatase activity under these assay conditions. The assay is useful for quantitation and obtaining an estimate of bone formation very quickly after the test samples are removed from the rat. The results as measured by alkaline phosphatase activity level and histological evaluation can be represented as "bone forming units". One bone forming unit represents the amount of protein that is needed for half maximal bone forming activity on day 12. Additionally, dose curves can be constructed for bone inducing activity in vivo at each step of a purification scheme by assaying various concentrations of protein. Accordingly, the skilled artisan can construct representative dose curves using only routine experimentation.

Total calcium content can be determined after homogenization in, for example, cold 0.15M NaCl, 3 mM $NaHCO_3$, pH 9.0, and measuring the calcium content of the acid soluble fraction of sediment.

Example 9

Exemplary Modified Morphogen Mutants Having Altered Attributes: Domain Swapping

FIG. 4 is a schematic drawing of various biosynthetic mutants and their refolding and biological attributes. The thick solid line represents OP-1, a thin solid line represents CDMP-2/GDF-6 or GDF-5, and a hatched line represents BMP-2. Mutant constructs are presented in FIG. 4A and individual sequence mutants are presented in FIG. 4B. Individual residue changes are indicated by the substituting residue in the figure. The residue numbering is as described above, counting from the first residue after the cysteine doublet in finger 2. For example, mutant H2233 is OP-1 (25R>E 26N>D 30R>E 35H>R). Similarly, mutant H2447 has all the changes in H2233 and, in addition, has 1A>V 4Q>E 6N>S. Mutant H2433 is OP-1(4Q>K 35H>R), and mutant H2456 is OP-1(4Q>E 6N>S 25R>E 26N>D 30R>E 35H>R).

As taught herein, the present invention provides the skilled artisan with the know-how to craft customized mutant proteins and DNAs encoding the same. Further taught and exemplified herein are the means to design mutant proteins having certain desired allribute(s) making them suitable for specific in vivo applications (see at least Sections I.B.,II., and III. Examples 1–4, 8 and 11 for exemplary embodiments of the foregoing mutant proteins). For example, mutant proteins having altered solubility attributes can be used in vivo to manipulate morphogenic effective amounts provided to a recipient. That is, increased solubility can result in increased availability; diminished solubility can result in decreased availability. Thus, such systemically administered mutant proteins can be immediately available/have immediate morphogenic effects, whereas locally administered mutant proteins can be available more slowly/have prolonged morphogenic effects. The skilled artisan will appreciate when increased versus diminished solubility attributes are preferred given the facts and circumstances at hand. Optimization of such parameters requires routine experimentation and ordinary skill.

Similarly, mutant proteins having altered stability attributes can be used in vivo to manipulate morphogenic effective amounts provided to a recipient. That is, increased stability can result in increased half-life because turnover in vivo is less; diminished stability can result in decreased half-life and availability because turnover in vivo is more. Thus, such systemically administered mutant proteins can either be immediately available/have immediate morphogenic effects achieving a bolus-type dosage or can be available in vivo for prolonged periods/have prolonged morphogenic effects achieving a sustained release type dosage. The skilled artisan will appreciate when increased versus diminished stability attributes are preferred given the facts and circumstances at hand. Optimization of such parameters requires routine experimentation and ordinary skill.

Additionally, mutant proteins having a combination of altered attributes, such as but not limited to solubility and stability attributes, can be used in vivo to manipulate morphogenic effective amounts provided to a recipient. That is, by designing a mutant protein with a combination of specific altered attributes, morphogenic effective amounts can be administered in a timed-release fashion; dosages can be regulated both in terms of amount and duration; treatment regimens can be initiated at low doses systemically or locally followed by a transition to high doses, or vice versa; to name but a few paradigms. The skilled artisan will appreciate when low versus high morphogenic effective amounts are suitable under the facts and circumstances at hand. Optimization of such parameters requires routine experimentation and ordinary skill.

Furthermore, mutant proteins having one or more altered attributes are useful to overcome inherent deficiencies in development. Mutant proteins having one or more altered attributes can be designed to circumvent an inherent defect in a host's native morphogenic signaling system. As a non-limiting example, a mutant protein of the present invention can be used to bypass a defect in a native receptor in a target tissue, a defect in an intracellular signaling pathway, and/or a defect in other events which are reliant on the attributes of a sub-domain(s) associated with recognition of a moiety per se as opposed to the attributes associated with function/biological activity which are embodied in a different sub-domain(s). The skilled artisan will appreciate when such mutant proteins are suitable given the facts and circumstances at hand. Optimization requires routine experimentation and ordinary skill.

Example 10

Determination of Binding Activity of an OP-1 Based Mutant Construct

Cells expressing an OP-1 receptor on their cell surface are plated into 35 mm dishes and incubated for 48 hours in DMEM (Dulbecco's modified Eagle medium) plus 10% fetal calf serum. Purified OP-1, or an OP-1-analog is iodinated with $Na^{125}I$ by chloramine T oxidation, preferably having a specific activity of about 50–100 mCi/mg, by following essentially the protocol of Frolik et al. (1984) *J. Biol. Chem.* 595: 10995–11000. Labeled OP-1, or OP-1-analog, then is purified using a standard procedure, e.g., by chromatographic separation. The plated cells then are washed twice with physiologically buffered saline in the presence of 0.1% BSA, and incubated at 22° C. in the presence of BSA, buffer and labeled OP-1 (1 ng) and various concentrations (e.g., 0–10 mg/ml) of unlabelled competitor, e.g., unlabelled OP-1 or the OP-1 based mutant. Following binding, the cells are washed three times with cold buffer, solubilized in 0.5 ml of 0.5 N NaOH, removed from the dish, and radioactivity determined by gamma or scintillation counter. Data then are expressed as percent inhibition, where 100% inhibition of specific binding is the difference between binding in the absence of competitor and binding in the presence of a 100-fold molar excess of unlabelled competitor. Binding parameters preferably are determined using a computer program such as LIGAND (Munsun et al. (1980) *Anal. Biochem.* 107: 220–259). Upon performance of the assay, it is contemplated that the OP-1 based mutant may have specific binding activity for the OP-1 receptor. Upon confirmation of binding activity, the mutant can be tested subsequently for other indicia of biological activity.

Example 11

Other indicia of Biological Activities of an OP-1 Based Mutant Construct

The biological activity of the resulting OP-1 based mutant construct can be determined using any of the using standard in vivo and in vitro assays, typically used for assessing native OP-1 activity. A variety of additional exemplary assays are set forth in detail below.

A. Progenitor Cell Stimulation.

The following example is designed to demonstrate the ability of OP-1 based mutants to stimulate the proliferation of mesenchymal progenitor cells. Useful naive stem cells include pluripotential stem cells, which may be isolated from bone marrow or umbilical cord blood using conventional methodologies, (see, for example, Faradji et al. (1988) *Vox Sang.* 55 (3): 133–138 or Broxmeyer at al. (1989) *Proc. Natl. Acad. Sci. USA*. 86: 3828–3832), as well as naive stem cells obtained from blood. Alternatively, embryonic cells (e.g., from a cultured mesodermal cell line) may be used.

Another method for obtaining progenitor cells and for determining the ability of OP-1 based mutants to stimulate cell proliferation is to capture progenitor cells from an in vivo source. For example, a biocompatible matrix material able to allow the influx of migratory progenitor cells may be implanted at an in vivo site long enough to allow the influx of migratory progenitor cells. For example, a bone-derived, guanidine-extracted matrix, formulated as disclosed for example in Sampath et al. (1983) *Proc. Natl. Acad. Sci. USA* 80: 6591–6595, or U.S. Pat. No. 4,975,526, may be implanted into a rat at a subcutaneous site, essentially following the method of Sampath et al. After three days the implant is removed, and the progenitor cells associated with the matrix dispersed and cultured.

Progenitor cells, however obtained, then are incubated in vitro with the OP-1 based mutant under standard cell culture conditions, such as those described hereinbelow. In the absence of external stimuli, the progenitor cells do not, or only minimally, proliferate on their own in culture. It is contemplated, however, that progenitor cells cultured in the presence of a biologically active OP-1 mutant, like OP-1, will proliferate. Cell growth can be determined visually or spectrophotometrically using standard methods well known in the art.

B. Morphogen-Induced Cell Differentiation.

A variety of assays maybe used to determine OP-1 based cellular differentiation.

1. Embryonic Mesenchyme Differentiation

As with natural OP-1, it is contemplated that OP-1 based mutants can be utilized to induce cell differentiation. The ability to induce cell differentiation can be demonstrated by culturing early mesenchymal cells in the presence of the mutant protein and then studying the histology of the cultured cells by staining with toluidine blue using standard cell culturing and cell staining methodologies well described in the art. For example, it is known that rat mesenchymal cells destined to become mandibular bone, when separated from the overlying epithelial cells at stage 11 and cultured in vitro under standard tissue culture conditions, e.g., in a chemically defined, serum-free medium, containing for example, 67% DMEM (Dulbecco's modified Eagle's medium), 22% F-12 medium, 10 mM Hepes pH 7, 2 mM glutamine, 50 mg/ml transferring, 25 mg/ml insulin, trace elements, 2 mg/ml bovine serum albumin coupled to oleic acid, with HAT (0.1 mM hypoxanthine, 10 mM aminopterin, 12 mM thymidine), will not continue to differentiate. However, if these same cells are left in contact with the overlying endoderm for an additional day, at which time they become stage 12 cells, they will continue to differentiate on their own in vitro to form chondrocytes. Further differentiation into osteoblasts and, ultimately, mandibular bone, requires an appropriate local environment, e.g., a vascularized environment.

It is anticipated that, as with natural OP-1, stage 11 mesenchymal cells, cultured in vitro in the presence of an OP-1 mutant, e.g., 10–100 ng/ml, will continue to differentiate in vitro to form chondrocytes just as they continue to differentiate in vitro if they are cultured with the cell products harvested from the overlying endodermal cells. This experiment may be performed with different mesenchymal cells to demonstrate cell differentiation capability.

2. Alkaline Phosphatase Induction of Osteoblasts.

As another example of morphogen-induced cell differentiation, the ability of OP-1 mutants to induce osteoblast differentiation may be demonstrated in vitro using primary osteoblast cultures, or osteoblast-like cell lines, and assaying for a variety of bone cell markers that are specific markers for the differentiated osteoblast phenotype, e.g., alkaline phosphatase activity, parathyroid hormone-mediated cyclic AMP (cAMP) production, osteocalcin synthesis, and enhanced mineralization rates.

Cultured osteoblasts in serum-free medium are incubated with, a range of OP-1 mutant concentrations, for example, 0.1, 1.0, 10.0, 40.0 or 80.0 ng OP-1 mutant/ml medium; or with a similar concentration range of natural OP-1 or TGF-β. After a 72 hour incubation the cell layer is extracted with 0.5 ml of 1% Triton X-100. The resultant cell extract, is centrifuged, and 100 μl of the extract is added to 90 μl of paranitroso-phenylphosphate (PNPP)/glycerine mixture and incubated for 30 minutes in a 37° C. water bath and the reaction stopped with 100 μl 0.2N NaOH. The samples then are run trough a plate reader (e.g., Dynatech MR700 plate reader, and absorbance measured at 400 nm, using p-nitrophenol as a standard) to determine the presence and amount of alkaline phosphate activity. Protein concentrations are determined by the BioRad method. Alkaline phosphatase activity is calculated in units/μg protein, where 1 unit=1 nmol p-nitrophenol liberated/30 minutes at 37° C.

The OP-1 mutant, like natural OP-1 alone, stimulates the production of alkaline phosphatase in osteoblasts thereby promoting the growth and expression of the osteoblast differentiated phenotype.

The long term effect of OP-1 mutant on the production of alkaline phosphatase by rat osteoblasts also can be demonstrated as follows.

Rat osteoblasts are prepared and cultured in multi-well plates as described above. In this example six sets of 24 well plates are plated with 50,000 rat osteoblasts per well. The wells in each plate, prepared as described above, then are divided into three groups: (1) those which receive, for example, 1 ng of OP-1 mutant per ml of medium; (2) those which receive 40 ng of OP-1 mutant per ml of medium; and (3) those which received 80 ng of OP-1 mutant per ml of medium. Each plate then is incubated for different lengths of time: 0 hours (control time), 24 hours, 48 hours, 96 hours, 120 hours and 144 hours. After each incubation period, the cell layer is extracted with 0.5 ml of 1% Triton X-100. The resultant cell extract is centrifuged, and alkaline phosphatase activity determined using paranitroso-phenylphosphate (PNPP), as above. The OP-1 mutant, like natural OP-1, will stimulate the production of alkaline phosphatase in osteoblasts in dose-dependent manner so that increasing doses of OP-1 mutant will further increase the level of alkaline phosphatase production. Moreover, it is contemplated that the OP-1 mutant-stimulated elevated levels of alkaline phosphatase in the treated osteoblasts will last for an extended period of time.

3. Induction of PTH-Mediated cAMP.

This experiment is designed to test the effect of OP-1 mutant on parathyroid hormone mediated CAMP production in rat osteoblasts in vitro. Briefly, rat osteoblasts are prepared and cultured in a multiwell plate as described above. The cultured cells then are divided into four groups: (1) wells which receive, for example, 1.0, 10.0 and 40.0 ng OP-1 mutant/ml medium); (2) wells which receive for example, natural OP-1, at similar concentration ranges; (3) wells which receive for example, TGF-β, at similar concentration ranges; and (4) a control group which receives no growth factors. The plate then is incubated for another 72 hours. At the end of the 72 hours the cells are treated with medium containing 0.5% bovine serum albumin (BSA) and 1 mM 3-isobutyl-1-methylxanthine for 20 minutes followed by the addition into half of the wells of human recombinant parathyroid hormone (hPTH, Sigma, St. Louis) at a concentration of 200 ng/ml for 10 minutes. The cell layer then is extracted from each well with 0.5 ml of 1 Triton X-100. The cAMP levels then are determined using a radioimmunoassay kit (e.g., Amersham, Arlington Heights, Ill.). The OP-1 mutant alone, like OP-1, will stimulate an increase in the PTH-mediated cAMP response, thereby promoting the growth and expression of the osteoblast differentiated phenotype.

4. Induction of Osteocalcin Production.

Osteocalcin is a bone-specific protein synthesized by osteoblasts which plays an integral role in the rate of bone mineralization in vivo. Circulating levels of osteocalcin in serum are used as a marker for osteoblast activity and bone formation in vivo. Induction of osteocalcin synthesis in osteoblast-enriched cultures can be used to demonstrate OP-1 mutant efficacy in vitro.

Rat osteoblasts are prepared and cultured in a multi-well plate as above. In this experiment the medium is supplemented with 10%FBS, and on day 2, cells are fed with fresh medium supplemented with fresh 10 mM β-glycerophosphate (Sigma, Inc.). Beginning on day 5 and twice weekly thereafter, cells are fed with a complete mineralization medium containing all of the above components plus fresh L(+)-ascorbate, at a final concentration of 50 mg/ml medium. OP-1 mutant then is added to the wells directly, e.g., in 50% acetonitrile (or 50% ethanol) containing 0.1% trifluoroacetic acid (TFA), at no more than 5 ml mutant/ml medium. Control wells receive solvent vehicle only. The cells then are re-fed and the conditioned medium sample diluted 1:1 in standard radioimmunoassay buffer containing standard protease inhibitors and stored at –20° C. until assayed for osteocalcin. Osteocalcin synthesis is measured by standard radioimmunoassay using a commercially available osteocalcin-specific antibody.

Mineralization is determined on long term cultures (13 day) using a modified von Kossa staining technique on fixed cell layers: cells are fixed in fresh 4% paraformaldehyde at 23° C. for 10 min, following rinsing cold 0.9% NaCl. Fixed cells then are stained far endogenous alkaline phosphatase at pH 9.5 for 10 min, using a commercially available kit (Sigma, Inc.). Purple stained cells then are dehydrated with methanol and air dried. After 30 min incubation in 3% $AgNO_3$ in the dark, $H_2O$-rinsed samples are exposed for 30 sec to 254 nm UV light to develop the black silver-stained phosphate nodules. Individual mineralized foci (at least 20 mm in size) are counted under a dissecting microscope and expressed as nodules/culture, The OP-1 mutant, like natural OP-1, will stimulate osteocalcin synthesis in osteoblast cultures. Furthermore, increased osteocalcin synthesis in response to OP-1 mutant will be in a dose dependent manner thereby showing a significant increase over the basal level after 13 days of incubation. The enhanced osteocalcin synthesis also may be confirmed by detecting the elevated osteocalcin mRNA message (20-fold increase) using a rat osteocalcin-specific probe. In addition, the increase in osteoclacin synthesis correlates with increased mineralization in long term osteoblast cultures as determined by the appearance of mineral nodules. It is contemplated also that OP-1 mutant, like natural OP-1, will increase significantly the initial mineralization rate as compared to untreated cultures.

5. Morphogen-Induced CAM Expression.

Native members of the vg/dpp subgroup induce CAM expression, particularly N-CAM expression, as part of their induction of morphogenesis (see copending U.S. Ser. No. 922,813). CAMs are morphoregulatory molecules identified in all tissues as an essential step in tissue development. N-CAMs, which comprise at least 3 isoforms (N-CAM-180, N-CAM-140 and N-CAM-120, where "180", "140" and "120" indicate the apparent molecular weights of the isoforms as measured by SDS polyacrylamide gel electrophoresis) are expressed at least transiently in developing tissues, and permanently in nerve tissue. Both the N-CAM-180 and N-CAM-140 isoforms are expressed in both developing and adult tissue. The N-CAM-120 isoform is found only in adult tissue. Another neural CAM is L1.

The ability of OP-1 based mutant to stimulate CAM expression can be demonstrated using the following protocol, using NG108-15 cells. NG108-15 is a transformed hybrid cell line (neuroblastoma×glioma, America Type Culture Collection (ATCC), Rockville, Md.), exhibiting a morphology characteristic of transformed embryonic neurons. As described in Example D, below, untreated NG108-15 cells exhibit a fibroblastic, or minimally differentiated, morphology and express only the 180 and 140 isoforms of N-CAM normally associated with a developing cell. Following treatment with members of the vg/dpp subgroup these cells exhibit a morphology characteristic of adult neurons and express enhanced levels of all three N-CAM isoforms.

In this example, NG108-15 cells are cultured for 4 days in the presence of increasing concentrations of either the OP-1 morphon or natural OP-1 using standard culturing procedures, and standard Western blots performed on whole cell extracts. N-CAM isoforms are detected with an antibody which crossreacts with all three isoforms, mAb H28.123, obtained from Sigma Chemical Co., St. Louis, the different isoforms being distinguishable by their different mobilities on an electrophoresis gel. Control NG108-15 cells (untreated) express both the 140 kDa and the 180 kDa isoforms, but not the 120 kDa, as determined by Western blot analyses using up to 100 mg of protein. Treatment of NG108-15 cells with OP-1 mutant, like natural OP-1 results in a dose-dependent increase in the expression of the 180 kDa and 140 kDa isoforms, as well as the induction of the 120 kDa isoform induced. In addition, it is contemplated that the OP-1 mutant, like natural OP-1-induced CAM expression may correlate with cell aggregation, as determined by histology.

C. Redifferentiation of Transformed Phenotype.

The OP-1 mutant, like natural OP-1, also induces redifferentiation of transformed cells to a morphology characteristic of untransformed cells. The examples provided below detail morphogen-induced redifferentiation of a transformed human cell line of neuronal origin (NG108-15); as well as mouse neuroblastoma cells (N1E-115), and human embryo carcinoma cells, to a morphology characteristic of untransformed cells.

As described above, NG108-15 is a transformed hybrid cell line produced by fusing neuroblastoma×glioma cells (obtained from ATCC. Rockville, Md.), and exhibiting a morphology characteristic of transformed embryonic neurons, e.g., having a fibroblastic morphology. Specifically, the cells have polygonal cell bodies, short, spike-like processes and make few contacts with neighboring cells. Incubation of NG108-15 cells, cultured in a chemically defined, serum-free medium, with 0.1 to 300 ng/ml of OP-1 mutant or natural OP-1 for four hours induces an orderly, dose-dependent change in cell morphology.

For example, NG108-15 cells are subcultured on poly-L-lysine coated 6 well plates. Each well contains 40–50,000 cells in 2.5 ml of chemically defined medium. On the third day, 2.5 ml of OP-1 mutant or natural OP-1 in 60% ethanol containing 0.025% trifluoroacetic is added to each well, The media is changed daily with new aliquots of morphogen. It is contemplated that OP-1 mutant like OP-1 induces a dose-dependent redifferentiation of the transformed cells, including a rounding of the soma, an increase in phase brightness, extension of the short neurite processes, and other significant changes in the cellular ultrastructure. After several days it is contemplated also that treated cells begin to form epithelioid sheets that then become highly packed, multi-layered aggregates, as determined visually by microscopic examination.

Moreover, it is contemplated that the redifferentiation occur without any associated changes in DNA synthesis, cell division, or cell viability, making it unlikely that the morphologic changes are secondary to cell differentiation or a toxic effect of the morphogen. In addition, it is contemplated that the morphon-induced redifferentiation may not inhibit cell division, as determined by $^3$H-thymidine uptake, unlike other molecules such as butyrate, DMSO, retinoic acid or Forskolin which have been shown to stimulate differentiation of transformed cells, in analogous experiments. The OP-1 mutant, like natural OP-1, maintains cell stability and viability after inducing redifferentiation.

The modified morphogen described herein would, therefore, provide useful therapeutic agents for the treatment of neoplasias and neoplasiac lesions of the nervous system, particularly in the treatment of neuroblastoma, including retinoblastomas, and gliomas.

D. Maintenance of Phenotype.

OP-1 mutant, like natural OP-1, also can be used to maintain a cell's differentiated phenotype. This application is particularly useful for inducing the continued expression of phenotype in senescent or quiescent cells.

1. In Vitro Model for Phenotypic Maintenance.

The phenotypic maintenance capability of morphogens is determined readily. A number of differentiated cells become senescent or quiescent after multiple passages in vitro under standard tissue culture conditions well described in the art (e.g., *Culture of Animal Cells: A Manual of Basic Techniques*, C. R. Frestmey, ed., Wiley, 1987). However, if these cells are cultivated in vitro in association with a native morphogen such as OP-1, cells are stimulated to maintain expression of their phenotype through multiple passages. For example, the alkaline phosphatase activity of cultured osteoblasts, such as cultured osteosarcoma cells and calvaria cells, is significantly reduced after multiple passages in vitro. However, if the cells are cultivated in the presence of OP-1 alkaline phosphatase activity is maintained over extended periods of time. Similarly, phenotypic expression of myocytes also is maintained in the presence of a morphogen. In the experiment, osteoblasts are cultured as described above. The cells are divided into groups, incubated with varying concentrations of either OP-1 mutant or natural OP-1 (e.g., 0–300 ng/ml) and passaged multiple times (e.g., 3–5 times) using standard methodology. Passaged cells then are tested for alkaline phosphatase activity, as described herein as an indication of differentiated cell metabolic function. It is contemplated that osteoblasts cultured in the absence of OP-1 mutant, like natural OP-1, have reduced alkaline phosphatase activity, as compared to OP-1 mutant, or natural OP-1-treated cells.

2. In Vivo Model for Phenotypic Maintenance.

Phenotypic maintenance capability also may be demonstrated in vivo, using a standard rat model for osteoporosis. Long Evans female rats (Charles River Laboratories, Wilmington, Mass.) are Sham-operated (control animals) or ovariectomized using standard surgical techniques, to produce an osteoporosic condition resulting from decreased estrogen production. Following surgery, e.g., 200 days after ovariectomy, rats are systemically provided with phosphate buffered saline (PBS) or morphogen, (e.g., OP-1 mutant, or natural OP-1, 1–10 mg) for 21 days (e.g., by daily tail vein injection.) The rats then are sacrificed and serum alkaline phosphatase levels, serum calcium levels, and serum osteocalcin levels are determined, using standard methodologies as described therein and above. It is contemplated that the OP-1 mutant treated rats, like the OP-1 treated rats may exhibit elevated levels of osteocalcin and alkaline phosphatase activity. Histomorphometric analysis on the tibial diasypheal bone shows improved bone mass in OP-1 mutant treated animals as compared with untreated, ovariectomized rats.

E. Proliferation of Progenitor Cell Populations.

Progenitor cells can be stimulated to proliferate in vivo or ex vivo. It is contemplated that cells can be stimulated in vivo by injecting or otherwise providing a sterile preparation containing the OP-1 mutant into the individual. For example, the hemopoietic pluripotential stem cell population of an individual can be stimulated to proliferate by injecting or otherwise providing an appropriate concentration of OP-1 mutant to the individual's bone marrow.

Progenitor cells can be stimulated ex vivo by contacting progenitor cells of the population to be enhanced with a morphogenically active OP-1 mutant under sterile conditions at a concentration and for a time sufficient to stimulate proliferation of the cells. Suitable concentrations and stimulation times may be determined empirically, essentially following the procedure described in Example A, above. OP-1 mutant concentration of between about 0.1–100 ng/ml and a stimulation period of from about 10 minutes to about 72 hours, or, more generally, about 24 hours, typically should be sufficient to stimulate a cell population of about $10^4$ to $10^6$ cells. The stimulated cells then may be provided to the individual as, for example, by injecting the cells to an appropriate in vivo locus. Suitable biocompatible progenitor cells may be obtained by any of the methods known in the art or described hereinabove.

F. Regeneration of Damaged or Diseased Tissue.

OP-1 mutants can be used to repair diseased or damaged mammalian tissue. The tissue to be repaired preferably is assessed first, and excess necrotic or interfering scar tissue removed as needed, e.g., by ablation or by surgical, chemical, or other methods known in the medical arts.

OP-1 mutant can then be provided directly to the tissue locus as part of a sterile, biocompatible composition, either by surgical implantation or injection. The mutant also can be provided systemically, as by oral or parenteral administration. Alternatively, a sterile, biocompatible composition containing progenitor cells stimulated by a morphogenically active OP-1 mutant can be provided to the tissue locus. The existing tissue at the locus, whether diseased or damaged, provides the appropriate matrix to allow the proliferation and tissue) specific differentiation of progenitor cells. In addition, a damaged or diseased tissue locus, particularly one that has been further assaulted by surgical means, provides a morphogenically permissive environment. Systemic provision of OP-1 mutant may be sufficient for certain applications (e.g., in the treatment of osteoporosis and other disorders of the bone remodeling cycle, as an example).

In some circumstances, particularly where tissue damage is extensive, the tissue may not be capable of providing a sufficient matrix for cell influx and proliferation. In these instances, it may be necessary to provide progenitor cells stimulated by the OP-1 mutant to the tissue locus in association with a suitable, biocompatible, formulated matrix, prepared by any of the means described below. The matrix preferably is in vivo biodegradable. The matrix also may be tissue-specific and/or may comprise porous particles having dimensions within the range of 70–850 mm, most preferably 150–420 mm.

OP-1 mutant also may be used to prevent or substantially inhibit immune/inflammatory response-mediated tissue damage and scar tissue formation following an injury. OP-1 mutant may be provided to a newly injured tissue locus, to induce tissue morphogenesis at the locus, preventing the aggregation of migrating fibroblasts into non-differentiated connective tissue. Preferably the OP-1 mutant may be provided as a sterile pharmaceutical preparation injected into the tissue locus within five hours of the injury. Where an immune/inflammatory response is unavoidably or deliberately induced, as part of, for example, a surgical or other aggressive clinical therapy, OP-1 mutant preferably may be provided prophylactically to the patient, prior to, or concomitant with, the therapy.

G. Morphogenesis Assays.

Below are several examples, describing protocols for demonstrating that the mutant proteins disclosed herein can be used to induce tissue morphogenesis. By way of example, the following is a description of OP-1 mutant-induced tissue morphogenesis in bone, liver, nerve, dentin, cementum and periodontal tissue.

1. OP-1 Mutant-Induced Bone Morphogenesis.

As described earlier, particularly useful mammalian tissue model system for demonstrating and evaluating the morphogenic activity of a protein is the endochondral bone tissue morphogenesis model known in the an and described, for example, in U.S. Pat. No. 4,968,590 and incorporated herein by reference. The ability to induce endochondral bone formation includes the ability to induce proliferation and differentiation of progenitor cells into chondroblasts and osteoblasts, the ability to induce cartilage matrix formation, cartilage calcification, and bone remodeling, and the ability to induce formation of an appropriate vascular supply and hematopoeitic bone marrow differentiation.

The local environment, in which the morphogenic material is placed, is important for tissue morphogenesis. As used herein, "local environment" is understood to include the tissue structural matrix and the environment surrounding the tissue. For example, in addition to needing an appropriate anchoring substratum for their proliferation, the cells stimulated by morphogens need signals to direct the tissue-specificity of their differentiation. These signals vary for the different tissues and may include cell surface markers. In addition, vascularization of new tissue requires a local environment which supports vascularization.

The following sets forth various procedures for evaluating the in vivo morphogenic utility of OP-1 mutant and OP-1 mutant containing compositions. The compositions may be injected or surgically implanted in a mammal, following any of a number of procedures well known in the art. For example, surgical implant bioassays may be performed essentially following the procedure of Sampath et al, (1983) *Proc. Natl. Acad. Sci. USA* 80: 6591–6595 and U.S. Pat No. 4,968,590.

Histological sectioning and staining is preferred to determine the extent of morphogenesis in vivo, particularly in tissue repair procedures. Excised implants are fixed in Bouins Solution, embedded in paraffin, and cut into 6–8 mm sections. Staining with toluidine blue or hemotoxylinleosin demonstrates clearly the ultimate development of the new tissue. Twelve day implants are usually sufficient to determine whether the implants contain newly induced tissue.

Successful implants exhibit a controlled progression through the stages of induced tissue development allowing one to identify and follow the tissue-specific events that occur. For example, in endochondral bone formation the stages include: (1) leukocytes on day one; (2) mesenchymal cell migration and proliferation on days two and three; (3) chondrocyte appearance on days five and six; (4) cartilage matrix formation on day seven; (5) cartilage calcification on day eight; (6) vascular invasion, appearance of osteoblasts, and formation of new bone on days nine and ten; (7) appearance of osteoclastic cells, and the commencement of bone remodeling and dissolution of the implanted matrix on days twelve to eighteen; and (8) hematopoietic bone marrow differentiation in the resulting ossicles on day twenty-one.

In addition to histological evaluation, biological markers may be used as markers for tissue morphogenesis. Useful markers include tissue-specific enzymes whose activities may be assayed (e.g., spectrophotometrically) after homogenization of the implant. These assays may be useful for quantitation and for rapidly obtaining an estimate of tissue formation after the implants are removed from the animal. For example, alkaline phosphatase activity may be used as a marker for osteogenesis.

Incorporation of systemically provided OP-1 mutant can be followed using labeled protein (e.g., radioactively labelled) and determining its localization in the new tissue, and/or by monitoring their disappearance from the circulatory system using a standard labeling protocol and pulse-chase procedure. OP-1 mutant also may be provided with a tissue-specific molecular tag, whose uptake may be monitored and correlated with the concentration of OP-1 mutant provided. As an example, ovary removal in female rats results in reduced bone alkaline phosphatase activity, and renders the rats predisposed to osteoporosis. If the female rats now are provided with OP-1 mutant, a reduction in the systemic concentration of calcium may be seen, which correlates with the presence of the provided OP-1 mutant and which is anticipated to correspond with increased alkaline phosphatase activity.

2. OP-1 Mutant-Induced Liver Regeneration.

As another example, a method for inducing morphogenesis of substantially injured liver tissue following a partial hepatectomy utilizing OP-1 mutant is presented. Variations on this general protocol may be used to test morphogen activity of OP-1 mutant in other different tissues. The general method involves excising an essentially nonregenerating portion of a tissue and providing OP-1 mutant, preferably as a soluble pharmaceutical preparation to the excised tissue locus, closing the wound, and examining the site at a future date. Like bone, liver has a potential to regenerate upon injury during post-fetal life.

OP-1 mutant, e.g., 1 mg/ml, in a biocompatible solution, for example, a purified OP-1 mutant, is solubilized in 50% ethanol, or compatible solvent, containing 0.1% trifluoroacetic acid, or compatible acid. The injectable OP-1 mutant solution is prepared, e.g., by diluting one volume of OP-1 morphon solvent-acid stock solution with 9 volumes of 0.2% rat serum albumin in sterile PBS (phosphate-buffered saline).

In the experiment, growing rats or aged rats (e.g., Long Evans, Charles River Laboratories, Wilmington, Mass.) are anesthetized by using ketamine. Two of the liver lobes (left and right) are cut out (approximately ⅓ of the lobe) and the OP-1 mutant is injected locally at multiple sites along the cut ends. The amount of OP-1 mutant injected may be, e.g., 20–100 μg in 100–1000 μl PBS/RSA (phosphate buffered saline rat serum albumin) injection buffer. Placebo samples comprise injection buffer only. In experimental essays, five rats in each group preferably are used. The wound is closed and the rats are allowed to eat normal food and drink tap water.

After 12 days, the rats are sacrificed and liver regeneration is observed visually, to evaluate the effects of the OP-1 mutant on liver regeneration most effectively. It is contemplated that the OP-1 mutant injected group will show complete liver tissue regeneration with no sign remaining of any cut in the liver. By contrast, the control group into which only PBS is injected, show typically only minimal regeneration with the incision remaining in the sample.

3. OP-1 Mutant-Induced Dentin, Cementum and Periodontal Ligament Regeneration.

As still another example, the ability of OP-1 mutant to induce dentinogenesis also can be demonstrated. To date, the unpredictable response of dental pulp tissue to injury is a basic clinical problem in dentistry. Cynomolgus monkeys are chosen as primate models as monkeys are presumed to be more indicative of human dental biology than models based on lower non primate mammals.

Using standard dental surgical procedures, small areas (e.g., 2 mm) of dental pulps are surgically exposed by removing the enamel and dentin immediately above the pulp (by drilling) of sample teeth, performing a partial amputation of the corona pulp tissue, inducing homeostasis, application of the pulp treatment, and sealing and filling the cavity by standard procedures.

Pulp treatments used include: an OP-1 mutant dispersed in a carrier matrix; carrier matrix alone, and no treatment. Twelve teeth per animal (four far each treatment) are prepared, and two animals are used. At four weeks, teeth are extracted and processed histologically for analysis of dentin formation, and/or ground to analyze dentin mineralization. The effect of OP-1 mutant on osteodentin reparation may be observed visually by comparing with the control samples. It is contemplated that the OP-1 mutant, like natural OP-1, plus a carrier matrix induce formation of reparative, osteodentin bridges, traversing on surgically exposed healthy dental pulps. By contrast, pulps treated with tamer matrix alone, do not form reparative dentin.

4. OP-1 Mutant-Induced Nerve Tissue Repair.

As yet another example, the induction of regenerative effects on central nervous system (CNS) repair, by a morphogenically active OP-1 mutant, can be demonstrated using a rat brain stab model. Briefly, male Lang Evans rats are anesthetized and the head area prepared for surgery. The calvariae is exposed using standard surgical procedures and a hole drilled toward the center of each lobe using a 0.035K wire, just piercing the calvariae. 25 ml solutions containing either OP-1 mutant (25 mg), natural OP-1 (25 mg) or PBS then is provided to each of the holes by Hamilton syringe. Solutions are delivered to a depth approximately 3 mm below the surface, into the underlying cortex, corpus callosum and hippocampus. The skin then is sutured and the animal allowed to recover.

Three days post surgery, rats are sacrificed by decapitation and their brains processed for sectioning. Scar tissue formation is evaluated by immunofluoresence staining for glial fibrillary acidic protein, a marker protein for glial scarring, to qualitatively determine the degree of scar formation. It is contemplated that the OP-1 mutant, like natural OP-1, may result in reduced levels of glial fibrillary acidic protein in the tissue sections of animals treated with OP-1 mutant, evidencing the ability of the morphogen to inhibit glial scar formation, thereby stimulating nerve regeneration.

The ability of OP-1 mutant to stimulate peripheral nervous system axonal growth over extended distances can be demonstrated using the following model. Neurons of the peripheral nervous system can sprout new processes on their own following injury, but without guidance these sproutings typically fail to connect appropriately and die. Where the break is extensive, e.g., greater than 5 or 10 mm, regeneration is poor or nonexistent. Previous experiments with OP-1, show that morphogens stimulate peripheral nervous system axonal growth over extended distances, allowing repair and regeneration of damaged peripheral neural pathways.

In this example OP-1 mutant stimulation of time regeneration is demonstrated using the rat sciatic nerve model. The rat sciatic nerve can regenerate spontaneously across a 5 mm gap, and occasionally across a 10 mm gap, provided that the severed ends are inserted in a saline filled nerve guidance channel. In this experiment, nerve regeneration across at least a 12 mm gap is tested.

Adult female Sprague-Dawley rats (Charles River Laboratories, Inc.) weighing 230–250 g are anesthetized with intraperitoneal injections of sodium pentobarbital (35 mg/kg body weight). A skin incision is made parallel and just posterior to the femur. The avascular intermuscular plane between vastus lateralis and hamstring muscles are entered and followed to the loose fibroareolar tissue surrounding the sciatic nerve. The loose tissue is divided longitudinally thereby freeing the sciatic nerve over its full extent without devascularizing any portion. Under a surgical microscope the sciatic nerves are transected with microscissors at mid-thigh and grafted with an OP-1 morphon gel graft that separates the nerve stumps by 12 mm. The graft region is encased in a silicone tube 20 mm in length with a 1.5 mm inner diameter, the interior of which is filled with the mutant solution. Specifically, the central 12 mm of the tube consists of an OP-1 morphon gel prepared by mixing 1 to 5 mg of substantially pure OP-1 mutant produced with approximately 100 ml of MATRIGEL™ (from Collaborative Research, Inc., Bedford, Mass.), an extracellular matrix extract derived from mouse sarcoma tissue, and containing solubilized tissue basement membrane, including laminin, type IV collagen, heparin sulfate, proteoglycan and entactin, in phosphate-buffered saline. The mutant-filled tube then is implanted directly into the defect site, allowing 4 mm on each end to insert the nerve stumps. Each stump is abutted against the mutant gel and is secured in the silicone tube by three stitches of commercially available surgical 10–0 nylon through the epineurium, the fascicle protective sheath.

In addition to OP-1 mutant gel grafts, control grafts of empty silicone tubes, silicone tubes filled with gel only and "reverse" autografts, wherein 12 mm transected segments of the animal's sciatic nerve are rotated 180° C. prior to suturing, preferably also are grafted. All experiments preferably are performed in quadruplicate. All wounds preferably are closed by wound clips that are removed after 10 days. Rats can be grafted on both legs. At 3 weeks the animals are sacrificed, and the grafted segments removed and frozen on dry ice immediately. Frozen sections then are cut throughout the graft site, and examined for axonal regeneration by immunofluorescent staining using anti-neurofilament antibodies labeled with fluorescein (obtained, for example, from Sigma Chemical Co., St. Louis).

It is contemplated that regeneration of the sciatic nerve can occur across the entire 12 mm distance in all graft sites when the gap is filled with the OP-1 mutant gel. By contrast, empty silicone tubes, gel alone and reverse autografts do not show nerve regeneration.

IV. GENERAL REMARKS

It will be understood and appreciated that any of the foregoing means for assessing attributes such as folding, solubility, stability, surface binding/adherence, bio-activity, etc., can be performed using mutant constructs other than OP-1 based mutants. All that is required is a comparative assessment of the native TGF-β superfamily protein and the mutant construct's attributes. Thus, for example, a mutant which retains the preferred folding attributes of native protein X but which has acquired the neural tissue differentiation attributes of native protein Y can be readily identified using the experimental paradigms and guidance provided herein. The skilled artisan will recognize a preferred construct as one having all the desired attributes optimally combined, with optimal not intended to necessarily mean maximal expression of any one particular attribute. Rather, optimal is intended to mean expression of each desired attribute such that the combined expression is suitable for the circumstances and/or uses contemplated by the artisan.

The invention may be embodied in other specific forms without departing from the spirit and scope thereof. Accordingly, other embodiments are within the following claims.

SEQUENCE LISTING

```
<160> NUMBER OF SEQ ID NOS: 90

<210> SEQ ID NO 1
<211> LENGTH: 35
<212> TYPE: PRT
<213> ORGANISM: Drosophila melanogaster
<220> FEATURE:
<223> OTHER INFORMATION: 60-A

<400> SEQUENCE: 1

Ala Pro Thr Arg Leu Gly Ala Leu Pro Val Leu Tyr His Leu Asn Asp
1               5                   10                  15

Glu Asn Val Asn Leu Lys Lys Tyr Arg Asn Met Ile Val Lys Ser Cys
            20                  25                  30

Gly Cys His
        35

<210> SEQ ID NO 2
<211> LENGTH: 35
<212> TYPE: PRT
<213> ORGANISM: Homo sapiens
<220> FEATURE:
<223> OTHER INFORMATION: BMP-2

<400> SEQUENCE: 2

Val Pro Thr Glu Leu Ser Ala Ile Ser Met Leu Tyr Leu Asp Glu Asn
1               5                   10                  15

Glu Lys Val Val Leu Lys Asn Tyr Gln Asp Met Val Val Glu Gly Cys
            20                  25                  30

Gly Cys Arg
        35

<210> SEQ ID NO 3
<211> LENGTH: 35
<212> TYPE: PRT
<213> ORGANISM: Homo sapiens
<220> FEATURE:
<223> OTHER INFORMATION: BMP-3

<400> SEQUENCE: 3

Val Pro Glu Lys Met Ser Ser Leu Ser Ile Leu Phe Phe Asp Glu Asn
1               5                   10                  15

Lys Asn Val Val Leu Lys Val Tyr Pro Asn Met Thr Val Glu Ser Cys
            20                  25                  30

Ala Cys Arg
        35

<210> SEQ ID NO 4
<211> LENGTH: 35
<212> TYPE: PRT
<213> ORGANISM: Homo sapiens
```

```
<220> FEATURE:
<223> OTHER INFORMATION: BMP-4

<400> SEQUENCE: 4

Val Pro Thr Glu Leu Ser Ala Ile Ser Met Leu Tyr Leu Asp Glu Tyr
1               5                   10                  15

Asp Lys Val Val Leu Lys Asn Tyr Gln Glu Met Val Val Glu Gly Cys
            20                  25                  30

Gly Cys Arg
        35

<210> SEQ ID NO 5
<211> LENGTH: 35
<212> TYPE: PRT
<213> ORGANISM: Homo sapiens
<220> FEATURE:
<223> OTHER INFORMATION: BMP-5

<400> SEQUENCE: 5

Ala Pro Thr Lys Leu Asn Ala Ile Ser Val Leu Tyr Phe Asp Asp Ser
1               5                   10                  15

Ser Asn Val Ile Leu Lys Lys Tyr Arg Asn Met Val Val Arg Ser Cys
            20                  25                  30

Gly Cys His
        35

<210> SEQ ID NO 6
<211> LENGTH: 35
<212> TYPE: PRT
<213> ORGANISM: Homo sapiens
<220> FEATURE:
<223> OTHER INFORMATION: BMP-6

<400> SEQUENCE: 6

Ala Pro Thr Lys Leu Asn Ala Ile Ser Val Leu Tyr Phe Asp Asp Asn
1               5                   10                  15

Ser Asn Val Ile Leu Lys Lys Tyr Arg Asn Met Val Val Arg Ala Cys
            20                  25                  30

Gly Cys His
        35

<210> SEQ ID NO 7
<211> LENGTH: 36
<212> TYPE: PRT
<213> ORGANISM: Homo sapiens
<220> FEATURE:
<223> OTHER INFORMATION: BMP-9

<400> SEQUENCE: 7

Val Pro Thr Lys Leu Ser Pro Ile Ser Val Leu Tyr Lys Asp Asp Met
1               5                   10                  15

Gly Val Pro Thr Leu Lys Tyr His Tyr Glu Gly Met Ser Val Ala Glu
            20                  25                  30

Cys Gly Cys Arg
        35

<210> SEQ ID NO 8
<211> LENGTH: 35
<212> TYPE: PRT
<213> ORGANISM: Homo sapiens
<220> FEATURE:
<223> OTHER INFORMATION: BMP-10
```

-continued

```
<400> SEQUENCE: 8

Val Pro Thr Lys Leu Glu Pro Ile Ser Ile Leu Tyr Leu Asp Lys Gly
1               5                   10                  15

Val Val Thr Tyr Lys Phe Lys Tyr Glu Gly Met Ala Val Ser Glu Cys
            20                  25                  30

Gly Cys Arg
        35

<210> SEQ ID NO 9
<211> LENGTH: 35
<212> TYPE: PRT
<213> ORGANISM: Homo sapiens
<220> FEATURE:
<223> OTHER INFORMATION: BMP-11

<400> SEQUENCE: 9

Thr Pro Thr Lys Met Ser Pro Ile Asn Met Leu Tyr Phe Asn Asp Lys
1               5                   10                  15

Gln Gln Ile Ile Tyr Gly Lys Ile Pro Gly Met Val Val Asp Arg Cys
            20                  25                  30

Gly Cys Ser
        35

<210> SEQ ID NO 10
<211> LENGTH: 35
<212> TYPE: PRT
<213> ORGANISM: Bos taurus
<220> FEATURE:
<223> OTHER INFORMATION: CDMP-2

<400> SEQUENCE: 10

Val Pro Thr Lys Leu Thr Pro Ile Ser Ile Leu Tyr Ile Asp Ala Gly
1               5                   10                  15

Asn Asn Val Val Tyr Asn Glu Tyr Glu Met Val Val Glu Ser Cys
            20                  25                  30

Gly Cys Arg
        35

<210> SEQ ID NO 11
<211> LENGTH: 36
<212> TYPE: PRT
<213> ORGANISM: Gallus gallus
<220> FEATURE:
<223> OTHER INFORMATION: Dorsalin

<400> SEQUENCE: 11

Val Pro Thr Lys Leu Asp Ala Ile Ser Ile Leu Tyr Lys Asp Asp Ala
1               5                   10                  15

Gly Val Pro Thr Leu Ile Tyr Asn Tyr Glu Gly Met Lys Val Ala Glu
            20                  25                  30

Cys Gly Cys Arg
        35

<210> SEQ ID NO 12
<211> LENGTH: 35
<212> TYPE: PRT
<213> ORGANISM: Drosophila melanogaster
<220> FEATURE:
<223> OTHER INFORMATION: DPP

<400> SEQUENCE: 12

Val Pro Thr Gln Leu Asp Ser Val Ala Met Leu Tyr Leu Asn Asp Gln
```

-continued

```
                1               5                  10                 15
Ser Thr Val Val Leu Lys Asn Tyr Gln Glu Met Thr Val Val Gly Cys
                    20                 25                 30

Gly Cys Arg
        35

<210> SEQ ID NO 13
<211> LENGTH: 35
<212> TYPE: PRT
<213> ORGANISM: Mus musculus
<220> FEATURE:
<223> OTHER INFORMATION: GDF-1

<400> SEQUENCE: 13

Val Pro Glu Arg Leu Ser Pro Ile Ser Val Leu Phe Phe Asp Asn Glu
1               5                  10                 15

Asp Asn Val Val Leu Arg His Tyr Glu Asp Met Val Val Asp Glu Cys
                20                 25                 30

Gly Cys Arg
        35

<210> SEQ ID NO 14
<211> LENGTH: 35
<212> TYPE: PRT
<213> ORGANISM: Mus musculus
<220> FEATURE:
<223> OTHER INFORMATION: GDF-3

<400> SEQUENCE: 14

Val Pro Thr Lys Leu Ser Pro Ile Ser Met Leu Tyr Gln Asp Ser Asp
1               5                  10                 15

Lys Asn Val Ile Leu Arg His Tyr Glu Asp Met Val Val Asp Glu Cys
                20                 25                 30

Gly Cys Gly
        35

<210> SEQ ID NO 15
<211> LENGTH: 35
<212> TYPE: PRT
<213> ORGANISM: Homo sapiens
<220> FEATURE:
<223> OTHER INFORMATION: GDF-5

<400> SEQUENCE: 15

Val Pro Thr Arg Leu Ser Pro Ile Ser Ile Leu Phe Ile Asp Ser Ala
1               5                  10                 15

Asn Asn Val Val Tyr Lys Gln Tyr Glu Asp Met Val Val Glu Ser Cys
                20                 25                 30

Gly Cys Arg
        35

<210> SEQ ID NO 16
<211> LENGTH: 35
<212> TYPE: PRT
<213> ORGANISM: Mus musculus
<220> FEATURE:
<223> OTHER INFORMATION: GDF-6

<400> SEQUENCE: 16

Val Pro Thr Lys Leu Thr Pro Ile Ser Ile Leu Tyr Ile Asp Ala Gly
1               5                  10                 15

Asn Asn Val Val Tyr Lys Gln Tyr Glu Asp Met Val Val Glu Ser Cys
```

```
                        20                  25                  30

Gly Cys Arg
        35

<210> SEQ ID NO 17
<211> LENGTH: 35
<212> TYPE: PRT
<213> ORGANISM: Mus musculus
<220> FEATURE:
<223> OTHER INFORMATION: GDF-7

<400> SEQUENCE: 17

Val Pro Ala Arg Leu Ser Pro Ile Ser Ile Leu Tyr Ile Asp Ala Ala
1               5                   10                  15

Asn Asn Val Val Tyr Lys Gln Tyr Glu Asp Met Val Val Glu Ala Cys
            20                  25                  30

Gly Cys Arg
        35

<210> SEQ ID NO 18
<211> LENGTH: 35
<212> TYPE: PRT
<213> ORGANISM: Mus musculus
<220> FEATURE:
<223> OTHER INFORMATION: GDF-9

<400> SEQUENCE: 18

Val Pro Gly Lys Tyr Ser Pro Leu Ser Val Leu Thr Ile Glu Pro Asp
1               5                   10                  15

Gly Ser Ile Ala Tyr Lys Glu Tyr Glu Asp Met Ile Ala Thr Arg Cys
            20                  25                  30

Thr Cys Arg
        35

<210> SEQ ID NO 19
<211> LENGTH: 32
<212> TYPE: PRT
<213> ORGANISM: Homo sapiens
<220> FEATURE:
<223> OTHER INFORMATION: GDNF

<400> SEQUENCE: 19

Arg Pro Ile Ala Phe Asp Asp Asp Leu Ser Phe Leu Asp Asp Asn Leu
1               5                   10                  15

Val Tyr His Ile Leu Arg Lys His Ser Ala Lys Arg Cys Gly Cys Ile
            20                  25                  30

<210> SEQ ID NO 20
<211> LENGTH: 38
<212> TYPE: PRT
<213> ORGANISM: Homo sapiens
<220> FEATURE:
<223> OTHER INFORMATION: Inhibin Alpha

<400> SEQUENCE: 20

Ala Ala Leu Pro Gly Thr Met Arg Pro Leu His Val Arg Thr Thr Ser
1               5                   10                  15

Asp Gly Gly Tyr Ser Phe Lys Tyr Glu Thr Val Pro Asn Leu Leu Thr
            20                  25                  30

Gln His Cys Ala Cys Ile
        35
```

```
<210> SEQ ID NO 21
<211> LENGTH: 35
<212> TYPE: PRT
<213> ORGANISM: Homo sapiens
<220> FEATURE:
<223> OTHER INFORMATION: Inhibin BetaA

<400> SEQUENCE: 21

Val Pro Thr Lys Leu Arg Pro Met Ser Met Leu Tyr Tyr Asp Asp Gly
1               5                   10                  15

Gln Asn Ile Ile Lys Lys Asp Ile Gln Asn Met Ile Val Glu Glu Cys
            20                  25                  30

Gly Cys Ser
        35

<210> SEQ ID NO 22
<211> LENGTH: 35
<212> TYPE: PRT
<213> ORGANISM: Homo sapiens
<220> FEATURE:
<223> OTHER INFORMATION: Inhibin BetaB

<400> SEQUENCE: 22

Ile Pro Thr Lys Leu Ser Thr Met Ser Met Leu Tyr Phe Asp Asp Glu
1               5                   10                  15

Tyr Asn Ile Val Lys Arg Asp Val Pro Asn Met Ile Val Glu Glu Cys
            20                  25                  30

Gly Cys Ala
        35

<210> SEQ ID NO 23
<211> LENGTH: 35
<212> TYPE: PRT
<213> ORGANISM: Homo sapiens
<220> FEATURE:
<223> OTHER INFORMATION: Inhibin BetaC

<400> SEQUENCE: 23

Val Pro Thr Ala Arg Arg Pro Leu Ser Leu Leu Tyr Tyr Asp Arg Asp
1               5                   10                  15

Ser Asn Ile Val Lys Thr Asp Ile Pro Asp Met Val Val Glu Ala Cys
            20                  25                  30

Gly Cys Ser
        35

<210> SEQ ID NO 24
<211> LENGTH: 34
<212> TYPE: PRT
<213> ORGANISM: Homo sapiens
<220> FEATURE:
<223> OTHER INFORMATION: MIS

<400> SEQUENCE: 24

Val Pro Thr Ala Tyr Ala Gly Lys Leu Leu Ile Ser Leu Ser Glu Glu
1               5                   10                  15

Arg Ile Ser Ala His His Val Pro Asn Met Val Ala Thr Glu Cys Gly
            20                  25                  30

Cys Arg

<210> SEQ ID NO 25
<211> LENGTH: 34
<212> TYPE: PRT
<213> ORGANISM: Mus musculus
```

```
<220> FEATURE:
<223> OTHER INFORMATION: Nodal

<400> SEQUENCE: 25

Ala Pro Val Lys Thr Lys Pro Leu Ser Met Leu Tyr Val Asp Asn Gly
1               5                   10                  15

Arg Val Leu Leu Glu His His Lys Asp Met Ile Val Glu Glu Cys Gly
            20                  25                  30

Cys Leu

<210> SEQ ID NO 26
<211> LENGTH: 35
<212> TYPE: PRT
<213> ORGANISM: Homo sapiens
<220> FEATURE:
<223> OTHER INFORMATION: OP-2

<400> SEQUENCE: 26

Ala Pro Thr Lys Leu Ser Ala Thr Ser Val Leu Tyr Tyr Asp Ser Ser
1               5                   10                  15

Asn Asn Val Ile Leu Arg Lys His Arg Asn Met Val Val Lys Ala Cys
            20                  25                  30

Gly Cys His
        35

<210> SEQ ID NO 27
<211> LENGTH: 35
<212> TYPE: PRT
<213> ORGANISM: Mus musculus
<220> FEATURE:
<223> OTHER INFORMATION: OP-3

<400> SEQUENCE: 27

Val Pro Thr Glu Leu Ser Ala Ile Ser Leu Leu Tyr Tyr Asp Arg Asn
1               5                   10                  15

Asn Asn Val Ile Leu Arg Arg Glu Arg Asn Met Val Val Gln Ala Cys
            20                  25                  30

Gly Cys His
        35

<210> SEQ ID NO 28
<211> LENGTH: 35
<212> TYPE: PRT
<213> ORGANISM: Drosophila melanogaster
<220> FEATURE:
<223> OTHER INFORMATION: Screw

<400> SEQUENCE: 28

Val Pro Thr Val Leu Gly Ala Ile Thr Ile Leu Arg Tyr Leu Asn Glu
1               5                   10                  15

Asp Ile Ile Asp Leu Thr Lys Tyr Gln Lys Ala Val Ala Lys Glu Cys
            20                  25                  30

Gly Cys His
        35

<210> SEQ ID NO 29
<211> LENGTH: 34
<212> TYPE: PRT
<213> ORGANISM: Homo sapiens
<220> FEATURE:
<223> OTHER INFORMATION: TGF-Beta1

<400> SEQUENCE: 29
```

-continued

Val Pro Gln Ala Leu Glu Pro Leu Pro Ile Val Tyr Tyr Val Gly Arg
1               5                   10                  15

Lys Pro Lys Val Glu Gln Leu Ser Asn Met Ile Val Arg Ser Cys Lys
            20                  25                  30

Cys Ser

<210> SEQ ID NO 30
<211> LENGTH: 34
<212> TYPE: PRT
<213> ORGANISM: Homo sapiens
<220> FEATURE:
<223> OTHER INFORMATION: TGF-Beta2

<400> SEQUENCE: 30

Val Ser Gln Asp Leu Glu Pro Leu Thr Ile Leu Tyr Tyr Ile Gly Lys
1               5                   10                  15

Thr Pro Lys Ile Glu Gln Leu Ser Asn Met Ile Val Lys Ser Cys Lys
            20                  25                  30

Cys Ser

<210> SEQ ID NO 31
<211> LENGTH: 34
<212> TYPE: PRT
<213> ORGANISM: Homo sapiens
<220> FEATURE:
<223> OTHER INFORMATION: TGF-Beta3

<400> SEQUENCE: 31

Val Pro Gln Asp Leu Glu Pro Leu Thr Ile Leu Tyr Tyr Val Gly Arg
1               5                   10                  15

Thr Pro Lys Val Glu Gln Leu Ser Asn Met Val Val Lys Ser Cys Lys
            20                  25                  30

Cys Ser

<210> SEQ ID NO 32
<211> LENGTH: 34
<212> TYPE: PRT
<213> ORGANISM: Gallus gallus
<220> FEATURE:
<223> OTHER INFORMATION: TGF-Beta4

<400> SEQUENCE: 32

Val Pro Gln Thr Leu Asp Pro Leu Pro Ile Ile Tyr Tyr Val Gly Arg
1               5                   10                  15

Asn Val Arg Val Glu Gln Leu Ser Asn Met Val Val Arg Ala Cys Lys
            20                  25                  30

Cys Ser

<210> SEQ ID NO 33
<211> LENGTH: 34
<212> TYPE: PRT
<213> ORGANISM: Xenopus laevis
<220> FEATURE:
<223> OTHER INFORMATION: TGF-Beta5

<400> SEQUENCE: 33

Val Pro Asp Val Leu Glu Pro Leu Pro Ile Ile Tyr Tyr Val Gly Arg
1               5                   10                  15

Thr Ala Lys Val Glu Gln Leu Ser Asn Met Val Val Arg Ser Cys Asn
            20                  25                  30

Cys Ser

<210> SEQ ID NO 34
<211> LENGTH: 35
<212> TYPE: PRT
<213> ORGANISM: Strongylocentrotus purpuratus
<220> FEATURE:
<223> OTHER INFORMATION: UNIVIN

<400> SEQUENCE: 34

Ala Pro Thr Lys Leu Ser Gly Ile Ser Met Leu Tyr Phe Asp Asn Asn
1               5                   10                  15

Glu Asn Val Val Leu Arg Gln Tyr Glu Asp Met Val Val Glu Ala Cys
            20                  25                  30

Gly Cys Arg
        35

<210> SEQ ID NO 35
<211> LENGTH: 35
<212> TYPE: PRT
<213> ORGANISM: Xenopus laevis
<220> FEATURE:
<223> OTHER INFORMATION: VG-1

<400> SEQUENCE: 35

Val Pro Thr Lys Met Ser Pro Ile Ser Met Leu Phe Tyr Asp Asn Asn
1               5                   10                  15

Asp Asn Val Val Leu Arg His Tyr Glu Asn Met Ala Val Asp Glu Cys
            20                  25                  30

Gly Cys Arg
        35

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence:synthetic
      primer
<220> FEATURE:
<221> NAME/KEY: CDS
<222> LOCATION: (1)..(21)

<400> SEQUENCE: 36 atg tcc acg ggg agc aaa cag                                       21
Met Ser Thr Gly Ser Lys Gln
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: amino acids
      encoded by synthetic primer

<400> SEQUENCE: 37

Met Ser Thr Gly Ser Lys Gln
1               5

<210> SEQ ID NO 38
<211> LENGTH: 1822
<212> TYPE: DNA
<213> ORGANISM: Homo sapiens
<220> FEATURE:
<221> NAME/KEY: CDS
<222> LOCATION: (49)..(1341)
<223> OTHER INFORMATION: Morphogenic Protein OP1

<400> SEQUENCE: 38

| | | | |
|---|---|---|---|
| ggtgcgggcc cggagcccgg agcccgggta gcgcgtagag ccggcgcg atg cac gtg | | | 57 |
| | Met | His Val | |
| | 1 | | |

| cgc tca ctg cga gct gcg gcg ccg cac agc ttc gtg gcg ctc tgg gca | 105 |
|---|---|
| Arg Ser Leu Arg Ala Ala Ala Pro His Ser Phe Val Ala Leu Trp Ala | |
| 5           10            15 | |

| ccc ctg ttc ctg ctg cgc tcc gcc ctg gcc gac ttc agc ctg gac aac | 153 |
|---|---|
| Pro Leu Phe Leu Leu Arg Ser Ala Leu Ala Asp Phe Ser Leu Asp Asn | |
| 20           25            30            35 | |

| gag gtg cac tcg agc ttc atc cac cgg cgc ctc cgc agc cag gag cgg | 201 |
|---|---|
| Glu Val His Ser Ser Phe Ile His Arg Arg Leu Arg Ser Gln Glu Arg | |
|              40            45            50 | |

| cgg gag atg cag cgc gag atc ctc tcc att ttg ggc ttg ccc cac cgc | 249 |
|---|---|
| Arg Glu Met Gln Arg Glu Ile Leu Ser Ile Leu Gly Leu Pro His Arg | |
|       55            60            65 | |

| ccg cgc ccg cac ctc cag ggc aag cac aac tcg gca ccc atg ttc atg | 297 |
|---|---|
| Pro Arg Pro His Leu Gln Gly Lys His Asn Ser Ala Pro Met Phe Met | |
| 70            75            80 | |

| ctg gac ctg tac aac gcc atg gcg gtg gag gag ggc ggc ggg ccc ggc | 345 |
|---|---|
| Leu Asp Leu Tyr Asn Ala Met Ala Val Glu Glu Gly Gly Gly Pro Gly | |
|       85            90            95 | |

| ggc cag ggc ttc tcc tac ccc tac aag gcc gtc ttc agt acc cag ggc | 393 |
|---|---|
| Gly Gln Gly Phe Ser Tyr Pro Tyr Lys Ala Val Phe Ser Thr Gln Gly | |
| 100           105           110           115 | |

| ccc cct ctg gcc agc ctg caa gat agc cat ttc ctc acc gac gcc gac | 441 |
|---|---|
| Pro Pro Leu Ala Ser Leu Gln Asp Ser His Phe Leu Thr Asp Ala Asp | |
|       120           125           130 | |

| atg gtc atg agc ttc gtc aac ctc gtg gaa cat gac aag gaa ttc ttc | 489 |
|---|---|
| Met Val Met Ser Phe Val Asn Leu Val Glu His Asp Lys Glu Phe Phe | |
|       135           140           145 | |

| cac cca cgc tac cac cat cga gag ttc cgg ttt gat ctt tcc aag atc | 537 |
|---|---|
| His Pro Arg Tyr His His Arg Glu Phe Arg Phe Asp Leu Ser Lys Ile | |
|       150           155           160 | |

| cca gaa ggg gaa gct gtc acg gca gcc gaa ttc cgg atc tac aag gac | 585 |
|---|---|
| Pro Glu Gly Glu Ala Val Thr Ala Ala Glu Phe Arg Ile Tyr Lys Asp | |
| 165           170           175 | |

| tac atc cgg gaa cgc ttc gac aat gag acg ttc cgg atc agc gtt tat | 633 |
|---|---|
| Tyr Ile Arg Glu Arg Phe Asp Asn Glu Thr Phe Arg Ile Ser Val Tyr | |
| 180           185           190           195 | |

| cag gtg ctc cag gag cac ttg ggc agg gaa tcg gat ctc ttc ctg ctc | 681 |
|---|---|
| Gln Val Leu Gln Glu His Leu Gly Arg Glu Ser Asp Leu Phe Leu Leu | |
|       200           205           210 | |

| gac agc cgt acc ctc tgg gcc tcg gag gag ggc tgg ctg gtg ttt gac | 729 |
|---|---|
| Asp Ser Arg Thr Leu Trp Ala Ser Glu Glu Gly Trp Leu Val Phe Asp | |
|       215           220           225 | |

| atc aca gcc acc agc aac cac tgg gtg gtc aat ccg cgg cac aac ctg | 777 |
|---|---|
| Ile Thr Ala Thr Ser Asn His Trp Val Val Asn Pro Arg His Asn Leu | |
|       230           235           240 | |

| ggc ctg cag ctc tcg gtg gag acg ctg gat ggg cag agc atc aac ccc | 825 |
|---|---|
| Gly Leu Gln Leu Ser Val Glu Thr Leu Asp Gly Gln Ser Ile Asn Pro | |
| 245           250           255 | |

| aag ttg gcg ggc ctg att ggg cgg cac ggg ccc cag aac aag cag ccc | 873 |
|---|---|
| Lys Leu Ala Gly Leu Ile Gly Arg His Gly Pro Gln Asn Lys Gln Pro | |
| 260           265           270           275 | |

| ttc atg gtg gct ttc ttc aag gcc acg gag gtc cac ttc cgc agc atc | 921 |
|---|---|
| Phe Met Val Ala Phe Phe Lys Ala Thr Glu Val His Phe Arg Ser Ile | |

```
cgg tcc acg ggg agc aaa cag cgc agc cag aac cgc tcc aag acg ccc      969
Arg Ser Thr Gly Ser Lys Gln Arg Ser Gln Asn Arg Ser Lys Thr Pro
            295                 300                 305 aag aac cag gaa gcc ctg cgg atg gcc aac gtg gca gag aac agc agc     1017
Lys Asn Gln Glu Ala Leu Arg Met Ala Asn Val Ala Glu Asn Ser Ser
        310                 315                 320 agc gac cag agg cag gcc tgt aag aag cac gag ctg tat gtc agc ttc     1065
Ser Asp Gln Arg Gln Ala Cys Lys Lys His Glu Leu Tyr Val Ser Phe
    325                 330                 335 cga gac ctg ggc tgg cag gac tgg atc atc gcg cct gaa ggc tac gcc     1113
Arg Asp Leu Gly Trp Gln Asp Trp Ile Ile Ala Pro Glu Gly Tyr Ala
340                 345                 350                 355 gcc tac tac tgt gag ggg gag tgt gcc ttc cct ctg aac tcc tac atg     1161
Ala Tyr Tyr Cys Glu Gly Glu Cys Ala Phe Pro Leu Asn Ser Tyr Met
                360                 365                 370 aac gcc acc aac cac gcc atc gtg cag acg ctg gtc cac ttc atc aac     1209
Asn Ala Thr Asn His Ala Ile Val Gln Thr Leu Val His Phe Ile Asn
            375                 380                 385 ccg gaa acg gtg ccc aag ccc tgc tgt gcg ccc acg cag ctc aat gcc     1257
Pro Glu Thr Val Pro Lys Pro Cys Cys Ala Pro Thr Gln Leu Asn Ala
        390                 395                 400 atc tcc gtc ctc tac ttc gat gac agc tcc aac gtc atc ctg aag aaa    1305
Ile Ser Val Leu Tyr Phe Asp Asp Ser Ser Asn Val Ile Leu Lys Lys
    405                 410                 415 tac aga aac atg gtg gtc cgg gcc tgt ggc tgc cac tagctcctcc         1351
Tyr Arg Asn Met Val Val Arg Ala Cys Gly Cys His
420                 425                 430 gagaattcag acccttgggg gccaagtttt tctggatcct ccattgctcg ccttggccag  1411
gaaccagcag accaactgcc ttttgtgaga ccttcccctc cctatcccca actttaaagg  1471
tgtgagagta ttaggaaaca tgagcagcat atggcttttg atcagttttt cagtggcagc  1531
atccaatgaa caagatccta caagctgtgc aggcaaaacc tagcaggaaa aaaaaacaac  1591
gcataaagaa aaatggccgg gccaggtcat tggctgggaa gtctcagcca tgcacggact  1651
cgtttccaga ggtaattatg agcgcctacc agccaggcca cccagccgtg ggaggaaggg  1711
ggcgtggcaa ggggtgggca cattggtgtc tgtgcgaaag gaaaattgac ccggaagttc  1771
ctgtaataaa tgtcacaata aaacgaatga atgaaaaaaa aaaaaaaaa a            1822
```

<210> SEQ ID NO 39
<211> LENGTH: 431
<212> TYPE: PRT
<213> ORGANISM: Homo sapiens
<220> FEATURE:
<223> OTHER INFORMATION: Morphogenic protein OP1

<400> SEQUENCE: 39

```
Met His Val Arg Ser Leu Arg Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
65                  70                  75                  80
```

```
Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Ser Ser Asn Val Ile
                405                 410                 415

Leu Lys Lys Tyr Arg Asn Met Val Val Arg Ala Cys Gly Cys His
                420                 425                 430

<210> SEQ ID NO 40
<211> LENGTH: 98
<212> TYPE: PRT
<213> ORGANISM: Homo sapiens
<220> FEATURE:
<223> OTHER INFORMATION: TGF-Beta1

<400> SEQUENCE: 40

Cys Cys Val Arg Gln Leu Tyr Ile Asp Phe Arg Lys Asp Leu Gly Trp
1               5                   10                  15
```

-continued

Lys Trp Ile His Glu Pro Lys Gly Tyr His Ala Asn Phe Cys Leu Gly
             20                  25                  30

Pro Cys Pro Tyr Ile Trp Ser Leu Asp Thr Gln Tyr Ser Lys Val Leu
             35                  40                  45

Ala Leu Tyr Asn Gln His Asn Pro Gly Ala Ser Ala Ala Pro Cys Cys
 50                      55                  60

Val Pro Gln Ala Leu Glu Pro Leu Pro Ile Val Tyr Tyr Val Gly Arg
65                       70                  75                  80

Lys Pro Lys Val Glu Gln Leu Ser Asn Met Ile Val Arg Ser Cys Lys
                 85                  90                  95

Cys Ser

<210> SEQ ID NO 41
<211> LENGTH: 98
<212> TYPE: PRT
<213> ORGANISM: Homo sapiens
<220> FEATURE:
<223> OTHER INFORMATION: TGF-Beta2

<400> SEQUENCE: 41

Cys Cys Leu Arg Pro Leu Tyr Ile Asp Phe Lys Arg Asp Leu Gly Trp
1               5                   10                  15

Lys Trp Ile His Glu Pro Lys Gly Tyr Asn Ala Asn Phe Cys Ala Gly
             20                  25                  30

Ala Cys Pro Tyr Leu Trp Ser Ser Asp Thr Gln His Ser Arg Val Leu
             35                  40                  45

Ser Leu Tyr Asn Thr Ile Asn Pro Glu Ala Ser Ala Ser Pro Cys Cys
 50                      55                  60

Val Ser Gln Asp Leu Glu Pro Leu Thr Ile Leu Tyr Tyr Ile Gly Lys
65                       70                  75                  80

Thr Pro Lys Ile Glu Gln Leu Ser Asn Met Ile Val Lys Ser Cys Lys
                 85                  90                  95

Cys Ser

<210> SEQ ID NO 42
<211> LENGTH: 98
<212> TYPE: PRT
<213> ORGANISM: Homo sapiens
<220> FEATURE:
<223> OTHER INFORMATION: TGF-Beta3

<400> SEQUENCE: 42

Cys Cys Val Arg Pro Leu Tyr Ile Asp Phe Arg Gln Asp Leu Gly Trp
1               5                   10                  15

Lys Trp Val His Glu Pro Lys Gly Tyr Tyr Ala Asn Phe Cys Ser Gly
             20                  25                  30

Pro Cys Pro Tyr Leu Arg Ser Ala Asp Thr Thr His Ser Thr Val Leu
             35                  40                  45

Gly Leu Tyr Asn Thr Leu Asn Pro Glu Ala Ser Ala Ser Pro Cys Cys
 50                      55                  60

Val Pro Gln Asp Leu Glu Pro Leu Thr Ile Leu Tyr Tyr Val Gly Arg
65                       70                  75                  80

Thr Pro Lys Val Glu Gln Leu Ser Asn Met Val Val Lys Ser Cys Lys
                 85                  90                  95

Cys Ser

<210> SEQ ID NO 43

<211> LENGTH: 98
<212> TYPE: PRT
<213> ORGANISM: Gallus gallus
<220> FEATURE:
<223> OTHER INFORMATION: TGF-Beta4

<400> SEQUENCE: 43

Cys Cys Val Arg Pro Leu Tyr Ile Asp Phe Arg Lys Asp Leu Gln Trp
1               5                   10                  15

Lys Trp Ile His Glu Pro Lys Gly Tyr Met Ala Asn Phe Cys Met Gly
            20                  25                  30

Pro Cys Pro Tyr Ile Trp Ser Ala Asp Thr Gln Tyr Thr Lys Val Leu
        35                  40                  45

Ala Leu Tyr Asn Gln His Asn Pro Gly Ala Ser Ala Ala Pro Cys Cys
    50                  55                  60

Val Pro Gln Thr Leu Asp Pro Leu Pro Ile Ile Tyr Tyr Val Gly Arg
65                  70                  75                  80

Asn Val Arg Val Glu Gln Leu Ser Asn Met Val Val Arg Ala Cys Lys
                85                  90                  95

Cys Ser

<210> SEQ ID NO 44
<211> LENGTH: 98
<212> TYPE: PRT
<213> ORGANISM: Xenopus laevis
<220> FEATURE:
<223> OTHER INFORMATION: TGF-Beta5

<400> SEQUENCE: 44

Cys Cys Val Lys Pro Leu Tyr Ile Asn Phe Arg Lys Asp Leu Gly Trp
1               5                   10                  15

Lys Trp Ile His Glu Pro Lys Gly Tyr Glu Ala Asn Tyr Cys Leu Gly
            20                  25                  30

Asn Cys Pro Tyr Ile Trp Ser Met Asp Thr Gln Tyr Ser Lys Val Leu
        35                  40                  45

Ser Leu Tyr Asn Gln Asn Asn Pro Gly Ala Ser Ile Ser Pro Cys Cys
    50                  55                  60

Val Pro Asp Val Leu Glu Pro Leu Pro Ile Ile Tyr Tyr Val Gly Arg
65                  70                  75                  80

Thr Ala Lys Val Glu Gln Leu Ser Asn Met Val Val Arg Ser Cys Asn
                85                  90                  95

Cys Ser

<210> SEQ ID NO 45
<211> LENGTH: 102
<212> TYPE: PRT
<213> ORGANISM: Drosophila melanogaster
<220> FEATURE:
<223> OTHER INFORMATION: DPP

<400> SEQUENCE: 45

Cys Arg Arg His Ser Leu Tyr Val Asp Phe Ser Asp Val Gly Trp Asp
1               5                   10                  15

Asp Trp Ile Val Ala Pro Leu Gly Tyr Asp Ala Tyr Tyr Cys His Gly
            20                  25                  30

Lys Cys Pro Phe Pro Leu Ala Asp His Phe Asn Ser Thr Asn His Ala
        35                  40                  45

Val Val Gln Thr Leu Val Asn Asn Met Asn Pro Gly Lys Val Pro Lys
    50                  55                  60

Ala Cys Cys Val Pro Thr Gln Leu Asp Ser Val Ala Met Leu Tyr Leu
65                  70                  75                  80

Asn Asp Gln Ser Thr Val Val Leu Lys Asn Tyr Gln Glu Met Thr Val
                85                  90                  95

Val Gly Cys Gly Cys Arg
            100

<210> SEQ ID NO 46
<211> LENGTH: 102
<212> TYPE: PRT
<213> ORGANISM: Xenopus laevis
<220> FEATURE:
<223> OTHER INFORMATION: VG1

<400> SEQUENCE: 46

Cys Lys Lys Arg His Leu Tyr Val Glu Phe Lys Asp Val Gly Trp Gln
1               5                   10                  15

Asn Trp Val Ile Ala Pro Gln Gly Tyr Met Ala Asn Tyr Cys Tyr Gly
                20                  25                  30

Glu Cys Pro Tyr Pro Leu Thr Glu Ile Leu Asn Gly Ser Asn His Ala
            35                  40                  45

Ile Leu Gln Thr Leu Val His Ser Ile Glu Pro Glu Asp Ile Pro Leu
    50                  55                  60

Pro Cys Cys Val Pro Thr Lys Met Ser Pro Ile Ser Met Leu Phe Tyr
65                  70                  75                  80

Asp Asn Asn Asp Asn Val Val Leu Arg His Tyr Glu Asn Met Ala Val
                85                  90                  95

Asp Glu Cys Gly Cys Arg
            100

<210> SEQ ID NO 47
<211> LENGTH: 102
<212> TYPE: PRT
<213> ORGANISM: Mus musculus
<220> FEATURE:
<223> OTHER INFORMATION: VGR1

<400> SEQUENCE: 47

Cys Lys Lys His Glu Leu Tyr Val Ser Phe Gln Asp Leu Gly Trp Gln
1               5                   10                  15

Asp Trp Ile Ile Ala Pro Lys Gly Tyr Ala Ala Asn Tyr Cys Asp Gly
                20                  25                  30

Glu Cys Ser Phe Pro Leu Asn Ala His Met Asn Ala Thr Asn His Ala
            35                  40                  45

Ile Val Gln Thr Leu Val His Leu Met Asn Pro Glu Tyr Val Pro Lys
    50                  55                  60

Pro Cys Cys Ala Pro Thr Lys Leu Asn Ala Ile Ser Val Leu Tyr Phe
65                  70                  75                  80

Asp Asp Asn Ser Asn Val Ile Leu Lys Lys Tyr Arg Asn Met Val Val
                85                  90                  95

Arg Ala Cys Gly Cys His
            100

<210> SEQ ID NO 48
<211> LENGTH: 118
<212> TYPE: PRT
<213> ORGANISM: Drosophila melanogaster
<220> FEATURE:
<223> OTHER INFORMATION: 60A

```
<400> SEQUENCE: 48

Cys Gln Met Gln Thr Leu Tyr Ile Asp Phe Lys Asp Leu Gly Trp His
1               5                   10                  15

Asp Trp Ile Ile Ala Pro Glu Gly Tyr Gly Ala Phe Tyr Cys Ser Gly
                20                  25                  30

Glu Cys Asn Phe Pro Leu Asn Ala His Met Asn Ala Thr Asn His Ala
            35                  40                  45

Ile Val Gln Thr Leu Val His Leu Leu Glu Pro Lys Lys Val Pro Lys
        50                  55                  60

Pro Cys Cys Ala Pro Thr Arg Leu Gly Ala Leu Pro Val Leu Tyr His
65                  70                  75                  80

Pro Cys Cys Ala Pro Thr Arg Leu Gly Ala Leu Pro Val Leu Tyr His
                85                  90                  95

Leu Asn Asp Glu Asn Val Asn Leu Lys Lys Tyr Arg Asn Met Ile Val
                100                 105                 110

Lys Ser Cys Gly Cys His
            115

<210> SEQ ID NO 49
<211> LENGTH: 101
<212> TYPE: PRT
<213> ORGANISM: Homo sapiens
<220> FEATURE:
<223> OTHER INFORMATION: BMP-2A

<400> SEQUENCE: 49

Cys Lys Arg His Pro Leu Tyr Val Asp Phe Ser Asp Val Gly Trp Asn
1               5                   10                  15

Asp Trp Ile Val Ala Pro Pro Gly Tyr His Ala Phe Tyr Cys His Gly
                20                  25                  30

Glu Cys Pro Phe Pro Leu Ala Asp His Leu Asn Ser Thr Asn His Ala
            35                  40                  45

Ile Val Gln Thr Leu Val Asn Ser Val Asn Ser Lys Ile Pro Lys Ala
        50                  55                  60

Cys Cys Val Pro Thr Glu Leu Ser Ala Ile Ser Met Leu Tyr Leu Asp
65                  70                  75                  80

Glu Asn Glu Lys Val Val Leu Lys Asn Tyr Gln Asp Met Val Val Glu
                85                  90                  95

Gly Cys Gly Cys Arg
            100

<210> SEQ ID NO 50
<211> LENGTH: 103
<212> TYPE: PRT
<213> ORGANISM: Homo sapiens
<220> FEATURE:
<223> OTHER INFORMATION: BMP3

<400> SEQUENCE: 50

Cys Ala Arg Arg Tyr Leu Lys Val Asp Phe Ala Asp Ile Gly Trp Ser
1               5                   10                  15

Glu Trp Ile Ile Ser Pro Lys Ser Phe Asp Ala Tyr Tyr Cys Ser Gly
                20                  25                  30

Ala Cys Gln Phe Pro Met Pro Lys Ser Leu Lys Pro Ser Asn His Ala
            35                  40                  45

Thr Ile Gln Ser Ile Val Arg Ala Val Gly Val Val Pro Gly Ile Pro
        50                  55                  60
```

Glu Pro Cys Cys Val Pro Glu Lys Met Ser Ser Leu Ser Ile Leu Phe
65                  70                  75                  80

Phe Asp Glu Asn Lys Asn Val Val Leu Lys Val Tyr Pro Asn Met Thr
                85                  90                  95

Val Glu Ser Cys Ala Cys Arg
            100

<210> SEQ ID NO 51
<211> LENGTH: 101
<212> TYPE: PRT
<213> ORGANISM: Homo sapiens
<220> FEATURE:
<223> OTHER INFORMATION: BMP-4

<400> SEQUENCE: 51

Cys Arg Arg His Ser Leu Tyr Val Asp Phe Ser Asp Val Gly Trp Asn
1               5                   10                  15

Asp Trp Ile Val Ala Pro Pro Gly Tyr Gln Ala Phe Tyr Cys His Gly
                20                  25                  30

Asp Cys Pro Phe Pro Leu Ala Asp His Leu Asn Ser Thr Asn His Ala
            35                  40                  45

Ile Val Gln Thr Leu Val Asn Ser Val Asn Ser Ile Pro Lys Ala
        50                  55                  60

Cys Cys Val Pro Thr Glu Leu Ser Ala Ile Ser Met Leu Tyr Leu Asp
65                  70                  75                  80

Glu Tyr Asp Lys Val Val Leu Lys Asn Tyr Gln Glu Met Val Val Glu
                85                  90                  95

Gly Cys Gly Cys Arg
            100

<210> SEQ ID NO 52
<211> LENGTH: 102
<212> TYPE: PRT
<213> ORGANISM: Homo sapiens
<220> FEATURE:
<223> OTHER INFORMATION: BMP-5

<400> SEQUENCE: 52

Cys Lys Lys His Glu Leu Tyr Val Ser Phe Arg Asp Leu Gly Trp Gln
1               5                   10                  15

Asp Trp Ile Ile Ala Pro Glu Gly Tyr Ala Ala Phe Tyr Cys Asp Gly
                20                  25                  30

Glu Cys Ser Phe Pro Leu Asn Ala His Met Asn Ala Thr Asn His Ala
            35                  40                  45

Ile Val Gln Thr Leu Val His Leu Met Phe Pro Asp His Val Pro Lys
        50                  55                  60

Pro Cys Cys Ala Pro Thr Lys Leu Asn Ala Ile Ser Val Leu Tyr Phe
65                  70                  75                  80

Asp Asp Ser Ser Asn Val Ile Leu Lys Lys Tyr Arg Asn Met Val Val
                85                  90                  95

Arg Ser Cys Gly Cys His
            100

<210> SEQ ID NO 53
<211> LENGTH: 102
<212> TYPE: PRT
<213> ORGANISM: Homo sapiens
<220> FEATURE:
<223> OTHER INFORMATION: BMP-6

<400> SEQUENCE: 53

Cys Arg Lys His Glu Leu Tyr Val Ser Phe Gln Asp Leu Gly Trp Gln
1               5                   10                  15

Asp Trp Ile Ile Ala Pro Lys Gly Tyr Ala Ala Asn Tyr Cys Asp Gly
            20                  25                  30

Glu Cys Ser Phe Pro Leu Asn Ala His Met Asn Ala Thr Asn His Ala
        35                  40                  45

Ile Val Gln Thr Leu Val His Leu Met Asn Pro Glu Tyr Val Pro Lys
    50                  55                  60

Pro Cys Cys Ala Pro Thr Lys Leu Asn Ala Ile Ser Val Leu Tyr Phe
65                  70                  75                  80

Asp Asp Asn Ser Asn Val Glu Leu Lys Lys Tyr Arg Asn Met Val Val
                85                  90                  95

Arg Ala Cys Gly Cys His
            100

<210> SEQ ID NO 54
<211> LENGTH: 103
<212> TYPE: PRT
<213> ORGANISM: Gallus gallus
<220> FEATURE:
<223> OTHER INFORMATION: DORSALIN

<400> SEQUENCE: 54

Cys Arg Arg Thr Ser Leu His Val Asn Phe Lys Glu Ile Gly Trp Asp
1               5                   10                  15

Ser Trp Ile Ile Ala Pro Lys Asp Tyr Glu Ala Phe Glu Cys Lys Gly
            20                  25                  30

Gly Cys Phe Phe Pro Leu Thr Asp Asn Val Thr Pro Thr Lys His Ala
        35                  40                  45

Ile Val Gln Thr Leu Val His Leu Gln Asn Pro Lys Ala Ser Lys
    50                  55                  60

Ala Cys Cys Val Pro Thr Lys Leu Asp Ala Ile Ser Ile Leu Tyr Lys
65                  70                  75                  80

Asp Asp Ala Gly Val Pro Thr Leu Ile Tyr Asn Tyr Glu Gly Met Lys
                85                  90                  95

Val Ala Glu Cys Gly Cys Arg
            100

<210> SEQ ID NO 55
<211> LENGTH: 102
<212> TYPE: PRT
<213> ORGANISM: Homo sapiens
<220> FEATURE:
<223> OTHER INFORMATION: OP-1

<400> SEQUENCE: 55

Cys Lys Lys His Glu Leu Tyr Val Ser Phe Arg Asp Leu Gly Trp Gln
1               5                   10                  15

Asp Trp Ile Ile Ala Pro Glu Gly Tyr Ala Ala Tyr Tyr Cys Glu Gly
            20                  25                  30

Glu Cys Ala Phe Pro Leu Asn Ser Tyr Met Asn Ala Thr Asn His Ala
        35                  40                  45

Ile Val Gln Thr Leu Val His Phe Ile Asn Pro Glu Thr Val Pro Lys
    50                  55                  60

Pro Cys Cys Ala Pro Thr Gln Leu Asn Ala Ile Ser Val Leu Tyr Phe
65                  70                  75                  80

```
Asp Asp Ser Ser Asn Val Ile Leu Lys Lys Tyr Arg Asn Met Val Val
                85                  90                  95
Arg Ala Cys Gly Cys His
            100

<210> SEQ ID NO 56
<211> LENGTH: 102
<212> TYPE: PRT
<213> ORGANISM: Homo sapiens
<220> FEATURE:
<223> OTHER INFORMATION: OP-2

<400> SEQUENCE: 56

Cys Arg Arg His Glu Leu Tyr Val Ser Phe Gln Asp Leu Gly Trp Leu
1               5                   10                  15
Asp Trp Val Ile Ala Pro Gln Gly Tyr Ser Ala Tyr Tyr Cys Glu Gly
            20                  25                  30
Glu Cys Ser Phe Pro Leu Asp Ser Cys Met Asn Ala Thr Asn His Ala
        35                  40                  45
Ile Leu Gln Ser Leu Val His Leu Met Lys Pro Asn Ala Val Pro Lys
    50                  55                  60
Ala Cys Cys Ala Pro Thr Lys Leu Ser Ala Thr Ser Val Leu Tyr Tyr
65                  70                  75                  80
Asp Ser Ser Asn Asn Val Ile Leu Arg Lys His Arg Asn Met Val Val
                85                  90                  95
Lys Ala Cys Gly Cys His
            100

<210> SEQ ID NO 57
<211> LENGTH: 102
<212> TYPE: PRT
<213> ORGANISM: Mus musculus
<220> FEATURE:
<223> OTHER INFORMATION: OP-3

<400> SEQUENCE: 57

Cys Arg Arg His Glu Leu Tyr Val Ser Phe Arg Asp Leu Gly Trp Leu
1               5                   10                  15
Asp Ser Val Ile Ala Pro Gln Gly Tyr Ser Ala Tyr Tyr Cys Ala Gly
            20                  25                  30
Glu Cys Ile Tyr Pro Leu Asn Ser Cys Met Asn Ser Thr Asn His Ala
        35                  40                  45
Thr Met Gln Ala Leu Val His Leu Met Lys Pro Asp Ile Ile Pro Lys
    50                  55                  60
Val Cys Cys Val Pro Thr Glu Leu Ser Ala Ile Ser Leu Leu Tyr Tyr
65                  70                  75                  80
Asp Arg Asn Asn Asn Val Ile Leu Arg Arg Glu Arg Asn Met Val Val
                85                  90                  95
Gln Ala Cys Gly Cys His
            100

<210> SEQ ID NO 58
<211> LENGTH: 107
<212> TYPE: PRT
<213> ORGANISM: Mus musculus
<220> FEATURE:
<223> OTHER INFORMATION: GDF-1

<400> SEQUENCE: 58
```

```
Cys Arg Thr Arg Arg Leu His Val Ser Phe Arg Glu Val Gly Trp His
1               5                   10                  15

Arg Trp Val Ile Ala Pro Arg Gly Phe Leu Ala Asn Phe Cys Gln Gly
                20                  25                  30

Thr Cys Ala Leu Pro Glu Thr Leu Arg Gly Pro Gly Pro Pro Ala
            35                  40                  45

Leu Asn His Ala Val Leu Arg Ala Leu Met His Ala Ala Pro Thr
        50                  55                  60

Pro Gly Ala Gly Ser Pro Cys Cys Val Pro Glu Arg Leu Ser Pro Ile
65                  70                  75                  80

Ser Val Leu Phe Phe Asp Asn Ser Asp Asn Val Val Leu Arg His Tyr
                85                  90                  95

Glu Asp Met Val Val Asp Glu Cys Gly Cys Arg
                100                 105
```

<210> SEQ ID NO 59
<211> LENGTH: 101
<212> TYPE: PRT
<213> ORGANISM: Mus musculus
<220> FEATURE:
<223> OTHER INFORMATION: GDF-3

<400> SEQUENCE: 59

```
Cys His Arg His Gln Leu Phe Ile Asn Phe Gln Asp Leu Gly Trp His
1               5                   10                  15

Lys Trp Val Ile Ala Pro Lys Gly Phe Met Ala Asn Tyr Cys His Gly
                20                  25                  30

Glu Cys Pro Phe Ser Met Thr Thr Tyr Leu Asn Ser Ser Asn Tyr Ala
            35                  40                  45

Phe Met Gln Ala Leu Met His Met Ala Asp Pro Lys Val Pro Lys Ala
        50                  55                  60

Val Cys Val Pro Thr Lys Leu Ser Pro Ile Ser Met Leu Tyr Gln Asp
65                  70                  75                  80

Ser Asp Lys Asn Val Ile Leu Arg His Tyr Glu Asp Met Val Val Asp
                85                  90                  95

Glu Cys Gly Cys Gly
            100
```

<210> SEQ ID NO 60
<211> LENGTH: 102
<212> TYPE: PRT
<213> ORGANISM: Mus musculus
<220> FEATURE:
<223> OTHER INFORMATION: GDF-9

<400> SEQUENCE: 60

```
Cys Glu Leu His Asp Phe Arg Leu Ser Phe Ser Gln Leu Lys Trp Asp
1               5                   10                  15

Asn Trp Ile Val Ala Pro His Arg Tyr Asn Pro Arg Tyr Cys Lys Gly
                20                  25                  30

Asp Cys Pro Arg Ala Val Arg His Arg Tyr Gly Ser Pro Val His Thr
            35                  40                  45

Met Val Gln Asn Ile Ile Tyr Glu Lys Leu Asp Pro Ser Val Pro Arg
        50                  55                  60

Pro Ser Cys Val Pro Gly Lys Tyr Ser Pro Leu Ser Val Leu Thr Ile
65                  70                  75                  80

Glu Pro Asp Gly Ser Ile Ala Tyr Lys Glu Tyr Glu Asp Met Ile Ala
                85                  90                  95
```

```
Thr Arg Cys Thr Cys Arg
            100

<210> SEQ ID NO 61
<211> LENGTH: 105
<212> TYPE: PRT
<213> ORGANISM: Homo sapiens
<220> FEATURE:
<223> OTHER INFORMATION: INHIBIN-Alpha

<400> SEQUENCE: 61

Cys His Arg Val Ala Leu Asn Ile Ser Phe Gln Glu Leu Gly Trp Glu
1               5                   10                  15

Arg Trp Ile Val Tyr Pro Pro Ser Phe Ile Phe His Tyr Cys His Gly
            20                  25                  30

Gly Cys Gly Leu His Ile Pro Pro Asn Leu Ser Leu Pro Val Pro Gly
        35                  40                  45

Ala Pro Pro Thr Pro Ala Gln Pro Tyr Ser Leu Leu Pro Gly Ala Gln
    50                  55                  60

Pro Cys Cys Ala Ala Leu Pro Gly Thr Met Arg Pro Leu His Val Arg
65                  70                  75                  80

Thr Thr Ser Asp Gly Gly Tyr Ser Phe Lys Tyr Glu Thr Val Pro Asn
                85                  90                  95

Leu Leu Thr Gln His Cys Ala Cys Ile
            100                 105

<210> SEQ ID NO 62
<211> LENGTH: 106
<212> TYPE: PRT
<213> ORGANISM: Bos taurus
<220> FEATURE:
<223> OTHER INFORMATION: INHIBIN-BetaA

<400> SEQUENCE: 62

Cys Cys Lys Lys Gln Phe Phe Val Ser Phe Lys Asp Ile Gly Trp Asn
1               5                   10                  15

Asp Trp Ile Ile Ala Pro Ser Gly Tyr His Ala Asn Tyr Cys Glu Gly
            20                  25                  30

Glu Cys Pro Ser His Ile Ala Gly Thr Ser Gly Ser Ser Leu Ser Phe
        35                  40                  45

His Ser Thr Val Ile Asn His Tyr Arg Met Arg Gly His Ser Pro Phe
    50                  55                  60

Ala Asn Leu Lys Ser Cys Cys Val Pro Thr Lys Leu Arg Pro Met Ser
65                  70                  75                  80

Met Leu Tyr Tyr Asp Asp Gly Gln Asn Ile Ile Lys Lys Asp Ile Gln
                85                  90                  95

Asn Met Ile Val Glu Glu Cys Gly Cys Ser
            100                 105

<210> SEQ ID NO 63
<211> LENGTH: 106
<212> TYPE: PRT
<213> ORGANISM: Homo sapiens
<220> FEATURE:
<223> OTHER INFORMATION: INHIBIN-Betab

<400> SEQUENCE: 63

Cys Cys Lys Lys Gln Phe Phe Val Ser Phe Lys Asp Ile Gly Trp Asn
1               5                   10                  15
```

```
Asp Trp Ile Ile Ala Pro Ser Gly Tyr His Ala Asn Tyr Cys Glu Gly
            20                  25                  30

Glu Cys Pro Ser His Ile Ala Gly Thr Ser Gly Ser Ser Leu Ser Phe
            35                  40                  45

His Ser Thr Val Ile Asn His Tyr Arg Met Arg Gly His Ser Pro Phe
        50                  55                  60

Ala Asn Leu Lys Ser Cys Cys Val Pro Thr Lys Leu Arg Pro Met Ser
 65              70                  75                  80

Met Leu Tyr Tyr Asp Asp Gly Gln Asn Ile Ile Lys Lys Asp Ile Gln
                85                  90                  95

Asn Met Ile Val Glu Glu Cys Gly Cys Ser
            100                 105
```

<210> SEQ ID NO 64
<211> LENGTH: 98
<212> TYPE: PRT
<213> ORGANISM: Artificial Sequence
<220> FEATURE:
<223> OTHER INFORMATION: Description of Artificial Sequence:  TGF-B
      SUBGROUP SEQUENCE PATTERN
<220> FEATURE:
<221> NAME/KEY: misc_feature
<222> LOCATION: (12)..(12)
<223> OTHER INFORMATION: Xaa12 can be Arg or Lys
<220> FEATURE:
<221> NAME/KEY: misc_feature
<222> LOCATION: (26)..(26)
<223> OTHER INFORMATION: Xaa26 can be Ala, Arg, Asn, Asp, Cys, Glu, Gln,
      Gly, His, Ile, Leu, Lys, Met, Phe, Pro, Ser, Thr, Trp, Tyr or Val
<220> FEATURE:
<221> NAME/KEY: misc_feature
<222> LOCATION: (31)..(31)
<223> OTHER INFORMATION: Xaa31 can be Ala, Arg, Asn, Asp, Cys, Glu, Gln,
      Gly, His, Ile, Leu, Lys, Met, Phe, Pro, Ser, Thr, Trp, Tyr or Val
<220> FEATURE:
<221> NAME/KEY: misc_feature
<222> LOCATION: (33)..(33)
<223> OTHER INFORMATION: Xaa33 can be Ala, Gly, Pro, Ser or Thr
<220> FEATURE:
<221> NAME/KEY: misc_feature
<222> LOCATION: (37)..(37)
<223> OTHER INFORMATION: Xaa37 can be Ile, Leu lys, Met or Val
<220> FEATURE:
<221> NAME/KEY: misc_feature
<222> LOCATION: (40)..(40)
<223> OTHER INFORMATION: Xaa40 can be Ala, Arg, Asn, Asp, Cys, Glu, Gln,
      Gly, His, Ile, Leu, Lys, Met, Phe, Pro, Ser, Thr, Trp, Tyr or Val
<220> FEATURE:
<221> NAME/KEY: misc_feature
<222> LOCATION: (44)..(44)
<223> OTHER INFORMATION: Xaa44 can be His, Phe, Trp or Tyr
<220> FEATURE:
<221> NAME/KEY: misc_feature
<222> LOCATION: (46)..(46)
<223> OTHER INFORMATION: Xaa46 can be Arg or Lys
<220> FEATURE:
<221> NAME/KEY: misc_feature
<222> LOCATION: (49)..(49)
<223> OTHER INFORMATION: Xaa49 can be Ala, Gly, Pro, Ser or Thr
<220> FEATURE:
<221> NAME/KEY: misc_feature
<222> LOCATION: (53)..(54)
<223> OTHER INFORMATION: Xaa53 can be Arg, Asn, Asp, Gln, Glu, His, Lys,
      Ser or Thr; Xaa54 can be Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: misc_feature
<222> LOCATION: (57)..(57)
<223> OTHER INFORMATION: Xaa57 can be Ala, Arg, Asn, Asp, Cys, Glu, Gln,
      Gly, His, Ile, Leu, Lys, Met, Phe, Pro, Ser, Thr, Trp, Tyr or Val
<220> FEATURE:
<221> NAME/KEY: misc_feature
<222> LOCATION: (61)..(61)

```
<223> OTHER INFORMATION: Xaa61 can be Ala, Gly, Pro, Ser or Thr
<220> FEATURE:
<221> NAME/KEY: misc_feature
<222> LOCATION: (68)..(68)
<223> OTHER INFORMATION: Xaa68 can be Ala, Arg, Asn, Asp, Cys, Glu, Gln,
      Gly, His, Ile, Leu, Lys, Met, Phe, Pro, Ser, Thr, Trp, Tyr or Val
<220> FEATURE:
<221> NAME/KEY: misc_feature
<222> LOCATION: (73)..(73)
<223> OTHER INFORMATION: Xaa73 can be Ala, Gly, Pro, Ser or Thr
<220> FEATURE:
<221> NAME/KEY: misc_feature
<222> LOCATION: (75)..(75)
<223> OTHER INFORMATION: Xaa75 can be Ile, Leu, Met or Val
<220> FEATURE:
<221> NAME/KEY: misc_feature
<222> LOCATION: (81)..(82)
<223> OTHER INFORMATION: Xaa81 can be Arg, Asn, Asp, Gln, Glu, His, Lys,
      Ser or Thr; Xaa82 can be Ala, Gly, Pro, Ser, or Thr
<220> FEATURE:
<221> NAME/KEY: misc_feature
<222> LOCATION: (91)..(91)
<223> OTHER INFORMATION: Xaa91 can be any Ile or Val
<220> FEATURE:
<221> NAME/KEY: misc_feature
<222> LOCATION: (93)..(93)
<223> OTHER INFORMATION: Xaa93 can be Arg or Lys

<400> SEQUENCE: 64

Cys Cys Val Arg Pro Leu Tyr Ile Asp Phe Arg Xaa Asp Leu Gly Trp
1               5                  10                  15

Lys Trp Ile His Glu Pro Lys Gly Tyr Xaa Ala Asn Phe Cys Xaa Gly
            20                  25                  30

Xaa Cys Pro Tyr Xaa Trp Ser Xaa Asp Thr Gln Xaa Ser Xaa Val Leu
        35                  40                  45

Xaa Leu Tyr Asn Xaa Xaa Asn Pro Xaa Ala Ser Ala Xaa Pro Cys Cys
    50                  55                  60

Val Pro Gln Xaa Leu Glu Pro Leu Xaa Ile Xaa Tyr Tyr Val Gly Arg
65                  70                  75                  80

Xaa Xaa Lys Val Glu Gln Leu Ser Asn Met Xaa Val Xaa Ser Cys Lys
                85                  90                  95

Cys Ser

<210> SEQ ID NO 65
<211> LENGTH: 104
<212> TYPE: PRT
<213> ORGANISM: Artificial Sequence
<220> FEATURE:
<223> OTHER INFORMATION: Description of Artificial Sequence:
      VG/DPP SUBGROUP SEQUENCE PATTERN
<220> FEATURE:
<221> NAME/KEY: misc_feature
<222> LOCATION: (2)..(5)
<223> OTHER INFORMATION: Xaa2 can be Arg or Lys; Xaa3 can be Arg or Lys;
      Xaa4 and Xaa5 independently can be Arg, Asn, Asp, Glu, Gln, His,
      Lys, Ser or Thr
<220> FEATURE:
<221> NAME/KEY: misc_feature
<222> LOCATION: (9)..(9)
<223> OTHER INFORMATION: Xaa9 can be Arg, Asn, Asp, Glu, Gln, His, Lys,
      Ser or Thr
<220> FEATURE:
<221> NAME/KEY: misc_feature
<222> LOCATION: (11)..(11)
<223> OTHER INFORMATION: Xaa11 can be Arg, Asn, Asp, Glu, Gln, His, Lys,
      Ser or Thr
<220> FEATURE:
<221> NAME/KEY: misc_feature
<222> LOCATION: (13)..(13)
<223> OTHER INFORMATION: Xaa13 can be Ile, Leu, Met, or Val
<220> FEATURE:
```

```
<221> NAME/KEY: misc_feature
<222> LOCATION: (16)..(16)
<223> OTHER INFORMATION: Xaa16 can be Arg, Asn, Asp, Glu, Gln, His, Lys,
      Ser or Thr
<220> FEATURE:
<221> NAME/KEY: misc_feature
<222> LOCATION: (23)..(23)
<223> OTHER INFORMATION: Xaa23 can be Arg, Gln, Glu or Lys
<220> FEATURE:
<221> NAME/KEY: misc_feature
<222> LOCATION: (26)..(26)
<223> OTHER INFORMATION: Xaa26 can be Ala, Arg, Asn, Asp, Cys, Glu, Gln,
      Gly, His, Ile, Leu, Lys, Met, Phe, Pro, Ser, Thr, Trp, Tyr or Val
<220> FEATURE:
<221> NAME/KEY: misc_feature
<222> LOCATION: (28)..(28)
<223> OTHER INFORMATION: Xaa28 can be Phe, Trp or Tyr
<220> FEATURE:
<221> NAME/KEY: misc_feature
<222> LOCATION: (31)..(31)
<223> OTHER INFORMATION: Xaa31 can be Arg, Asn, Asp, Glu, Gln, His, Lys,
      Ser or Thr
<220> FEATURE:
<221> NAME/KEY: misc_feature
<222> LOCATION: (33)..(33)
<223> OTHER INFORMATION: Xaa33 can be Asp or Glu
<220> FEATURE:
<221> NAME/KEY: misc_feature
<222> LOCATION: (35)..(35)
<223> OTHER INFORMATION: Xaa35 can be Ala, Arg, Asn, Asp, Cys, Glu, Gln,
      Gly, His, Ile, Leu, Lys, Met, Phe, Pro, Ser, Thr, Trp, Tyr or Val
<220> FEATURE:
<221> NAME/KEY: misc_feature
<222> LOCATION: (39)..(42)
<223> OTHER INFORMATION: Xaa39, Xaa40 and Xaa41 independently can be
      Ala, Arg, Asn, Asp, Cys, Glu, Gln, Gly, His, Ile, Leu, Lys, Met,
      Phe, Pro, Ser, Thr, Trp, Tyr or Val; Xaa42 can be Leu or Met
<220> FEATURE:
<221> NAME/KEY: misc_feature
<222> LOCATION: (44)..(44)
<223> OTHER INFORMATION: Xaa44 can be Ala, Gly, Pro, Ser or Thr
<220> FEATURE:
<221> NAME/KEY: misc_feature
<222> LOCATION: (50)..(50)
<223> OTHER INFORMATION: Xaa50 can be Ile or Val
<220> FEATURE:
<221> NAME/KEY: misc_feature
<222> LOCATION: (55)..(57)
<223> OTHER INFORMATION: Xaa55 can be Arg, Asn, Asp, Glu, Gln, His, Lys,
      Ser or Thr; Xaa56 can be Ala, Arg, Asn, Asp, Cys, Glu, Gln, Gly,
      His, Ile, Leu, Lys, Met, Phe, Pro, Ser, Thr, Trp, Tyr or Val;
      Xaa57 can be Ile, Leu, Met or Val
<220> FEATURE:
<221> NAME/KEY: misc_feature
<222> LOCATION: (58)..(60)
<223> OTHER INFORMATION: Xaa58 can be Arg, Asn, Asp, Glu, Gln, His, Lys,
      Ser or Thr; Xaa59 and Xaa60 independently can be Ala, Arg, Asn,
      Asp, Cys, Glu, Gln, Gly, His, Ile, Leu, Lys, Met, Phe, Pro, Ser,
      Thr, Trp, Tyr, Val or a peptide bond
<220> FEATURE:
<221> NAME/KEY: misc_feature
<222> LOCATION: (61)..(63)
<223> OTHER INFORMATION: Xaa61 can be Arg, Asn, Asp, Glu, Gln, His, Lys,
      Ser or Thr; Xaa62 can be Ala, Arg, Asn, Asp, Cys, Glu, Gln, Gly,
      His, Ile, Leu, Lys, Met, Phe, Pro, Ser, Thr, Trp, Tyr or Val;
      Xaa63 can be Ile or Val
<220> FEATURE:
<221> NAME/KEY: misc_feature
<222> LOCATION: (66)..(66)
<223> OTHER INFORMATION: Xaa66 can be Ala Gly, Pro, Ser or Thr
<220> FEATURE:
<221> NAME/KEY: misc_feature
<222> LOCATION: (69)..(69)
<223> OTHER INFORMATION: Xaa69 can be Ala, Arg, Asn, Asp, Cys, Glu, Gln,
      Gly, His, Ile, Leu, Lys, Met, Phe, Pro, Ser, Thr, Trp, Tyr or Val
<220> FEATURE:
<221> NAME/KEY: misc_feature
<222> LOCATION: (72)..(72)
<223> OTHER INFORMATION: Xaa72 can be Arg, Gln, Glu or Lys
```

-continued

```
<220> FEATURE:
<221> NAME/KEY: misc_feature
<222> LOCATION: (74)..(74)
<223> OTHER INFORMATION: Xaa74 can be Arg, Asn, Asp, Glu, Gln, His, Lys, Ser or Thr
<220> FEATURE:
<221> NAME/KEY: misc_feature
<222> LOCATION: (76)..(76)
<223> OTHER INFORMATION: Xaa76 can be Ile or Val
<220> FEATURE:
<221> NAME/KEY: misc_feature
<222> LOCATION: (78)..(78)
<223> OTHER INFORMATION: Xaa78 can be Ile, Leu, Met or Val
<220> FEATURE:
<221> NAME/KEY: misc_feature
<222> LOCATION: (81)..(81)
<223> OTHER INFORMATION: Xaa81 can be Cys, Ile, Leu, Met, Phe, Trp, Tyr or Val
<220> FEATURE:
<221> NAME/KEY: misc_feature
<222> LOCATION: (83)..(85)
<223> OTHER INFORMATION: Xaa83 can be Asn, Asp or Glu; Xaa84 can be Arg, Asn, Asp, Glu, Gln, His, Lys, Ser or Thr; Xaa85 can be Ala, Arg, Asn, Asp, Cys, Glu, Gln, Gly, His, Ile, Leu, Lys, Met, Phe, Pro, Ser, Thr, Trp, Tyr, Val or a peptide bond
<220> FEATURE:
<221> NAME/KEY: misc_feature
<222> LOCATION: (86)..(87)
<223> OTHER INFORMATION: Xaa86 and Xaa87 independently can be Arg, Asn, Asp, Glu, Gln, His, Lys, Ser or Thr
<220> FEATURE:
<221> NAME/KEY: misc_feature
<222> LOCATION: (89)..(89)
<223> OTHER INFORMATION: Xaa89 can Ile or Val
<220> FEATURE:
<221> NAME/KEY: misc_feature
<222> LOCATION: (91)..(92)
<223> OTHER INFORMATION: Xaa91 can be Arg or Lys; Xaa92 can be Arg, Asn, Asp, Glu, Gln, His, Lys, Ser or Thr
<220> FEATURE:
<221> NAME/KEY: misc_feature
<222> LOCATION: (94)..(95)
<223> OTHER INFORMATION: Xaa94 can be Arg, Gln, Glu or Lys; Xaa95 can be Asn or Asp
<220> FEATURE:
<221> NAME/KEY: misc_feature
<222> LOCATION: (97)..(97)
<223> OTHER INFORMATION: Xaa97 can be Ala, Arg, Asn, Asp, Cys, Glu, Gln, Gly, His, Ile, Leu, Lys, Met, Phe, Pro, Ser, Thr, Trp, Tyr or Val
<220> FEATURE:
<221> NAME/KEY: misc_feature
<222> LOCATION: (99)..(100)
<223> OTHER INFORMATION: Xaa99 can be Arg, Gln, Glu or Lys; Xaa100 can be Ala Gly, Pro, Ser or Thr
<220> FEATURE:
<221> NAME/KEY: misc_feature
<222> LOCATION: (104)..(104)
<223> OTHER INFORMATION: Xaa104 can be Arg, Asn, Asp, Glu, Gln, His, Lys, Ser or Thr

<400> SEQUENCE: 65

Cys Xaa Xaa Xaa Xaa Leu Tyr Val Xaa Phe Xaa Asp Xaa Gly Trp Xaa
1 5 10 15

Asp Trp Ile Ile Ala Pro Xaa Gly Tyr Xaa Ala Xaa Tyr Cys Xaa Gly
20 25 30

Xaa Cys Xaa Phe Pro Leu Xaa Xaa Xaa Xaa Asn Xaa Thr Asn His Ala
35 40 45

Ile Xaa Gln Thr Leu Val Xaa Xaa Xaa Xaa Xaa Xaa Xaa Xaa Xaa Pro
50 55 60

Lys Xaa Cys Cys Xaa Pro Thr Xaa Leu Xaa Ala Xaa Ser Xaa Leu Tyr
65 70 75 80

Xaa Asp Xaa Xaa Xaa Xaa Xaa Val Xaa Leu Xaa Xaa Tyr Xaa Xaa Met
85 90 95

Xaa Val Xaa Xaa Cys Gly Cys Xaa
            100

<210> SEQ ID NO 66
<211> LENGTH: 107
<212> TYPE: PRT
<213> ORGANISM: Artificial Sequence
<220> FEATURE:
<223> OTHER INFORMATION: Description of Artificial Sequence:
      GDF SUBGROUP PATTERN
<220> FEATURE:
<221> NAME/KEY: misc_feature
<222> LOCATION: (2)..(3)
<223> OTHER INFORMATION: Xaa2 can be Arg, Asn, Asp, Glu, Gln, His, Lys,
      Ser or Thr; Xaa3 can be Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: misc_feature
<222> LOCATION: (4)..(5)
<223> OTHER INFORMATION: Xaa4 and Xaa5 independently can be Arg, Asn,
      Asp, Glu, Gln, His, Lys, Ser or Thr
<220> FEATURE:
<221> NAME/KEY: misc_feature
<222> LOCATION: (6)..(8)
<223> OTHER INFORMATION: Xaa6 can be Cys, Ile, Leu, Met, Phe, Trp,
      Tyr or Val; Xaa7 can be Ala, Arg, Asn, Asp, Cys, Glu, Gln, Gly,
      His, Ile, Leu, Lys, Met, Phe, Pro,Ser, Thr, Trp, Tyr or Val; Xaa8
      can be Ile, Leu, Met or Val
<220> FEATURE:
<221> NAME/KEY: misc_feature
<222> LOCATION: (9)..(9)
<223> OTHER INFORMATION: Xaa9 can be Arg, Asn, Asp, Glu, Gln, His, Lys,
      Ser or Thr
<220> FEATURE:
<221> NAME/KEY: misc_feature
<222> LOCATION: (11)..(14)
<223> OTHER INFORMATION: Xaa11 and Xaa12 independently can be Arg, Asn,
      Asp, Glu, Gln, His, Lys, Ser or Thr; Xaa13 can be Ile, Leu, Met or
      Val; Xaa14 can be Ala, Arg, Asn, Asp, Cys, Glu, Gln, Gly, His,
      Ile, Leu, Lys, Met, Phe, Pro, Ser, Thr, Trp, Tyr or Val
<220> FEATURE:
<221> NAME/KEY: misc_feature
<222> LOCATION: (16)..(17)
<223> OTHER INFORMATION: Xaa16 and Xaa17 independently can be Arg, Asn,
      Asp, Glu, Gln, His, Lys, Ser or Thr
<220> FEATURE:
<221> NAME/KEY: misc_feature
<222> LOCATION: (19)..(20)
<223> OTHER INFORMATION: Xaa19 and Xaa20 independently can be Ile or Val
<220> FEATURE:
<221> NAME/KEY: misc_feature
<222> LOCATION: (23)..(25)
<223> OTHER INFORMATION: Xaa23 can be Arg, Asn, Asp, Glu, Gln, His, Lys,
      Ser or Thr; Xaa24 can be Ala, Arg, Asn, Asp, Cys, Glu, Gln, Gly,
      His, Ile, Leu, Lys, Met, Phe, Pro, Ser, Thr, Trp, Tyr or Val;
      Xaa25 can be Phe, Trp or Tyr
<220> FEATURE:
<221> NAME/KEY: misc_feature
<222> LOCATION: (26)..(29)
<223> OTHER INFORMATION: Xaa26 can be Ala, Arg, Asn, Asp, Cys, Glu, Gln,
      Gly, His, Ile, Leu, Lys, Met, Phe, Pro, Ser, Thr, Trp, Tyr or Val;
      Xaa27 can be Ala Gly, Pro, Ser or Thr; Xaa28 can be Arg, Asn, Asp,
      Glu, Gln, His, Lys, Ser or Thr; Xaa29 can be Phe, Trp or Tyr
<220> FEATURE:
<221> NAME/KEY: misc_feature
<222> LOCATION: (31)..(31)
<223> OTHER INFORMATION: Xaa31 can be Arg, Asn, Asp, Glu, Gln, His, Lys,
      Ser or Thr
<220> FEATURE:
<221> NAME/KEY: misc_feature
<222> LOCATION: (33)..(33)
<223> OTHER INFORMATION: Xaa33 can be Arg, Asn, Asp, Glu, Gln, His, Lys,
      Ser or Thr
<220> FEATURE:
<221> NAME/KEY: misc_feature
<222> LOCATION: (35)..(37)
<223> OTHER INFORMATION: Xaa35 can be Ala, Gly, Pro, Ser or Thr; Xaa36

```
      can be Ala, Arg, Asn, Asp, Cys, Glu, Gln, Gly, His, Ile, Leu, Lys,
      Met, Phe, Pro, Ser, Thr, Trp, Tyr or Val; Xaa37 can be Ala, Gly,
      Pro, Ser or Thr
<220> FEATURE:
<221> NAME/KEY: misc_feature
<222> LOCATION: (38)..(39)
<223> OTHER INFORMATION: Xaa38 can be Ala, Arg, Asn, Asp, Cys, Glu, Gln,
      Gly, His, Ile, Leu, Lys, Met, Phe, Pro, Ser, Thr, Trp, Tyr or Val;
      Xaa39 can be Arg, Asn, Asp, Glu, Gln, His, Lys, Ser or Thr
<220> FEATURE:
<221> NAME/KEY: misc_feature
<222> LOCATION: (40)..(42)
<223> OTHER INFORMATION: Xaa40 to Xaa42 independently can be Ala, Arg,
      Asn, Asp, Cys, Glu, Gln, Gly, His, Ile, Leu, Lys, Met, Phe, Pro,
      Ser, Thr, Trp, Tyr or Val
<220> FEATURE:
<221> NAME/KEY: misc_feature
<222> LOCATION: (43)..(46)
<223> OTHER INFORMATION: Xaa43 to Xaa46 independently can be Ala, Arg,
      Asn, Asp, Cys, Glu, Gln, Gly, His, Ile, Leu, Lys, Met, Phe, Pro,
      Ser, Thr, Trp, Tyr, Val or a peptide bond
<220> FEATURE:
<221> NAME/KEY: misc_feature
<222> LOCATION: (47)..(48)
<223> OTHER INFORMATION: Xaa47 can be Ala, Arg, Asn, Asp, Cys, Glu, Gln,
      Gly, His, Ile, Leu, Lys, Met, Phe, Pro, Ser, Thr, Trp, Tyr or Val;
      Xaa48 can be Ala, Gly, Pro, Ser or Thr
<220> FEATURE:
<221> NAME/KEY: misc_feature
<222> LOCATION: (49)..(49)
<223> OTHER INFORMATION: Xaa49 can be Ala, Arg, Asn, Asp, Cys, Glu, Gln,
      Gly, His, Ile, Leu, Lys, Met, Phe, Pro, Ser, Thr, Trp, Tyr or Val
<220> FEATURE:
<221> NAME/KEY: misc_feature
<222> LOCATION: (50)..(53)
<223> OTHER INFORMATION: Xaa50 can be Ala, Arg, Asn, Asp, Cys, Glu, Gln,
      Gly, His, Ile, Leu, Lys, Met, Phe, Pro, Ser, Thr, Trp, Tyr or Val;
      Xaa51 can be His, Phe, Trp or Tyr; Xaa52 can be Ala, Gly, Pro, Ser
      or Thr; Xaa53 can be Cys, Ile, Leu, Met, Phe, Trp, Tyr or Val
<220> FEATURE:
<221> NAME/KEY: misc_feature
<222> LOCATION: (54)..(55)
<223> OTHER INFORMATION: Xaa54 can be Ile, Leu, Met or Val; Xaa55 can be
      Arg, Gln, Glu or Lys; Xaa56 can be Ala, Arg, Asn, Asp, Cys, Glu,
      Gln, Gly, His, Ile, Leu, Lys, Met, Phe, Pro, Ser, Thr, Trp, Tyr or
      Val; Xaa57 and Xaa58 independently can be Ile, Leu, Met or Val
<220> FEATURE:
<221> NAME/KEY: misc_feature
<222> LOCATION: (59)..(62)
<223> OTHER INFORMATION: Xaa59 can be His, Phe, Trp or Tyr; Xaa60, Xaa61
      and Xaa62 independently can be Ala, Arg, Asn, Asp, Cys, Glu, Gln,
      Gly, His, Ile, Leu, Lys, Met, Phe, Pro, Ser, Thr, Trp, Tyr or Val
<220> FEATURE:
<221> NAME/KEY: misc_feature
<222> LOCATION: (63)..(64)
<223> OTHER INFORMATION: Xaa63 and Xaa64 independently can be Ala, Arg,
      Asn, Asp, Cys, Glu, Gln, Gly, His, Ile, Leu, Lys, Met, Phe, Pro,
      Ser, Thr, Trp, Tyr, Val or a peptide bond
<220> FEATURE:
<221> NAME/KEY: misc_feature
<222> LOCATION: (66)..(69)
<223> OTHER INFORMATION: Xaa66 and Xaa67 independently can be Ala, Arg,
      Asn, Asp, Cys, Glu, Gln, Gly, His, Ile, Leu, Lys, Met, Phe, Pro,
      Ser, Thr, Trp, Tyr or Val; Xaa68 can be Ala, Gly, Pro, Ser or Thr;
      Xaa69 can be Arg, Asn, Asp, Glu, Gln, His, Lys, Ser or Thr
<220> FEATURE:
<221> NAME/KEY: misc_feature
<222> LOCATION: (70)..(71)
<223> OTHER INFORMATION: Xaa70 can be Ala, Gly, Pro, Ser or Thr; Xaa71
      can be Ala, Arg, Asn, Asp, Cys, Glu, Gln, Gly, His, Ile, Leu, Lys,
      Met, Phe, Pro, Ser, Thr, Trp, Tyr or Val
<220> FEATURE:
<221> NAME/KEY: misc_feature
<222> LOCATION: (75)..(77)
<223> OTHER INFORMATION: Xaa75 can be Ala, Arg, Asn, Asp, Cys, Glu, Gln,
      Gly, His, Ile, Leu, Lys, Met, Phe, Pro, Ser, Thr, Trp, Tyr or Val;
      Xaa76 can be Arg, or Lys; Xaa77 can be Cys, Ile, Leu, Met, Phe,
      Trp, Tyr or Val
<220> FEATURE:
```

```
<221> NAME/KEY: misc_feature
<222> LOCATION: (80)..(80)
<223> OTHER INFORMATION: Xaa80 can be Ile, Leu, Met or Val
<220> FEATURE:
<221> NAME/KEY: misc_feature
<222> LOCATION: (82)..(82)
<223> OTHER INFORMATION: Xaa82 can be Ile, Leu, Met or Val
<220> FEATURE:
<221> NAME/KEY: misc_feature
<222> LOCATION: (84)..(86)
<223> OTHER INFORMATION: Xaa84 and Xaa85 independently can be Ala, Arg,
     Asn, Asp, Cys, Glu, Gln, Gly, His, Ile, Leu, Lys, Met, Phe, Pro,
     Ser, Thr, Trp, Tyr or Val; Xaa86 can be Asp or Glu
<220> FEATURE:
<221> NAME/KEY: misc_feature
<222> LOCATION: (87)..(88)
<223> OTHER INFORMATION: Xaa87 can be Ala, Arg, Asn, Asp, Cys, Glu, Gln,
     Gly, His, Ile, Leu, Lys, Met, Phe, Pro, Ser, Thr, Trp, Tyr or Val;
     Xaa88 can be Arg, Asn, Asp, Glu, Gln, His, Lys, Ser or Thr
<220> FEATURE:
<221> NAME/KEY: misc_feature
<222> LOCATION: (89)..(91)
<223> OTHER INFORMATION: Xaa89 can be Ala, Arg, Asn, Asp, Cys, Glu, Gln,
     Gly, His, Ile, Leu, Lys, Met, Phe, Pro, Ser, Thr, Trp, Tyr or Val;
     Xaa90 can be Arg, Asn, Asp, Glu, Gln, His, Lys, Ser or Thr; Xaa91
     is Ile or Val
<220> FEATURE:
<221> NAME/KEY: misc_feature
<222> LOCATION: (92)..(103)
<223> OTHER INFORMATION: Xaa92 can be Ala, Arg, Asn, Asp, Cys, Glu, Gln,
     Gly, His, Ile, Leu, Lys, Met, Phe, Pro, Ser, Thr, Trp, Tyr or Val;
     Xaa93 can be Cys, Ile, Leu, Met, Phe, Trp, Tyr or Val; Xaa94 can
     be Arg or Lys
<220> FEATURE:
<221> NAME/KEY: misc_feature
<222> LOCATION: (95)..(95)
<223> OTHER INFORMATION: Xaa95 can be Arg, Asn, Asp, Glu, Gln, His, Lys,
     Ser or Thr
<220> FEATURE:
<221> NAME/KEY: misc_feature
<222> LOCATION: (100)..(103)
<223> OTHER INFORMATION: Xaa100 can be Ile or Val; Xaa101 can be Ala,
     Arg, Asn, Asp, Cys, Glu, Gln, Gly, His, Ile, Leu, Lys, Met, Phe,
     Pro, Ser, Thr, Trp, Tyr or Val; Xaa102 can be Arg, Asn, Asp, Glu,
     Gln, His, Lys, Ser or Thr; Xaa103 can be Arg, Gln, Glu or Lys
<220> FEATURE:
<221> NAME/KEY: misc_feature
<222> LOCATION: (105)..(105)
<223> OTHER INFORMATION: Xaa105 can be Ala, Gly, Pro, Ser or Thr
<220> FEATURE:
<221> NAME/KEY: misc_feature
<222> LOCATION: (107)..(107)
<223> OTHER INFORMATION: Xaa107 can be Ala, Arg, Asn, Asp, Cys, Glu,
     Gln, Gly, His, Ile, Leu, Lys, Met, Phe, Pro, Ser, Thr, Trp, Tyr or
     Val

<400> SEQUENCE: 66

Cys Xaa Xaa Xaa Xaa Xaa Xaa Xaa Phe Xaa Xaa Xaa Xaa Trp Xaa
1               5                   10                  15

Xaa Trp Xaa Xaa Ala Pro Xaa Xaa Xaa Xaa Xaa Xaa Cys Xaa Gly
            20                  25                  30

Xaa Cys Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Pro Xaa Xaa Xaa Xaa Xaa Xaa Cys Val Pro Xaa Xaa Xaa Ser Pro Xaa
65                  70                  75                  80

Ser Xaa Leu Xaa Xaa Xaa Xaa Xaa Xaa Xaa Xaa Xaa Xaa Xaa Tyr
            85                  90                  95

Glu Asp Met Xaa Xaa Xaa Xaa Cys Xaa Cys Xaa
                100                 105
```

<210> SEQ ID NO 67
<211> LENGTH: 109
<212> TYPE: PRT
<213> ORGANISM: Artificial Sequence
<220> FEATURE:
<223> OTHER INFORMATION: Description of Artificial Sequence: INHIBIN
    SUBGROUP PATTERN
<220> FEATURE:
<221> NAME/KEY: misc_feature
<222> LOCATION: (2)..(3)
<223> OTHER INFORMATION: Xaa2 can be Ala, Arg, Asn, Asp, Cys, Glu, Gln,
    Gly, His, Ile, Leu, Lys, Met, Phe, Pro, Ser, Thr, Trp, Tyr or Val;
    Xaa3 is Arg or Lys
<220> FEATURE:
<221> NAME/KEY: misc_feature
<222> LOCATION: (4)..(6)
<223> OTHER INFORMATION: Xaa4 and Xaa5 independently can be Ala, Arg,
    Asn, Asp, Cys, Glu, Gln, Gly, His, Ile, Leu, Lys, Met, Phe, Pro,
    Ser, Thr, Trp, Tyr or Val; Xaa6 can be Cys, Ile, Leu, Met, Phe,
    Trp, Tyr or Val
<220> FEATURE:
<221> NAME/KEY: misc_feature
<222> LOCATION: (7)..(9)
<223> OTHER INFORMATION: Xaa7 can be Ala, Arg, Asn, Asp, Cys, Glu, Gln,
    Gly, His, Ile, Leu, Lys, Met, Phe, Pro, Ser, Thr, Trp, Tyr or Val;
    Xaa8 can be Ile or Val; Xaa9 can be Arg, Asn, Asp, Glu, Gln, His,
    Lys, Ser or Thr
<220> FEATURE:
<221> NAME/KEY: misc_feature
<222> LOCATION: (11)..(13)
<223> OTHER INFORMATION: Xaa11 can be Arg, Gln, Glu or Lys; Xaa12 can be
    Ala, Arg, Asn, Asp, Cys, Glu, Gln, Gly, His, Ile, Leu, Lys, Met,
    Phe, Pro, Ser, Thr, Trp, Tyr or Val; Xaa13 can be Ile, Leu, Met or
    Val
<220> FEATURE:
<221> NAME/KEY: misc_feature
<222> LOCATION: (16)..(17)
<223> OTHER INFORMATION: Xaa16 can be Asn, Asp or Glu; Xaa17 can be Arg,
    Asn, Asp, Glu, Gln, His, Lys, Ser or Thr
<220> FEATURE:
<221> NAME/KEY: misc_feature
<222> LOCATION: (20)..(21)
<223> OTHER INFORMATION: Xaa20 can be Ile or Val; Xaa21 can be Ala, Arg,
    Asn, Asp, Cys, Glu, Gln, Gly, His, Ile, Leu, Lys, Met, Phe, Pro,
    Ser, Thr, Trp, Tyr or Val
<220> FEATURE:
<221> NAME/KEY: misc_feature
<222> LOCATION: (23)..(27)
<223> OTHER INFORMATION: Xaa23 and Xaa24 independently can be Ala, Gly,
    Pro, Ser or Thr; Xaa25 can be Phe, Tr or Tyr; Xaa26 and Xaa27
    independently can beAla, Arg, Asn, Asp, Cys, Glu, Gln, Gly, His,
    Ile, Leu, Lys, Met, Phe, Pro, Ser, Thr, Trp, Tyr or Val
<220> FEATURE:
<221> NAME/KEY: misc_feature
<222> LOCATION: (28)..(28)
<223> OTHER INFORMATION: Xaa28 can be Arg, Asn, Asp, Glu, Gln, His, Lys,
    Ser or Thr
<220> FEATURE:
<221> NAME/KEY: misc_feature
<222> LOCATION: (31)..(31)
<223> OTHER INFORMATION: Xaa31 can be Arg, Asn, Asp, Glu, Gln, His, Lys,
    Ser or Thr
<220> FEATURE:
<221> NAME/KEY: misc_feature
<222> LOCATION: (33)..(33)
<223> OTHER INFORMATION: Xaa33 can be Ala, Arg, Asn, Asp, Cys, Glu, Gln,
    Gly, His, Ile, Leu, Lys, Met, Phe, Pro, Ser, Thr, Trp, Tyr or Val
<220> FEATURE:
<221> NAME/KEY: misc_feature
<222> LOCATION: (35)..(38)
<223> OTHER INFORMATION: Xaa35 can be Ala, Gly, Pro, Ser or Thr; Xaa36
    can be Ala, Arg, Asn, Asp, Cys, Glu, Gln, Gly, His, Ile, Leu, Lys,
    Met, Phe, Pro, Ser, Thr, Trp, Tyr or Val; Xaa37 can be His, Phe,
    Trp or Tyr; Xaa38 can be Ile, Leu, Met or Val
<220> FEATURE:
<221> NAME/KEY: misc_feature
<222> LOCATION: (39)..(43)
<223> OTHER INFORMATION: Xaa39 and Xaa40 independently can be Ala, Gly, -continued

```
      Pro, Ser or Thr; Xaa41 and Xaa42 independently can be Ala, Arg,
      Asn, Asp, Cys, Glu, Gln, Gly, His, Ile, Leu, Lys, Met, Phe, Pro,
      Ser, Thr, Trp, Tyr or Val; Xaa43 can be Ala, Gly, Pro, Ser or Thr
<220> FEATURE:
<221> NAME/KEY: misc_feature
<222> LOCATION: (44)..(45)
<223> OTHER INFORMATION: Xaa44 can be Ala, Arg, Asn, Asp, Cys, Glu, Gln,
      Gly, His, Ile, Leu, Lys, Met, Phe, Pro, Ser, Thr, Trp, Tyr or Val;
      Xaa45 can be Ala, Gly, Pro, Ser or Thr
<220> FEATURE:
<221> NAME/KEY: misc_feature
<222> LOCATION: (46)..(47)
<223> OTHER INFORMATION: Xaa46 can be Ala, Arg, Asn, Asp, Cys, Glu, Gln,
      Gly, His, Ile, Leu, Lys, Met, Phe, Pro, Ser, Thr, Trp, Tyr or Val;
      Xaa47 can be Ala, Gly, Pro, Ser or Thr
<220> FEATURE:
<221> NAME/KEY: misc_feature
<222> LOCATION: (48)..(51)
<223> OTHER INFORMATION: Xaa48 and Xaa49 independently can be Ala, Arg,
      Asn, Asp, Cys, Glu, Gln, Gly, His, Ile, Leu, Lys, Met, Phe, Pro,
      Ser, Thr, Trp, Tyr or Val; Xaa50 and Xaa51 independently can be
      Ala, Gly, Pro, Ser or Thr
<220> FEATURE:
<221> NAME/KEY: misc_feature
<222> LOCATION: (52)..(55)
<223> OTHER INFORMATION: Xaa52 to Xaa54 independently can be Ala, Arg,
      Asn, Asp, Cys, Glu, Gln, Gly, His, Ile, Leu, Lys, Met, Phe, Pro,
      Ser, Thr, Trp, Tyr or Val; Xaa55 can be Arg, Asn, Asp, Glu, Gln,
      His, Lys, Ser or Thr
<220> FEATURE:
<221> NAME/KEY: misc_feature
<222> LOCATION: (56)..(59)
<223> OTHER INFORMATION: Xaa56 to Xaa59 indepedently can be Ala, Arg,
      Asn, Asp, Cys, Glu, Gln, Gly, His, Ile, Leu, Lys, Met, Phe, Pro,
      Ser, Thr, Trp, Tyr or Val
<220> FEATURE:
<221> NAME/KEY: misc_feature
<222> LOCATION: (60)..(63)
<223> OTHER INFORMATION: Xaa60 to Xaa63 can be Ala, Arg, Asn, Asp, Cys,
      Glu, Gln, Gly, His, Ile, Leu, Lys, Met, Phe, Pro, Ser, Thr, Trp,
      Tyr, Val or a peptide bond
<220> FEATURE:
<221> NAME/KEY: misc_feature
<222> LOCATION: (64)..(65)
<223> OTHER INFORMATION: Xaa64 can be Ala, Arg, Asn, Asp, Cys, Glu, Gln,
      Gly, His, Ile, Leu, Lys, Met, Phe, Pro, Ser, Thr, Trp, Tyr or Val;
      Xaa65 can be Ala, Gly, Pro, Ser or Thr
<220> FEATURE:
<221> NAME/KEY: misc_feature
<222> LOCATION: (66)..(69)
<223> OTHER INFORMATION: Xaa66 to Xaa67 independently can be Ala, Arg,
      Asn, Asp, Cys, Glu, Gln, Gly, His, Ile, Leu, Lys, Met, Phe, Pro,
      Ser, Thr, Trp, Tyr or Val; Xaa68 can be Arg, Asn, Asp, Glu, Gln,
      His, Lys, Ser or Thr; Xaa69 can be Ala, Gly, Pro, Ser or Thr
<220> FEATURE:
<221> NAME/KEY: misc_feature
<222> LOCATION: (72)..(72)
<223> OTHER INFORMATION: Xaa72 can be Ala, Arg, Asn, Asp, Cys, Glu, Gln,
      Gly, His, Ile, Leu, Lys, Met, Phe, Pro, Ser, Thr, Trp, Tyr or Val
<220> FEATURE:
<221> NAME/KEY: misc_feature
<222> LOCATION: (73)..(74)
<223> OTHER INFORMATION: Xaa73 and Xaa74 independently can be Ala, Arg,
      Asn, Asp, Cys, Glu, Gln, Gly, His, Ile, Leu, Lys, Met, Phe, Pro,
      Ser, Thr, Trp, Tyr or Val
<220> FEATURE:
<221> NAME/KEY: misc_feature
<222> LOCATION: (76)..(80)
<223> OTHER INFORMATION: Xaa76 can be Ala, Gly, Pro, Ser or Thr; Xaa77
      can be Arg, Asn, Asp, Glu, Gln, His, Lys, Ser or Thr; Xaa78 can be
      Leu or Met; Xaa79 can be Arg, Asn, Asp, Glu, Gln, His, Lys, Ser or
      Thr; Xaa80 can be Ala, Gly, Pro, Ser or Thr
<220> FEATURE:
<221> NAME/KEY: misc_feature
<222> LOCATION: (81)..(83)
<223> OTHER INFORMATION: Xaa81 can be Leu or Met; Xaa82 can be Arg, Asn,
      Asp, Glu, Gln, His, Lys, Ser or Thr; Xaa83 can be Ile, Leu, Met or
      Val
<220> FEATURE:
```

```
<221> NAME/KEY: misc_feature
<222> LOCATION: (84)..(87)
<223> OTHER INFORMATION: Xaa84 to Xaa86 independently can be Ala, Arg,
      Asn, Asp, Cys, Glu, Gln, Gly, His, Ile, Leu, Lys, Met, Phe, Pro,
      Ser, Thr, Trp, Tyr or Val; Xaa87 can be Arg, Asn, Asp, Glu, Gln,
      His, Lys, Ser or Thr
<220> FEATURE:
<221> NAME/KEY: misc_feature
<222> LOCATION: (89)..(89)
<223> OTHER INFORMATION: Xaa89 can be Ala, Arg, Asn, Asp, Cys, Glu, Gln,
      Gly, His, Ile, Leu, Lys, Met, Phe, Pro, Ser, Thr, Trp, Tyr or Val
<220> FEATURE:
<221> NAME/KEY: misc_feature
<222> LOCATION: (90)..(90)
<223> OTHER INFORMATION: Xaa90 can be Ala, Arg, Asn, Asp, Cys, Glu, Gln,
      Gly, His, Ile, Leu, Lys, Met, Phe, Pro, Ser, Thr, Trp, Tyr, Val or
      a peptide bond
<220> FEATURE:
<221> NAME/KEY: misc_feature
<222> LOCATION: (91)..(93)
<223> OTHER INFORMATION: Xaa91 can be Ala, Arg, Asn, Asp, Cys, Glu, Gln,
      Gly, His, Ile, Leu, Lys, Met, Phe, Pro, Ser, Thr, Trp, Tyr or Val;
      Xaa92 can be Arg, Asn, Asp, Glu, Gln, His, Lys, Ser or Thr; Xaa93
      can be Cys, Ile, Leu, Met, Phe, Trp, Tyr or Val
<220> FEATURE:
<221> NAME/KEY: misc_feature
<222> LOCATION: (94)..(97)
<223> OTHER INFORMATION: Xaa94 to Xaa95 independently can be Ala, Arg,
      Asn, Asp, Cys, Glu, Gln, Gly, His, Ile, Leu, Lys, Met, Phe, Pro,
      Ser, Thr, Trp, Tyr or Val; Xaa96 can be Arg, Gln, Glu or Lys;
      Xaa97 can be Arg, Asn, Asp, Glu, Gln, His, Lys, Ser or Thr
<220> FEATURE:
<221> NAME/KEY: misc_feature
<222> LOCATION: (98)..(99)
<223> OTHER INFORMATION: Xaa98 can be Ile or Val; Xaa99 can be Ala, Arg,
      Asn, Asp, Cys, Glu, Gln, Gly, His, Ile, Leu, Lys, Met, Phe, Pro,
      Ser, Thr, Trp, Tyr or Val
<220> FEATURE:
<221> NAME/KEY: misc_feature
<222> LOCATION: (101)..(104)
<223> OTHER INFORMATION: Xaa101 can be Leu or Met; Xaa102 can be Ile,
      Leu, Met or Val; Xaa103 can be Ala, Arg, Asn, Asp, Cys,Glu, Gln,
      Gly, His, Ile, Leu, Lys, Met, Phe, Pro, Ser, Thr, Trp, Tyr or Val;
      Xaa104 can be Gln or Glu
<220> FEATURE:
<221> NAME/KEY: misc_feature
<222> LOCATION: (105)..(105)
<223> OTHER INFORMATION: Xaa105 can be Arg, Asn, Asp, Glu, Gln, His,
      Lys, Ser or Thr
<220> FEATURE:
<221> NAME/KEY: misc_feature
<222> LOCATION: (107)..(107)
<223> OTHER INFORMATION: Xaa107 can be Ala or Gly
<220> FEATURE:
<221> NAME/KEY: misc_feature
<222> LOCATION: (109)..(109)
<223> OTHER INFORMATION: Xaa109 can be Ala, Arg, Asn, Asp, Cys,Glu, Gln,
      Gly, His, Ile, Leu, Lys, Met, Phe, Pro, Ser, Thr, Trp, Tyr or Val

<400> SEQUENCE: 67

Cys Xaa Xaa Xaa Xaa Xaa Xaa Xaa Phe Xaa Xaa Xaa Gly Trp Xaa
1               5                   10                  15

Xaa Trp Ile Xaa Xaa Pro Xaa Xaa Xaa Xaa Xaa Tyr Cys Xaa Gly
            20                  25                  30

Xaa Cys Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Cys Cys Xaa Xaa Xaa Pro Xaa Xaa Xaa Xaa
65                  70                  75                  80

Xaa Xaa Xaa Xaa Xaa Xaa Xaa Asp Xaa Xaa Xaa Xaa Xaa Xaa Xaa
                85                  90                  95
```

```
Xaa Xaa Xaa Asn Xaa Xaa Xaa Xaa Cys Xaa Cys Xaa
            100             105
```

<210> SEQ ID NO 68
<211> LENGTH: 139
<212> TYPE: PRT
<213> ORGANISM: Homo sapiens
<220> FEATURE:
<223> OTHER INFORMATION: Mature H2223 mutant

<400> SEQUENCE: 68

```
Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Asn Val Ile Leu Lys Lys Tyr
        115                 120                 125

Glu Asp Met Val Val Glu Ala Cys Gly Cys Arg
    130                 135
```

<210> SEQ ID NO 69
<211> LENGTH: 117
<212> TYPE: PRT
<213> ORGANISM: Homo sapiens
<220> FEATURE:
<223> OTHER INFORMATION: Trypsin truncated H2223 mutant

<400> SEQUENCE: 69

```
Met Ala Asn Val Ala Glu Asn Ser Ser Ser Asp Gln Arg Gln Ala Cys
1               5                   10                  15

Lys Lys His Glu Leu Tyr Val Ser Phe Arg Asp Leu Gly Trp Gln Asp
            20                  25                  30

Trp Ile Ile Ala Pro Glu Gly Tyr Ala Ala Tyr Tyr Cys Glu Gly Glu
        35                  40                  45

Cys Ala Phe Pro Leu Asn Ser Tyr Met Asn Ala Thr Asn His Ala Ile
    50                  55                  60

Val Gln Thr Leu Val His Phe Ile Asn Pro Glu Thr Val Pro Lys Pro
65                  70                  75                  80

Cys Cys Ala Pro Thr Gln Leu Asn Ala Ile Ser Val Leu Tyr Phe Asp
                85                  90                  95

Asp Ser Ser Asn Val Ile Leu Lys Lys Tyr Glu Asp Met Val Val Glu
            100                 105                 110

Ala Cys Gly Cys Arg
        115
```

<210> SEQ ID NO 70
<211> LENGTH: 33
<212> TYPE: DNA
<213> ORGANISM: Artificial Sequence

```
<220> FEATURE:
<223> OTHER INFORMATION: Description of Artificial Sequence: Primer #1
<220> FEATURE:
<221> NAME/KEY: CDS
<222> LOCATION: (1)..(33)

<400> SEQUENCE: 70 gcg ccc acg cag ctc agc gct atc tcc gtc ctc                    33
Ala Pro Thr Gln Leu Ser Ala Ile Ser Val Leu
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Amino acid sequence encoded by Primer #1

<400> SEQUENCE: 71

Ala Pro Thr Gln Leu Ser Ala Ile Ser Val Leu
1               5                   10

<210> SEQ ID NO 72
<211> LENGTH: 43
<212> TYPE: DNA
<213> ORGANISM: Artificial Sequence
<220> FEATURE:
<223> OTHER INFORMATION: Description of Artificial Sequence: Primer #2

<400> SEQUENCE: 72
ctatctgcag ccacaagctt cgaccaccat gtcttcgtat ttc                 43

<210> SEQ ID NO 73
<211> LENGTH: 43
<212> TYPE: DNA
<213> ORGANISM: Artificial Sequence
<220> FEATURE:
<223> OTHER INFORMATION: Description of Artificial Sequence: Complement
      of Primer #2
<220> FEATURE:
<221> NAME/KEY: CDS
<222> LOCATION: (2)..(43)

<400> SEQUENCE: 73 g aaa tac gaa gac atg gtg gtc gaa gct tgt ggc tgc aga tag       43
  Lys Tyr Glu Asp Met Val Val Glu Ala Cys Gly Cys Arg
  1               5                   10

<210> SEQ ID NO 74
<211> LENGTH: 13
<212> TYPE: PRT
<213> ORGANISM: Artificial Sequence
<220> FEATURE:
<223> OTHER INFORMATION: Amino acid sequence encoded by complement of
      Primer #2

<400> SEQUENCE: 74

Lys Tyr Glu Asp Met Val Val Glu Ala Cys Gly Cys Arg
1               5                   10

<210> SEQ ID NO 75
<211> LENGTH: 44
<212> TYPE: DNA
<213> ORGANISM: Artificial Sequence
<220> FEATURE:
<223> OTHER INFORMATION: Description of Artificial Sequence: the
      sequence between the T7 promoter, at the XbaI site, and the ATG
      codon
```

<400> SEQUENCE: 75
tctagaataa ttttgtttaa cctttaagaa ggagatatac gatg                    44

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence: Primer #3

<400> SEQUENCE: 76
taatacgact cactatagg                                                19

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Primer #4

<400> SEQUENCE: 77
gctgagctgc gtgggcgc                                                 18

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: complement
      of Primer #4
<220> FEATURE:
<221> NAME/KEY: CDS
<222> LOCATION: (1)..(18)

<400> SEQUENCE: 78 gcg ccc acg cag ctc agc                                             18
Ala Pro Thr Gln Leu Ser
1               5

<210> SEQ ID NO 79
<211> LENGTH: 6
<212> TYPE: PRT
<213> ORGANISM: Artificial Sequence
<220> FEATURE:
<223> OTHER INFORMATION: Amino acid sequence encoded by complement of
      Primer #4

<400> SEQUENCE: 79

Ala Pro Thr Gln Leu Ser
1               5

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Primer #5

<400> SEQUENCE: 80
ggatcctatc tgcagccaca agc                                           23

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: complement

```
                    of Primer #5
<220> FEATURE:
<221> NAME/KEY: CDS
<222> LOCATION: (1)..(18)

<400> SEQUENCE: 81 gct tgt ggc tgc aga tag gatcc                                        23
Ala Cys Gly Cys Arg
1               5

<210> SEQ ID NO 82
<211> LENGTH: 5
<212> TYPE: PRT
<213> ORGANISM: Artificial Sequence
<220> FEATURE:
<223> OTHER INFORMATION: Amino acid sequence encoded by complement of
      Primer #5

<400> SEQUENCE: 82

Ala Cys Gly Cys Arg
1               5

<210> SEQ ID NO 83
<211> LENGTH: 102
<212> TYPE: PRT
<213> ORGANISM: Homo sapiens
<220> FEATURE:
<223> OTHER INFORMATION: CDMP-1/GDF-5

<400> SEQUENCE: 83

Cys Ser Arg Lys Ala Leu His Val Asn Phe Lys Asp Met Gly Trp Asp
1               5                   10                  15

Asp Trp Ile Ile Ala Pro Leu Glu Tyr Glu Ala Phe His Cys Glu Gly
            20                  25                  30

Leu Cys Glu Phe Pro Leu Arg Ser His Leu Glu Pro Thr Asn His Ala
        35                  40                  45

Val Ile Gln Thr Leu Met Asn Ser Met Asp Pro Glu Ser Thr Pro Pro
    50                  55                  60

Thr Cys Cys Val Pro Thr Arg Leu Ser Pro Ile Ser Ile Leu Phe Ile
65                  70                  75                  80

Asp Ser Ala Asn Asn Val Val Tyr Lys Gln Tyr Glu Asp Met Val Val
                85                  90                  95

Glu Ser Cys Gly Cys Arg
            100

<210> SEQ ID NO 84
<211> LENGTH: 102
<212> TYPE: PRT
<213> ORGANISM: Homo sapiens
<220> FEATURE:
<223> OTHER INFORMATION: CDMP-2/GDF-6

<400> SEQUENCE: 84

Cys Ser Lys Lys Pro Leu His Val Asn Phe Lys Glu Leu Gly Trp Asp
1               5                   10                  15

Asp Trp Ile Ile Ala Pro Leu Glu Tyr Glu Ala Tyr His Cys Glu Gly
            20                  25                  30

Val Cys Asp Phe Pro Leu Arg Ser His Leu Glu Pro Thr Asn His Ala
        35                  40                  45

Ile Ile Gln Thr Leu Met Asn Ser Met Asp Pro Gly Ser Thr Pro Pro
    50                  55                  60

Ser Cys Cys Val Pro Thr Lys Leu Thr Pro Ile Ser Ile Leu Tyr Ile
```

```
65                  70                  75                  80
Asp Ala Gly Asn Asn Val Val Tyr Lys Gln Tyr Glu Asp Met Val Val
                85                  90                  95

Glu Ser Cys Gly Cys Arg
            100

<210> SEQ ID NO 85
<211> LENGTH: 102
<212> TYPE: PRT
<213> ORGANISM: Mus musculus
<220> FEATURE:
<223> OTHER INFORMATION: GDF-6

<400> SEQUENCE: 85

Cys Ser Arg Lys Pro Leu His Val Asn Phe Lys Glu Leu Gly Trp Asp
1               5                   10                  15

Asp Trp Ile Ile Ala Pro Leu Glu Tyr Glu Ala Tyr His Cys Glu Gly
            20                  25                  30

Val Cys Asp Phe Pro Leu Arg Ser His Leu Glu Pro Thr Asn His Ala
        35                  40                  45

Ile Ile Gln Thr Leu Met Asn Ser Met Asp Pro Gly Ser Thr Pro Pro
    50                  55                  60

Ser Cys Cys Val Pro Thr Lys Leu Thr Pro Ile Ser Ile Leu Tyr Ile
65                  70                  75                  80

Asp Ala Gly Asn Asn Val Val Tyr Lys Gln Tyr Glu Asp Met Val Val
                85                  90                  95

Glu Ser Cys Gly Cys Arg
            100

<210> SEQ ID NO 86
<211> LENGTH: 102
<212> TYPE: PRT
<213> ORGANISM: Bos taurus
<220> FEATURE:
<223> OTHER INFORMATION: CDMP-2

<400> SEQUENCE: 86

Cys Ser Lys Lys Pro Leu His Val Asn Phe Lys Glu Leu Gly Trp Asp
1               5                   10                  15

Asp Trp Ile Ile Ala Pro Leu Glu Tyr Glu Ala Tyr His Cys Glu Gly
            20                  25                  30

Val Cys Asp Phe Pro Leu Arg Ser His Leu Glu Pro Thr Asn His Ala
        35                  40                  45

Ile Ile Gln Thr Leu Met Asn Ser Met Asp Pro Gly Ser Thr Pro Pro
    50                  55                  60

Ser Cys Cys Val Pro Thr Lys Leu Thr Pro Ile Ser Ile Leu Tyr Ile
65                  70                  75                  80

Asp Ala Gly Asn Asn Val Val Tyr Asn Glu Tyr Glu Glu Met Val Val
                85                  90                  95

Glu Ser Cys Gly Cys Arg
            100

<210> SEQ ID NO 87
<211> LENGTH: 102
<212> TYPE: PRT
<213> ORGANISM: Mus musculus
<220> FEATURE:
<223> OTHER INFORMATION: GDF-7

<400> SEQUENCE: 87
```

Cys Ser Arg Lys Ser Leu His Val Asp Phe Lys Glu Leu Gly Trp Asp
1               5                   10                  15

Asp Trp Ile Ile Ala Pro Leu Asp Tyr Glu Ala Tyr His Cys Glu Gly
            20                  25                  30

Val Cys Asp Phe Pro Leu Arg Ser His Leu Glu Pro Thr Asn His Ala
        35                  40                  45

Ile Ile Gln Thr Leu Leu Asn Ser Met Ala Pro Asp Ala Ala Pro Ala
    50                  55                  60

Ser Cys Cys Val Pro Ala Arg Leu Ser Pro Ile Ser Ile Leu Tyr Ile
65                  70                  75                  80

Asp Ala Ala Asn Asn Val Val Tyr Lys Gln Tyr Glu Asp Met Val Val
                85                  90                  95

Glu Ala Cys Gly Cys Arg
            100

<210> SEQ ID NO 88
<211> LENGTH: 102
<212> TYPE: PRT
<213> ORGANISM: Homo sapiens
<220> FEATURE:
<223> OTHER INFORMATION: CDMP-3 construct

<400> SEQUENCE: 88

Cys Ser Arg Lys Pro Leu His Val Asp Phe Lys Glu Leu Gly Trp Asp
1               5                   10                  15

Asp Trp Ile Ile Ala Pro Leu Asp Tyr Glu Ala Tyr His Cys Glu Gly
            20                  25                  30

Leu Cys Asp Phe Pro Leu Arg Ser His Leu Glu Pro Thr Asn His Ala
        35                  40                  45

Ile Ile Gln Thr Leu Leu Asn Ser Met Ala Pro Asp Ala Ala Pro Ala
    50                  55                  60

Ser Cys Cys Val Pro Ala Arg Leu Ser Pro Ile Ser Ile Leu Tyr Ile
65                  70                  75                  80

Asp Ala Ala Asn Asn Val Val Tyr Lys Gln Tyr Glu Asp Met Val Val
                85                  90                  95

Glu Ala Cys Gly Cys Arg
            100

<210> SEQ ID NO 89
<211> LENGTH: 442
<212> TYPE: DNA
<213> ORGANISM: Homo sapiens
<220> FEATURE:
<223> OTHER INFORMATION: H2475 mutant

<400> SEQUENCE: 89
ccatggcagc caacaaacgt ctaaaaaatc aaaaccgcaa taaatccagc tctcatcagg      60
actcctccag aatgtccagt gttggagatt ataacacaag tgagcaaaaa caagcctgta    120
agaagcacga actctatgtg agcttccggg atctgggatg caggactcc attatagcac     180 cagaaggata cgctgccatt ttattgtgat ggagaatgtt cttttccact aacgcccat    240 atgaatgcca ccaaccacgc tatagttcag actctggttc atctgatgtt tcctgaccag    300
cgtaccaaag ccttgttgtg ctccaaccaa attaaatgcc atctctgttc tgtactttga    360
tgacagctcc aacgtcatcc tgaagaaata cgaagacatg gtggtcgaag cttgtggctg    420
cagatagctc ctccgagaat tc                                             442

```
<210> SEQ ID NO 90
<211> LENGTH: 140
<212> TYPE: PRT
<213> ORGANISM: Homo sapiens
<220> FEATURE:
<223> OTHER INFORMATION: H2475 mutant

<400> SEQUENCE: 90

Met Ala Ala Asn Lys Arg Leu Lys Asn Gln Asn Arg Asn Lys Ser Ser
1               5                   10                  15

Ser His Gln Asp Ser Ser Arg Met Ser Ser Val Gly Asp Tyr Asn Thr
            20                  25                  30

Ser Glu Gln Lys Gln Ala Cys Lys Lys His Glu Leu Tyr Val Ser Phe
        35                  40                  45

Arg Asp Leu Gly Trp Gln Asp Trp Ile Ile Ala Pro Glu Gly Tyr Ala
    50                  55                  60

Ala Phe Tyr Cys Asp Gly Glu Cys Ser Phe Pro Leu Asn Ala His Met
65                  70                  75                  80

Asn Ala Thr Asn His Ala Ile Val Gln Thr Leu Val His Leu Met Phe
                85                  90                  95

Pro Asp His Val Pro Lys Pro Cys Cys Ala Pro Thr Lys Leu Asn Ala
            100                 105                 110

Ile Ser Val Leu Tyr Phe Asp Asp Ser Ser Asn Val Ile Leu Lys Lys
            115                 120                 125

Tyr Glu Asp Met Val Val Glu Ala Cys Gly Cys Arg
            130                 135                 140
```

What is claimed is:

1. An OP-1 mutant which differs from SEQ ID NO: 39 by at least one amino acid residue substitution, wherein said amino acid substitution is:

substitution of arginine, isoleucine, leucine, serine or alanine at residue 431 of SEQ ID NO: 39; or substitution of an acidic or hydroxyl group-carrying amino acid residue for a basic or amide-bearing amino acid at any one of positions 400, 402, 421, 422 or 426 of SEQ ID NO: 39.

2. The OP-1 mutant of claim 1 wherein said amino acid substitution occurs at residue 400 of OP-1 (SEQ ID NO: 39) and wherein said substituting amino acid is selected from the group consisting of glutamic acid, aspartic acid, threonine and serine.

3. The OP-1 mutant of claim 1 wherein said amino acid substitution is an acidic residue substituting for a basic or amide-bearing amino acid at any one of positions 400, 402, 421, 422 and 426 of SEQ ID NO: 39.

4. The OP-1 mutant of claim 3 wherein said acidic amino acid residue is aspartic acid or glutamic acid.

5. The OP-1 mutant of claim 1 having improved in vitro refolding properties in a pH range of about 6.0–9.0, as compared with the unsubstituted OP-1 protein of SEQ ID NO: 39.

6. The OP-1 mutant of claim 1, wherein said amino acid substitution is at amino acid residue 431 of SEQ ID NO: 39 and wherein said substitution is selected from any one of arginine, isoleucine, leucine, serine and alanine.

7. The OP-1 mutant of claim 1, wherein said amino acid substitution is a hydroxyl group-carrying amino acid residue substituting for a basic or amide-bearing amino acid at any one of positions 400, 402, 421, 422 or 426 of SEQ ID NO: 39.

8. The OP-1 mutant of claim 7, wherein said hydroxyl group-carrying amino acid residue is serine or threonine.

9. The OP-1 mutant of claim 1, wherein said amino acid substitution is at residue 402 of OP-1 (SEQ ID NO: 39), and wherein said substituting amino acid residue is selected from the group consisting of glutamic acid, aspartic acid, threonine and serine.

10. The OP-1 mutant of claim 1, wherein said amine acid substitution is at residue 421 of OP-1 (SEQ ID NO:39), and wherein said substituting amino acid residue is selected from the group consisting of glutamic acid, aspartic acid, threonine and serine.

11. The OP-1 mutant of claim 1, wherein said amine acid substitution is at residue 422 of OP-1 (SEQ ID NO:39), and wherein said substituting amino acid residue is selected from the group consisting of glutamic acid, aspartic acid, threonine and serine.

12. The OP-1 mutant of claim 1, wherein said amine acid substitution is at residue 426 of OP-1 (SEQ ID NO:39), and wherein said substituting amino acid residue is selected from the group consisting of glutamic acid, aspartic acid, threonine and serine.

13. An OP-1 mutant comprising an amino acid sequence of SEQ ID NO: 68 or SEQ ID NO: 69.

* * * * *

UNITED STATES PATENT AND TRADEMARK OFFICE
CERTIFICATE OF CORRECTION

PATENT NO. : 6,677,432 B1
APPLICATION NO. : 09/374958
DATED : January 13, 2004
INVENTOR(S) : Oppermann et al.

It is certified that error appears in the above-identified patent and that said Letters Patent is hereby corrected as shown below:

Cover Page, under (56) Referenced Cited – OTHER PUBLICATIONS Miranda, et al., change "(1996)" to --(1999)--.

Column 2, line 52, change "UNWIN" to --UNIVIN--.

Column 4, line 66, change "pail" to --part--.

Column 5, line 30, change "an" to --art--.

Column 6, line 28, insert --:-- after "positions".

Column 6, line 33, change "positions," to --positions--.

Column 7, line 5, change "arginne, serene" to --arginine, serine--.

Column 7, line 23, change second occurrence of "TGF-β3" to --TGF-β4--.

Column 8, line 16, change "glulathione" to --glutathione--.

Column 8, line 21, change "reluctant" to --reductant--.

Column 31, line 8, change "far laboratory" to --for laboratory--.

Column 9, line 46, change "pour" to --poor--.

Column 10, line 19, change "SMP-3" to --BMP-3--.

Column 11, line 21, change "BM-3" to --BMP-3--.

Column 11, line 40, change "SEQ ID NO:6" to --SEQ ID NO:46--.

Column 11, line 53, change "Inhibin A" to --Inhibin βA--.

Column 11, line 53, change "Inhibin β3" to --Inhibin βB--.

Column 12, line 33, change "GFD" to --GDF--.

Column 13, line 9, change "/hereon" to --thereof)--.

CERTIFICATE OF CORRECTION (continued)
U.S. Pat. No. 6,677,432 B1

Column 13, line 26, change "non naturally" to --non-naturally--.

Column 13, line 52, change "Osleogenic" to --Osteogenic--.

Column 13, line 56, change "of" to --or--.

Column 14, line 26, change "J. Higgins" to --S. J. Higgins--.

Column 15, line 1, insert --.-- after "formation".

Column 15, line 2, change "redifferentation" to --redifferentiation--.

Column 15, line 3, insert --.-- after "path".

Column 15, line 56, change "(pp. 354-352)," to --(pp. 345-352,)--.

Column 17, line 16, change "eukaryotec" to --eukaryotic--.

Column 17, line 51, insert --of-- after "more".

Column 18, line 3, insert --conditions-- after "physiologically-compatible".

Column 19, lines 20-21, change "complimentary" to --complementary--.

Column 17, line 51, change "If, no" to --If no--.

Column 21, line 11, under Table 1, change "Endcrinol." to --Endocrinol.--.

Column 23, line 62, change "show" to --shown--.

Column 25, line 11, change "Xaa pro Cys" to --Xaa Pro Cys--.

Column 25, line 26, change "Thr; Trp" to --Thr, Trp--.

Column 25, line 29, change "Val, Xaa40" to --Val; Xaa40--.

Column 25, line 63, change "Thr, Xaa75" to --Thr; Xaa75--.

Column 26, line 63, change "Gln, Gln;" to --Gln, Glu,--.

Column 26, line 66, change "Gln; Xaa35" to --Glu; Xaa35--.

Column 26, line 66, change "Gln, Gln," to --Gln, Glu,--.

Column 27, line 1, change "Gln, Gln," to --Gln, Glu,--.

CERTIFICATE OF CORRECTION (continued)
U.S. Pat. No. 6,677,432 B1

Column 27, line 2, change "Tip" to --Trp--.

Column 27, line 12, change "Gln, Gln," to --Gln, Glu,--.

Column 27, line 25, change "Gln, Gln," to --Gln, Glu,--.

Column 27, line 29, change "Gln, Gln," to --Gln, Glu,--.

Column 27, line 33, change "Pre" to --Phe--.

Column 27, line 42, change "present al" to --present at--.

Column 28, line 13, change "Tin" to --Thr--.

Column 28, line 16, change "Gln, Gln," to --Glu, Gln,--.

Column 28, line 19, change "Cys, Gln," to --Cys, Glu,--.

Column 28, line 26, change "Thr, Xaa36" to --Thr; Xaa36--.

Column 28, line 32, change "Gln, Gln," to --Gln, Glu,--.

Column 28, line 33, change "Leu; Lys," to --Leu, Lys,--.

Column 29, line 46, change "band" to --bond--.

Column 29, line 59, change "Tip" to --Trp--.

Column 29, line 61, change "Gln" to --Glu--.

Column 29, line 63, change "Gln, Gly," to --Gln, Glu,--.

Column 30, line 2, change "Or" to --or--.

Column 30, line 47, insert after "Val;" --Xaa3 is Arg or Lys;--.

Column 30, line 48, change "Xaa3" to --Xaa4--.

Column 30, line 61, change "Xaa3" to --Xaa23--.

Column 31, line 38, change "Xaa67" to --Xaa61--.

Column 31, line 39, change "Tip" to --Trp--.

Column 31, line 50, change "Gln, Gln," to --Gln, Glu,--.

CERTIFICATE OF CORRECTION (continued)
U.S. Pat. No. 6,677,432 B1

Column 31, line 62, change "Gln, Gln," to --Gln, Glu,--.

Column 32, line 4, change "Gln, Gln," to --Gln, Glu,--.

Column 32, line 15, change "Gln" to --Glu--.

Column 34, line 45, change "above," to --above.--.

Column 36, line 8, change "eukaryolic" to --eukaryotic--.

Column 36, line 9, change "transient" to --transfect--.

Column 36, line 10, change "unreatranged" to --unrearranged--.

Column 36, line 47, change "ampliftable" to --amplifiable--.

Column 37, line 4, change "slate" to --state--.

Column 37, line 52, after "Useful" insert --selectable marker genes for use in yeast cells include the URA3, LEU2, HIS3 or TRP1 gene for--.

Column 37, line 60, change "lac, lac," to --lac, tac,--.

Column 38, line 22, change "digironin" to --digitonin--.

Column 38, line 23, change "guanidine;" to --guanidine,--.

Column 38, line 36, change "preferably is in" to --preferably in--.

Column 38, line 37, change "forth" to --form--.

Column 38, line 41, change "an" to --art--.

Column 38, lines 52-53, change "OP-1 BMP-2 or BMP-2 IBMP-6" to --OP-1/BMP-2 or BMP-2/BMP-6--.

Column 40, line 20, change "dinner" to --dimer--.

Column 40, line 26, change "resistant" to --resistance--.

Column 40, line 33, change "dinners" to --dimers--.

Column 41, line 18, change "may" to --assay--.

Column 42, line 51, change "constricts" to --constructs--.

Column 42, line 53, change "to vivo" to --in vivo--.

Column 42, line 64, change "in the an" to --in the art--.

Column 42, line 65, change "detailed" to --detail--.

Column 44, line 27, change "more the" to --more of the--.

Column 44, line 32, change "in vivo," to --in vivo.--.

Column 44, line 47, insert --conditions-- after "compatible".

Column 44, line 59, change "hyalmonic" to --hyaluronic--.

Column 45, line 2, change "in vivo," to --in vivo.--.

Column 45, line 22, change "as well an" to --as well as--.

Column 45, line 49, change "inhibin βC" to --Inhibin βC--.

Column 46, line 12, change "atone" to --at one--.

Column 46, line 19, delete "," after "superfamily".

Column 46, line 44, change "H2421 residues" to --H2421: residues--.

Column 47, line 25, change "dinner" to --dimer--.

Column 49, line 22, change "goad" to --good--.

Column 49, line 58, change "lustidine" to --histidine--.

Column 50, line 22, change "paint" to --point--.

Column 51, line 8, change "$R_{30}>E$" to --R30>E--.

Column 51, line 35, change "This primer lit" to --Primer # 2--.

Column 51, line 63, change "ACC" to --ACG--.

Column 52, line 8, change "for of" to --for--.

Column 52, line 32, change "10mm EDTA" to --10mM EDTA--.

Column 52, line 45, change "Inc.)," to --Inc.).--.

CERTIFICATE OF CORRECTION (continued)
U.S. Pat. No. 6,677,432 B1

Column 52, line 48, change "0.1%/TFA/10% acetonitrile" to --0.1% TFA/10% acetonitrile--.

Column 52, line 48, change "0.1%/TFA/70%" to --0.1% TFA/70%--.

Column 53, line 9, change "polyacrydamide" to --polyacrylamide--.

Column 53, line 11, change "dinners" to --dimers--.

Column 53, line 19, change "0. l%/TFA/30%" to --0.1% TFA/30%--.

Column 53, line 27, change "area" to --urea--.

Column 53, line 39, change "dinner" to --dimer--.

Column 53, line 41, change "dinners" to --dimers--.

Column 53, line 43, change "dialers" to --dimers--.

Column 54, line 8, change "(paranitrosophenylphosphate)glycerine" to --(paranitrosophenylphosphate)/glycerine--.

Column 54, line 10, change "tun" to --run--.

Column 54, line 16, change "214 nm," to --214 nm.--.

Column 54, line 36, change "*Differentation*" to --*Differentiation*--.

Column 54, line 41, change "BM;" to --BM:--.

Column 54, line 44, change "(5 μl/ml)" to --(5 μg/ml)--.

Column 54, line 47, change "triodothyronin" to --triiodothyronin--.

Column 54, line 53, change "day," to --day.--.

Column 54, line 61, change "senum" to --serum--.

Column 55, line 11, change "colorimenic" to --colorimetric--.

Column 55, line 16, change "may" to --assay--.

Column 55, line 17, change "mull-well" to --multi-well--.

Column 55, line 45, change "incubation.," to "incubation,".

Column 56, line 16, change "accessable" to --accessible--.

Column 56, line 26, change "protein induced" to --protein-induced--.

Column 56, line 40, change "hemotoxylin/cosin" to --hematoxylin/eosin--.

Column 57, line 25, change "allribute(s)" to --attribute(s)--.

Column 60, line 21, delete "," after "centrifuged".

Column 60, line 25, change "trough" to --through--.

Column 60, line 63, change "CAMP" to --cAMP--.

Column 61, line 12, change "1 Triton X-100." to --1% Triton X-100.--.

Column 61, line 49, change "far" to --for--.

Column 61, line 66, change "osteoclacin" to --osteocalcin--.

Column 63, line 10, change "well, The" to --well. The--.

Column 63, line 35, change "neoplasiac" to --neoplastic--.

Column 63, line 36, change "neuroblastoma" to --neuroblastomas--.

Column 63, line 57, change "OP-1" to --OP-1,--.

Column 64, line 65, change "tissue) specific" to --tissue-specific--.

Column 65, line 39, change "an" to --art--.

Column 66, line 5, change "hemotoxylinleosin" to --hematoxylin/eosin--.

Column 67, line 8, change "saline rat" to --saline/rat--.

Column 67, line 46, change "tamer matrix" to --carrier matrix--.

Column 67, line 52, change "Lang" to --Long--.

Column 68, line 15, change "time" to --nerve--.

Column 111, SEQ ID NO 64, under Location: (37..37), <223>, change "Leu lys" to --Leu, Lys--.

CERTIFICATE OF CORRECTION (continued)
U.S. Pat. No. 6,677,432 B1

Column 115, SEQ ID NO 65, under Location (66)..(66), <223>, change "Ala Gly" to --Ala, Gly--.

Column 117, SEQ ID NO 65, under Location (99)..(100), <223>, change "Ala Gly" to --Ala, Gly--.

Column 119, SEQ ID NO 66, under location (26)..(29), <223>, change "Ala Gly" to --Ala, Gly--.

Signed and Sealed this

Second Day of March, 2010

David J. Kappos
*Director of the United States Patent and Trademark Office*